United States Patent
Perry et al.

(10) Patent No.: US 6,979,741 B2
(45) Date of Patent: Dec. 27, 2005

(54) ACETYL-COA CARBOXYLASE INHIBITORS

(75) Inventors: David A. Perry, Mystic, CT (US); H. James Harwood, Ledyard, CT (US)

(73) Assignee: Pfizer Inc., New York, NY (US)

( * ) Notice: Subject to any disclaimer, the term of this patent is extended or adjusted under 35 U.S.C. 154(b) by 173 days.

(21) Appl. No.: 10/370,844

(22) Filed: Feb. 20, 2003

(65) Prior Publication Data

US 2003/0187254 A1 Oct. 2, 2003

Related U.S. Application Data

(60) Provisional application No. 60/365,358, filed on Feb. 27, 2002.

(51) Int. Cl.[7] ............................................. C07D 263/08
(52) U.S. Cl. ..................................................... 548/229
(58) Field of Search ................ 544/60, 129; 514/227.8, 514/235.5

(56) References Cited

FOREIGN PATENT DOCUMENTS

| EP | 1099701 | 5/2001 | ......... C07D/401/14 |
| WO | WO0206230 | 1/2002 | ......... C07D/211/00 |
| WO | WO 03/076403 | * 9/2003 | |

* cited by examiner

*Primary Examiner*—Kamal Saeed
(74) *Attorney, Agent, or Firm*—Peter C. Richardson; Gregg C. Benson; Lisa A. Samuels

(57) ABSTRACT

Acetyl Coenzyme A Carboxylase inhibitors, pharmaceutical compositions containing such compounds and the use of such compounds to treat for example, Metabolic Syndrome including atherosclerosis, diabetes and obesity.

1 Claim, No Drawings

ACETYL-COA CARBOXYLASE INHIBITORS

This application claims priority from U.S. Provisional Application No. 60/365,358 filed Feb. 27, 2002.

BACKGROUND OF INVENTION

This invention relates to Acetyl-CoenzymeA Carboxylase (ACC) inhibitors, pharmaceutical compositions containing such inhibitors and the use of such inhibitors to treat, for example, metabolic syndrome, diabetes, obesity, atherosclerosis, and cardiovascular disease in mammals, including humans.

Metabolic syndrome (a.k.a. insulin resistance syndrome, syndrome X) is a common clinical disorder that is defined as the presence of increased insulin concentrations in association with other disorders including visceral obesity, hyperlipidemia and dyslipidemia, hyperglycemia, hypertension, and sometimes hyperuricemia and renal dysfunction.

Metabolic syndrome is considered by many as a common basic defect for type-2 diabetes, android obesity, dyslipidemia, and hypertension, leading to a clustering of these diseases. This syndrome has particular significance since it has been shown to be an antecedent of both type-2 diabetes and atherosclerosis, with cardiovascular events accounting for the majority of deaths in both populations.

It is estimated that more than 100 million people in the U.S. alone suffer from some form of metabolic syndrome.

Recent studies have suggested that abnormal fatty acid metabolism may be at the core of metabolic syndrome. Acetyl-CoA carboxylase (ACC) catalyzes the rate limiting reaction in fatty acid biosynthesis. Malonyl-CoA, the product of the ACC-catalyzed reaction, inhibits mitochondrial fatty acid oxidation through feedback inhibition of carnitine palmitoyltransferase 1 (CPT-1), and therefore plays key roles both in controlling the switch between carbohydrate and fatty acid utilization in liver and skeletal muscle and also in regulating insulin sensitivity in the liver, skeletal muscle and adipose tissue. Malonyl-CoA may also play an important regulatory role in controlling insulin secretion from the pancreas.

Thus, in addition to inhibition of fatty acid synthesis, reduction in malonyl-CoA levels through ACC inhibition may provide a mechanism for increasing fatty acid utilization that may reduce TG rich lipoprotein secretion (VLDL) by the liver, alter insulin secretion by the pancreas, and improve insulin sensitivity in liver, skeletal muscle and adipose tissue.

Also, by increasing fatty acid utilization and by preventing increases in de novo fatty acid synthesis, chronic administration of an ACC-I may also deplete liver and adipose tissue TG stores in obese subjects consuming a low-fat diet, leading to selective loss of body fat.

Therefore a well-tolerated agent that effectively and simultaneously treats the multiple risk factors associated with metabolic syndrome would have a significant impact on the prevention and treatment of the cardiovascular disease associated with obesity, hypertension, diabetes and atherosclerosis.

In mammals, ACC exists as two tissue-specific isozymes, a liver, adipose, and pancreas specific isozyme (ACC1) and a muscle-specific isozyme (ACC2). Inhibition of either isozyme should benefically affect the abnormalities associated with metabiolic syndrome. However, preferably an ACC inhibitor should inhibit both isoforms of the enzyme.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Type 2 diabetes is a severe and prevalent disease in the Western world, that affects roughly 13 million persons in the U.S., along with 5 million presumed to have undiagnosed type 2 diabetes, and another 14 million with impaired glucose tolerance.

Projections indicate that the incidence of type 2 diabetes will increase to over 25 million by 2010 in the U.S., and to over 300 million worldwide by 2025. The annual direct medical cost associated with type 2 diabetes in the United States was 44 billion dollars in 1997, primarily due to the costs of hyperglycemia-related complications, such as retinopathy, nephropathy, peripheral neuropathy, and cardiovascular, peripheral vascular and cerebrovascular disease. Although the causes of type 2 diabetes have not yet been identified, it is well established that it is a polygenic disease characterized by multiple defects in insulin action in muscle, adipose, and liver, and defects in pancreatic insulin secretion. However, the relative importance of each of these defects to the etiology of type 2 diabetes is not clear.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes could be improved. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of Type II diabetes usually consists of a combination of diet, exercise, oral hypoglycemic agents, e.g., thiazolidenediones, and in more severe cases, insulin. However, the clinically available hypoglycemic agents can have side effects that limit their use. In the case of Type I diabetes, insulin is usually the primary course of therapy.

Obesity is a major health risk that leads to increased mortality and incidence of Type 2 diabetes mellitus, hypertension and dyslipidemia. It is the second leading cause of preventable death in the United States, and contributes to >300,000 deaths per year. In the U.S., more than 50% of the adult population is overweight, and almost ¼ of the population is considered to be obese (BMI greater than or equal to 30). Furthermore, the prevalence of obesity in the United States has increased by about 50% in the past 10 years. The prevalence of obesity in adults is 10%–25% in most countries of Western Europe. While the vast majority of obesity occurs in the industrialized world, particularly in US and Europe, the prevalence of obesity is also increasing in Japan. The rise in the incidence of obesity has prompted the WHO to recognize obesity as a significant disease. Two recently marketed anti-obesity agents, Xenical (Orlistat/Roche) and Meridia (Reductil/BASF) exhibit only modest efficacy (Orlistat) and have safety/side effect concerns (Orlistat-gastrointestinal and Meridia-hypertensive effects, respectively), thus limiting their use.

Thus, although there are a variety of anti-atherosclerosis, obesity and diabetes therapies, there is a continuing need and a continuing search in this field of art for alternative therapies.

SUMMARY OF THE INVENTION

This invention is directed to compounds of Formula I

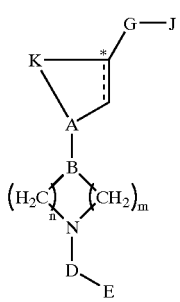

Formula 1 prodrugs thereof, or pharmaceutically acceptable salts of said compounds or of said prodrugs;

wherein A-B is N—CH or CH—N;

K is $(CH_2)r$ wherein r is 2, 3 or 4;

m and n are each independently 1, 2 or 3 when A-B is N—CH or m and n are each independently 2 or 3 when A-B is CH—N;

the dashed line represents the presence of an optional double bond;

D is carbonyl or sulfonyl;

E is either a.) a bicyclic ring consisting of two fused fully unsaturated five to seven membered rings, taken independently, each of said rings optionally having one to four heteroatoms selected independently from oxygen, sulfur and nitrogen, or b.) a tricyclic ring consisting of two fused fully unsaturated five to seven membered rings, taken independently, each of said rings optionally having one to four heteroatoms selected independently from oxygen, sulfur and nitrogen, said two fused rings fused to a third partially saturated, fully unsaturated or fully saturated five to seven membered ring, said third ring optionally having one to four heteroatoms selected independently from oxygen, sulfur and nitrogen; or c.) a tetracyclic ring comprising a bicyclic ring consisting of two fused fully unsaturated five to seven membered rings, taken independently, each of said rings optionally having one to four heteroatoms selected independently from oxygen, sulfur and nitrogen, said bicyclic ring fused to two fully saturated, partially saturated or fully unsaturated five to seven membered monocyclic rings taken independently, each of said rings optionally having one to four heteroatoms selected independently from oxygen, sulfur and nitrogen or said bicyclic ring fused to a second bicyclic ring consisting of two fused fully saturated, partially saturated or fully unsaturated five to seven membered rings, taken independently, each of said rings optionally having one to four heteroatoms selected independently from oxygen, sulfur and nitrogen; or d.) a teraryl ring comprising a fully unsaturated five to seven membered ring, said ring optionally having one to four heteroatoms selected independently from oxygen, sulfur and nitrogen, and said ring di-substituted independently with a fully unsaturated five to seven membered ring to form a teraryl nonfused ring system, each of said substituent rings optionally having one to four heteroatoms selected independently from oxygen, sulfur and nitrogen, wherein said E bi-, tri- or tetra cyclic ring or teraryl ring is optionally mono-, di- or tri-substituted independently on each ring used to form the bi-, tri- or tetra cyclic ring or teraryl ring with halo, hydroxy, amino, cyano, nitro, oxo, carboxy, $(C_1–C_6)$alkyl, $(C_2–C_6)$alkenyl, $(C_2–C_6)$alkynyl, $(C_1–C_6)$alkoxy, $(C_1–C_4)$alkylthio, $(C_1–C_6)$alkoxycarbonyl, $(C_1–C_6)$ alkylcarbonyl, $(C_1–C_6)$alkylcarbonylamino, or mono-N- or di-N,N-$(C_1–C_6)$alkylamino, mono-N- or di-N, N-$(C_1–C_6)$alkylaminocarbonyl wherein said $(C_1–C_6)$alkyl, $(C_1–C_6)$alkoxy and $(C_1–C_4)$alkylthio substituents are also optionally mono-, di- or tri-substituted independently with chloro, bromo, hydroxy, $(C_1–C_6)$alkoxy, amino, mono-N- or di-N,N-$(C_1–C_6)$alkylamino or from one to nine fluorines; and wherein said E bi-, tri- or tetra- cyclic ring or teraryl ring is optionally mono-substituted with a partially saturated, fully saturated or fully unsaturated three to eight membered ring $R^{10}$ optionally having one to four heteroatoms selected independently from oxygen, sulfur and nitrogen or a bicyclic ring $R^{11}$ consisting of two fused partially saturated, fully saturated or fully unsaturated three to eight membered rings, taken independently, each of said rings optionally having one to four heteroatoms selected independently from oxygen, sulfur and nitrogen, said $R^{10}$ and $R^{11}$ rings optionally additionally bridged and said $R^{10}$ and $R^{11}$ rings optionally linked through a fully saturated, partially unsaturated or fully unsaturated one to four membered straight or branched carbon chain wherein the carbon(s) may optionally be replaced with one or two heteroatoms selected independently from oxygen, nitrogen and sulfur, provided said E bicyclic ring has at least one substituent and the E bicyclic ring atom bonded to D is carbon;

wherein said $R^{10}$ or $R^{11}$ ring is optionally mono-, di- or tri-substituted independently with halo, hydroxy, amino, cyano, nitro, oxo, carboxy, $(C_1–C_6)$alkyl, $(C_2–C_6)$alkenyl, $(C_2–C_6)$alkynyl, $(C_1–C_6)$alkoxy, $(C_1–C_4)$alkylthio, $(C_1–C_6)$ alkoxycarbonyl, $(C_1–C_6)$ alkylcarbonyl, $(C_1–C_6)$ alkylcarbonylamino, or mono-N- or di-N,N-$(C_1–C_6)$ alkylamino or mono-N- or di-N,N-$(C_1–C_6)$ alkylaminocarbonyl wherein said $(C_1-C_6)$alkyl and $(C_1-C_6)$ alkoxy substituents are also optionally mono-, di- or tri-substituted independently with halo, hydroxy, $(C_1-C_6)$ alkoxy, amino, mono-N- or di-N,N-$(C_1-C_6)$alkylamino or from one to nine fluorines;

G is carbonyl, sulfonyl or $CR^7R^8$;

wherein $R^7$ and $R^8$ are each independently H, $(C_1-C_6)$ alkyl, $(C_2-C_6)$alkenyl or $(C_2-C_6)$alkynyl or a five to seven membered partially saturated, fully saturated or fully unsaturated ring optionally having one heteroatom selected from oxygen, sulfur and nitrogen;

J is $OR^1$, $NR^2R^3$ or $CR^4R^5R^6$;

wherein $R^1$, $R^2$ and $R^3$ are each independently H, Q, or a $(C_1-C_{10})$alkyl, $(C_3-C_{10})$alkenyl or $(C_3-C_{10})$alkynyl substituent wherein said carbon(s) may optionally be replaced with one or two heteroatoms selected independently from oxygen, nitrogen and sulfur and wherein said sulfur is optionally mono- or di- substituted with oxo, said carbon(s) is optionally mono-substituted with oxo, said nitrogen is optionally di-substituted with oxo, said carbon(s) is optionally mono-, di- or tri-substituted independently with halo, hydroxy, amino, nitro, cyano, carboxy, $(C_1-C_4)$alkylthio, $(C_1-C_6)$alkyloxycarbonyl, mono-N- or di-N,N-$(C_1-C_6)$ alkylamino or mono-N- or di-N,N-$(C_1-C_6)$ alkylaminocarbonyl;

and said chain is optionally mono-substituted with $Q^1$;

wherein Q and $Q^1$ are each independently a partially saturated, fully saturated or fully unsaturated three to eight membered ring optionally having one to three heteroatoms selected independently from oxygen, sulfur and nitrogen or a bicyclic ring consisting of two fused or spirocyclic partially saturated, fully saturated or fully unsaturated three to six membered rings, taken independently, said bicyclic ring optionally having one to three heteroatoms selected independently from oxygen, sulfur and nitrogen, said mono or bicyclic ring optionally additionally bridged with $(C_1-C_3)$ alkylene wherein said $(C_1-C_3)$alkylene carbons are optionally replaced with one to two heteroatoms selected independently from oxygen, sulfur and nitrogen;

wherein said Q and $Q^1$ ring are each independently optionally mono-, di-, tri-, or tetra-substituted independently with halo, hydroxy, amino, nitro, cyano, oxo, carboxy, $(C_1-C_6)$ alkyl, $(C_2-C_6)$alkenyl, $(C_2-C_6)$alkynyl, $(C_1-C_6)$ alkoxy, $(C_1-C_4)$alkylthio, $(C_1-C_6)$ alkylcarbonyl, $(C_1-C_6)$ alkylcarbonylamino, $(C_1-C_6)$alkyloxycarbonyl, mono-N- or di-N,N-$(C_1-C_6)$alkylamino, mono-N- or di-N,N-$(C_1-C_6)$ alkylaminosulfonyl, mono-N- or di-N,N-$(C_1-C_6)$ alkylaminocarbonyl, wherein said $(C_1-C_6)$alkyl substituent is optionally mono-, di- or tri-substituted independently with halo, hydroxy, amino, nitro, cyano, oxo, carboxy, $(C_1-C_6)$ alkoxy, $(C_1-C_4)$alkylthio, $(C_1-C_6)$alkyloxycarbonyl or mono-N- or di-N,N-$(C_1-C_6)$alkylamino wherein said $(C_1-C_6)$alkyl substituent is also optionally substituted with from one to nine fluorines;

or wherein $R^2$ and $R^3$ can be taken together with the nitrogen atom to which they are attached to form a partially saturated, fully saturated or fully unsaturated three to eight membered ring optionally having one to three additional heteroatoms selected independently from oxygen, sulfur and nitrogen or a bicyclic ring consisting of two fused, bridged or spirocyclic partially saturated, fully saturated or fully unsaturated three to six membered rings, taken independently, said bicyclic ring optionally having one to three additional heteroatoms selected independently from oxygen, sulfur and nitrogen or a tricyclic ring consisting of three fused, bridged or spirocyclic partially saturated, fully saturated or fully unsaturated three to six membered rings, taken independently, said tricyclic ring optionally having one to three additional heteroatoms selected independently from oxygen, sulfur and nitrogen;

wherein said $NR^2R^3$ ring is optionally mono-, di-, tri- or tetra-substituted independently with $R^{15}$, halo, hydroxy, amino, nitro, cyano, oxo, carboxy, $(C_1-C_6)$ alkyl, $(C_2-C_6)$ alkenyl, $(C_2-C_6)$alkynyl, $(C_1-C_6)$alkoxy, $(C_1-C_4)$alkylthio, $(C_1-C_6)$alkylcarbonylamino or mono-N- or di-N,N-$(C1-C6)$alkylamino, wherein said $(C_1-C_6)$alkyl substituent is optionally mono-, di- or tri-substituted independently with halo, hydroxy, amino, nitro, cyano, oxo, carboxy, $(C_1-C_6)$ alkoxy, $(C_1-C_4)$alkylthio, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines;

wherein $R^{15}$ is carbonyl, carbamoyl, sulfonyl or sulfamoyl substituted with H, $(C_1-C_6)$alkyl, $(C_1-C_6)$alkyloxy, $(C_1-C_6)$alkyloxycarbonyl, $(C_1-C_6)$alkyloxycarbonyl $(C_1-C_6)$alkyl, mono-N- or di-N,N-$(C_1-C_6)$alkylamino, wherein said $(C_1-C_6)$alkyl substituent is optionally mono-, di- or tri-substituted independently with halo, hydroxy, amino, nitro, cyano, oxo, carboxy, $(C_1-C_6)$alkoxy, $(C_1-C_4)$ alkylthio, $(C_1-C_6)$alkyloxycarbonyl, $(C_1-C_6)$ alkylcarbonyloxy, mono-N- or di-N,N-$(C_1-C_6)$alkylamino or the $R^{15}$ carbonyl, carbamoyl, sulfonyl or sulfamoyl linked substituent is a partially saturated, fully saturated or fully unsaturated three to eight membered ring optionally linked through $(C_1-C_6)$alkyl and optionally having one to three heteroatoms selected independently from oxygen, sulfur and nitrogen wherein said ring is optionally mono-, di- or tri-substituted with halo, hydroxy, amino, nitro, cyano, oxo, carboxy, $(C_1-C_6)$ alkyl, $(C_2-C_6)$alkenyl, $(C_2-C_6)$alkynyl, $(C_1-C_4)$alkylthio, $(C_1-C_6)$alkoxy, $(C_1-C_6)$ alkylcarbonylamino, mono-N- or di-N,N-$(C_1-C_6)$ alkylamino;

wherein said $NR^2R^3$ ring is optionally substituted with a partially saturated, fully saturated or fully unsaturated three to eight membered ring optionally having one to three heteroatoms selected independently from oxygen, sulfur and nitrogen or a bicyclic ring consisting of two fused partially saturated, fully saturated or fully unsaturated three to six membered rings, taken independently, said bicyclic ring optionally having one to three heteroatoms selected independently from oxygen, sulfur and nitrogen, said mono or bicyclic ring optionally additionally bridged said ring optionally having one to three heteroatoms selected independently from oxygen, sulfur and nitrogen, wherein said $(C_1-C_6)$alkyl and said ring are optionally mono-, di- or tri-substituted with halo, hydroxy, amino, nitro, cyano, oxo, carboxy, $(C_2-C_6)$alkenyl, $(C_3-C_6)$alkynyl, $(C_1-C_8)$ alkylcarbonylamino, hydroxy, $(C_1-C_6)$alkoxy, $(C_1-C_4)$ alkylthio, $(C_1-C_6)$alkoxy, mono-N- or di-N,N-$(C_1-C_6)$ alkylamino;

wherein $R^4$, $R^5$ and $R^6$ are independently H, halo, hydroxy, $(C_1-C_6)$alkyl or $R^4$ and $R^5$ are taken together to form a partially saturated, fully saturated or fully unsaturated three to eight membered ring, said ring optionally having one to three heteroatoms selected independently from oxygen, sulfur and nitrogen, wherein said $(C_1-C_6)$alkyl and said ring are optionally mono-, di- or tri-substituted with halo, hydroxy, amino, nitro, cyano, oxo, carboxy, $(C_2-C_6)$ alkenyl, $(C_3-C_6)$alkynyl, $(C_1-C_6)$alkylcarbonylamino, hydroxy, $(C_1-C_6)$alkoxy, $(C_1-C_4)$alkylthio, $(C_1-C_6)$alkoxy, mono-N- or di-N,N-$(C_1-C_6)$alkylamino with the proviso that 1'-(anthracene-9-carbonyl)-[1,4'] bipiperidinyl-3-carboxylic acid diethylamide; 1'-(1-oxa-2,3-diaza-cyclopenta[a]naphthalene-5-sulfonyl)-[1,4']

bipiperidinyl-3 carboxylic acid diethylamide; 1'-(5-dimethylamino-naphthalene-1-sulfonyl)-[1,4']bipiperidinyl-3-carboxylic acid diethylamide; 1'(9,10,10-trioxo-9,10-dihydro-thioxanthene-3-carbonyl)-]1-4']bipiperidinyl-3-carboxylic acid diethylamide; and 1'-(2-Oxo-2H-chromen-3-carbonyl)-[1-4']bipiperidinyl-3-carboxylic acid diethylamide are not included.

A preferred group of compounds, designated the A Group, contains those compounds having the Formula I as shown above wherein A-B is CH—N;

D is carbonyl;

G is carbonyl and the asterisked carbon to which it is attached has R stereochemistry;

m and n are each 1 or 2;

r is 3;

the dashed line is absent;

E is either a. a bicyclic ring consisting of two fused fully unsaturated five to seven membered rings, taken independently, each of said rings optionally having one to four nitrogen atoms; or b. a tricyclic ring consisting of two fused fully unsaturated five to seven membered rings, taken independently, each of said rings optionally having one to two heteroatoms selected independently from oxygen, sulfur and nitrogen, said two fused rings fused to a third partially saturated, fully unsaturated or fully saturated five to seven membered ring, said third ring optionally having one to two heteroatoms selected independently from oxygen, sulfur and nitrogen; or c. a teraryl nonfused ring system comprising a fully unsaturated five to seven membered ring, said ring optionally having one to two heteroatoms selected independently from oxygen, sulfur and nitrogen, and said ring di-substituted independently with a fully unsaturated five to seven membered ring to form a teraryl nonfused ring system, each of said substituent rings optionally having one to two heteroatoms selected independently from oxygen, sulfur and nitrogen, wherein said E bi- or tri- cyclic or teraryl ring is optionally mono-, di- or tri-substituted independently on each ring, used to form the bi- or tri-cyclic or teraryl ring, with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$alkoxy substituents are also optionally mono-, di- or tri-substituted independently with halo, hydroxy or from one to nine fluorines; and wherein said E bi- or tri- cyclic or teraryl ring is optionally mono-substituted with a partially saturated, fully saturated or fully unsaturated five to seven membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, amino, cyano, carboxy, $(C_1-C_6)$alkyl, $(C_2-C_6)$alkenyl, $(C_2-C_6)$alkynyl, $(C_1-C_6)$alkoxy, $(C_1-C_4)$alkylthio, $(C_1-C_6)$alkoxycarbonyl, $(C_1-C_6)$ alkylcarbonyl, $(C_1-C_6)$alkylcarbonylamino, or mono-N- or di-N,N-$(C_1-C_6)$alkylamino or mono-N- or di-N,N-$(C_1-C_6)$alkylaminocarbonyl wherein said $(C_1-C_6)$ alkyl and $(C_1-C_6)$alkoxy substituents are also optionally substituted with from one to nine fluorines;

J is $NR^2R^3$ wherein $R^2$ and $R^3$ can be taken together with the nitrogen atom to which they are attached to form a partially saturated, fully saturated or fully unsaturated five to seven membered ring, optionally having one additional heteroatom selected independently from oxygen, sulfur and nitrogen and said ring optionally bridged with $(C_1-C_3)$alkyl said bridge optionally having one heteroatom selected independently from oxygen, sulfur and nitrogen;

wherein said $NR^2R^3$ ring is optionally mono-, di-, tri- or tetra-substituted independently with halo, hydroxy, amino, cyano, oxo, carboxy, $(C_1-C_6)$ alkyl, $(C_1-C_6)$alkoxy wherein said $(C_1-C_6)$alkyl substituent is optionally mono-, di- or tri-substituted independently with chloro, hydroxy, amino, cyano, oxo, carboxy, $(C_1-C_6)$alkoxy and said,$(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, amino, cyano, carboxy, $(C_1-C_4)$alkylthio, $(C_1-C_6)$ alkyloxycarbonyl, or mono-N- or di-N,N-$(C_1-C_6)$ alkylamino or $Q^1$;

wherein Q and $Q^1$ are each independently a partially saturated, fully saturated or fully unsaturated three to seven membered ring optionally having one to two heteroatoms selected independently from oxygen, sulfur and nitrogen;

wherein said Q and $Q^1$ ring are each independently optionally mono-, di-, tri-, or tetra-substituted independently with halo, hydroxy, amino, cyano, oxo, carboxy, $(C_1-C_6)$ alkyl, $(C_2-C_6)$alkenyl, $(C_3-C_6)$alkynyl, $(C_1-C_6)$alkoxy, $(C_1-C_4)$alkylthio, wherein said $(C_1-C_6)$alkyl substituent is also optionally substituted with from one to nine fluorines or a pharmaceutically acceptable salt thereof.

A group of compounds which is preferred among the A group of compounds, designated the B Group, contains those compounds wherein E is a tricyclic ring, linked through the middle ring, consisting of two fused fully unsaturated six membered rings, taken independently, each of said rings optionally having a nitrogen heteroatom, said two fused rings fused to a third partially saturated or fully unsaturated six membered ring, said third ring optionally having one nitrogen heteroatom; or E is a teraryl ring comprising a fully unsaturated six membered ring, said ring optionally having one nitrogen heteroatom, and said ring di-substituted independently with a fully unsaturated six membered ring to form a teraryl nonfused ring system, each of said substituent rings optionally having one nitrogen heteroatom, wherein said E ring is optionally mono-, di- or tri-substituted independently on each ring used to form the tri-cyclic or teraryl ring with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$ alkoxy substituents are also optionally mono-, di- or tri-substituted independently with halo, hydroxy or from one to nine fluorines; and J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono-, di-, tri- or tetra-substituted independently with halo, hydroxy, amino, oxo, $(C_1-C_6)$ alkyl, $(C_1-C_6)$alkoxy wherein said $(C_1-C_6)$ alkyl substituent is optionally mono-, di- or tri-substituted independently with chloro, hydroxy, oxo, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, $(C_1-C_4)$alkylthio, $(C_1-C_6)$alkyloxycarbonyl, or mono-N- or di-N,N-$(C_1-C_6)$alkylamino or $Q^1$;

wherein Q and $Q^1$ are each independently a partially saturated, fully saturated or fully unsaturated three to seven membered ring optionally having one heteroatom selected independently from oxygen and nitrogen;

wherein said Q and $Q^1$ ring are each independently optionally mono-, di- or tri-substituted independently with halo, hydroxy, oxo, $(C_1-C_6)$ alkyl or $(C_1-C_6)$alkoxy wherein said $(C_1-C_6)$alkyl substituent is also optionally substituted with from one to nine fluorines or a pharmaceutically acceptable salt thereof.

A group of compounds which is preferred among the B group of compounds, designated the C Group, contains those compounds wherein E is a teraryl ring comprising a fully unsaturated six membered ring, said ring optionally having one nitrogen heteroatom, and said ring di-substituted independently with a fully unsaturated six membered ring to form a teraryl nonfused ring system, each of said substituent rings optionally having one nitrogen heteroatom; and wherein said E ring is optionally mono- or di-substituted independently on each ring with halo, $(C_1-C_6)$alkyl or $(C_1-C_6)$alkoxy wherein said $(C_1-C_6)$alkyl and $(C_1-C_6)$ alkoxy substituents are also optionally mono-, di- or tri-substituted independently with halo; and wherein said E ring is mono-substituted with a fully unsaturated six membered ring $R^{10}$ optionally having one heteroatom selected independently from oxygen and nitrogen;

wherein said $R^{10}$ ring is optionally mono- or di-substituted independently on each ring with halo, $(C_1-C_6)$ alkyl or $(C_1-C_6)$alkoxy wherein said $(C_1-C_6)$alkyl and $(C_1-C_6)$alkoxy substituents are also optionally mono-, di- or tri-substituted independently with halo J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono- or di-substituted independently with halo, oxo, $(C_1-C_6)$ alkyl or $(C_1-C_6)$alkoxy wherein said $(C_1-C_6)$alkyl substituent is optionally mono-, di- or tri-substituted independently with oxo, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo or $Q^1$;

wherein Q and $Q^1$ are each independently a fully saturated or fully unsaturated five to six membered ring optionally having one heteroatom selected independently from oxygen and nitrogen;

wherein said Q and $Q^1$ ring are each independently optionally mono- or di-substituted independently with halo, $(C_1-C_6)$ alkyl or $(C_1-C_6)$alkoxy wherein said $(C_1-C_6)$alkyl substituent is also optionally substituted with from one to nine fluorines or a pharmaceutically acceptable salt thereof.

A group of compounds which is preferred among the A group of compounds, designated the D Group, contains those compounds wherein E is a bicyclic ring consisting of two fused fully unsaturated five to seven membered rings, taken independently, each of said rings optionally having one to four nitrogen atoms;

wherein said E ring is optionally mono-, di- or tri-substituted independently on each ring with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$alkoxy substituents are also optionally mono-, di- or tri-substituted independently with halo, hydroxy or from one to nine fluorines; and wherein said E bicyclic ring is mono-substituted with a fully unsaturated five to seven membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$ alkoxy substituents are also optionally mono-, di- or tri-substituted independently with halo, hydroxy or from one to nine fluorines J is $NR^2R^3$ wherein $R^2$ and $R^3$ can be taken together with the nitrogen atom to which they are attached to form a partially saturated or fully saturated five to seven membered ring optionally having one additional heteroatom selected independently from oxygen and nitrogen and said ring optionally bridged with $(C_1-C_3)$alkyl said bridge optionally having one heteroatom selected independently from oxygen, sulfur and nitrogen;

wherein said $NR^2R^3$ ring is optionally mono-, di-, tri- or tetra-substituted independently with halo, hydroxy, amino, cyano, oxo, carboxy, $(C_1-C_6)$ alkyl, $(C_1-C_6)$alkoxy wherein said $(C_1-C_6)$alkyl substituent is optionally mono-, di- or tri-substituted independently with chloro, hydroxy, amino, cyano, oxo, carboxy, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, amino, nitro, cyano, carboxy, $(C_1-C_4)$alkylthio, $(C_1-C_6)$alkyloxycarbonyl, or mono-N- or di-N,N-$(C_1-C_6)$ alkylamino or $Q^1$;

wherein Q and $Q^1$ are each independently a partially saturated, fully saturated or fully unsaturated three to eight membered ring optionally having one to two heteroatoms selected independently from oxygen, sulfur and nitrogen;

wherein said Q and $Q^1$ ring are each independently optionally mono-, di-, tri-, or tetra-substituted independently with halo, hydroxy, amino, cyano, oxo, carboxy, $(C_1-C_6)$ alkyl, $(C_2-C_6)$alkenyl, $(C_3-C_6)$alkynyl, $(C_1-C_6)$alkoxy, $(C_1-C_4)$alkylthio, wherein said $(C_1-C_6)$alkyl substituent is also optionally substituted with from one to nine fluorines or a pharmaceutically acceptable salt thereof.

A group of compounds which is preferred among the D group of compounds, designated the E Group, contains those compounds wherein E is a bicyclic ring consisting of two fused fully unsaturated five to six membered rings, taken independently, each of said rings optionally having one to two nitrogen atoms;

wherein said E ring is optionally mono- or di-substituted independently on each ring with halo, hydroxy, $(C_1-C_6)$ alkyl, $(C_1-C_6)$alkoxy or $(C_1-C_4)$alkylthio wherein said $(C_1-C_6)$alkyl and $(C_1-C_6)$alkoxy substituents are also optionally mono-, di- or tri-substituted independently with halo, hydroxy or from one to nine fluorines; and wherein said E bicyclic ring is mono-substituted with a fully unsaturated five to six membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, $(C_1-C_6)$alkyl, ($C_1$–$C_6$)alkoxy or ($C_1$–$C_4$)alkylthio wherein said ($C_1$–$C_6$) alkyl and ($C_1$–$C_6$)alkoxy substituents are also optionally mono-, di- or tri-substituted independently with halo, hydroxy or from one to nine fluorines J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono-, di-, tri- or tetra-substituted independently with halo, hydroxy, amino, oxo, ($C_1$–$C_6$) alkyl, ($C_1$–$C_6$)alkoxy wherein said ($C_1$–$C_6$) alkyl substituent is optionally mono-, di- or tri-substituted independently with chloro, hydroxy, oxo, ($C_1$–$C_6$)alkoxy and said ($C_1$–$C_6$)alkyl substituent is also optionally substituted with from one to nine fluorines;

or wherein $R^2$ and $R^3$ are each independently H, Q, or ($C_1$–$C_6$) alkyl wherein said ($C_1$–$C_6$)alkyl is optionally mono-, di- or tri-substituted independently with halo, hydroxy, ($C_1$–$C_4$)alkylthio, ($C_1$–$C_6$)alkyloxycarbonyl, or mono-N- or di-N,N-($C_1$–$C_6$)alkylamino or $Q^1$;

wherein Q and $Q^1$ are each independently a partially saturated, fully saturated or fully unsaturated three to seven membered ring optionally having one heteroatom selected independently from oxygen and nitrogen;

wherein said Q and $Q^1$ ring are each independently optionally mono-, di- or tri-substituted independently with halo, hydroxy, oxo, ($C_1$–$C_6$) alkyl or ($C_1$–$C_6$)alkoxy wherein said ($C_1$–$C_6$)alkyl substituent is also optionally substituted with from one to nine fluorines or a pharmaceutically acceptable salt thereof.

A group of compounds which is preferred among the E group of compounds, designated the F Group, contains those compounds wherein E is a bicyclic ring consisting of two fused fully unsaturated six membered rings, taken independently, each of said rings optionally having one nitrogen atom;

wherein said E ring is optionally mono- or di-substituted independently on each ring with halo, ($C_1$–$C_6$)alkyl or ($C_1$–$C_6$)alkoxy wherein said ($C_1$–$C_6$)alkyl and ($C_1$–$C_6$) alkoxy substituents are also optionally mono-, di- or tri-substituted independently with halo; and wherein said E bicyclic ring is mono-substituted with a fully unsaturated six membered ring $R^{10}$ optionally having one heteroatom selected independently from oxygen and nitrogen;

wherein said $R^{10}$ ring is optionally mono- or di-substituted independently on each ring with halo, ($C_1$–$C_6$) alkyl or ($C_1$–$C_6$)alkoxy wherein said ($C_1$–$C_6$)alkyl and ($C_1$–$C_6$)alkoxy substituents are also optionally mono-, di- or tri-substituted independently with halo J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono- or di-substituted independently with halo, oxo, ($C_1$–$C_6$) alkyl or ($C_1$–$C_6$)alkoxy wherein said ($C_1$–$C_6$)alkyl substituent is optionally mono-, di- or tri-substituted independently with oxo, ($C_1$–$C_6$)alkoxy and said ($C_1$–$C_6$)alkyl substituent is also optionally substituted with from one to nine fluorines or a pharmaceutically acceptable salt thereof.

A group of compounds which is preferred among the F group of compounds, designated the G Group, contains those compounds wherein E is a bicyclic ring consisting of two fused fully unsaturated six membered rings, taken independently, each of said rings optionally having one nitrogen atom;

wherein said E ring is optionally mono- or di-substituted independently on each ring with halo, ($C_1$–$C_6$)alkyl or ($C_1$–$C_6$)alkoxy wherein said ($C_1$–$C_6$)alkyl and ($C_1$–$C_6$) alkoxy substituents are also optionally mono-, di- or tri-substituted independently with halo; and wherein said E bicyclic ring is mono-substituted with a fully unsaturated six membered ring $R^{10}$ optionally having one heteroatom selected independently from oxygen and nitrogen;

wherein said $R^{10}$ ring is optionally mono- or di-substituted independently on each ring with halo, ($C_1$–$C_6$) alkyl or ($C_1$–$C_6$)alkoxy wherein said ($C_1$–$C_6$)alkyl and ($C_1$–$C_6$)alkoxy substituents are also optionally mono-, di- or tri-substituted independently with halo J is $NR^2R^3$ wherein $R^2$ and $R^3$ are each independently H, Q, or ($C_1$–$C_6$) alkyl wherein said ($C_1$–$C_6$)alkyl is optionally mono-, di- or tri-substituted independently with halo or $Q^1$;

wherein Q and $Q^1$ are each independently a fully saturated or fully unsaturated five to six membered ring optionally having one heteroatom selected independently from oxygen and nitrogen;

wherein said Q and $Q^1$ ring are each independently optionally mono- or di-substituted independently with halo, ($C_1$–$C_6$) alkyl or ($C_1$–$C_6$)alkoxy wherein said ($C_1$–$C_6$)alkyl substituent is also optionally substituted with from one to nine fluorines or a pharmaceutically acceptable salt thereof.

A preferred group of compounds, designated the H Group, contains those compounds having the Formula I as shown above wherein A-B is CH—N;

D is carbonyl;

G is carbonyl and the asterisked carbon to which it is attached has R stereochemistry;

m and n are each 2;

r is 3;

the dashed line is absent; and

E is a bicyclic ring consisting of two fused fully unsaturated five to seven membered rings, taken independently, each of said rings optionally having one to four nitrogen atoms;

wherein said E ring is optionally mono-, di- or tri-substituted independently on each ring with halo, hydroxy, ($C_1$–$C_6$)alkyl, ($C_1$–$C_6$)alkoxy, ($C_1$–$C_4$)alkylthio, or mono-N- or di-N,N-($C_1$–$C_6$)alkylamino wherein said ($C_1$–$C_6$)alkyl and ($C_1$–$C_6$)alkoxy substituents are also optionally mono-, di- or tri-substituted independently with halo, hydroxy or from one to nine fluorines; and wherein said E bicyclic ring is mono-substituted with a fully unsaturated five to seven membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, ($C_1$–$C_6$)alkyl, ($C_1$–$C_6$)alkoxy, ($C_1$–$C_4$)alkylthio, or mono-N- or di-N,N-($C_1$–$C_6$)alkylamino wherein said ($C_1$–$C_6$)alkyl and ($C_1$–$C_6$) alkoxy substituents are also optionally mono-, di- or tri-substituted independently with halo, hydroxy or from one to nine fluorines or a pharmaceutically acceptable salt thereof.

A group of compounds which is preferred among the H group of compounds, designated the I Group, contains those compounds wherein E is a bicyclic ring consisting of two fused fully unsaturated five to six membered rings, taken independently, each of said rings optionally having one to two nitrogen atoms;

wherein said E ring is optionally mono- or di-substituted independently on each ring with halo, hydroxy, $(C_1-C_6)$ alkyl, $(C_1-C_6)$alkoxy or $(C_1-C_4)$alkylthio wherein said $(C_1-C_6)$alkyl and $(C_1-C_6)$alkoxy substituents are also optionally mono-, di- or tri-substituted independently with halo, hydroxy or from one to nine fluorines; and wherein said E bicyclic ring is mono-substituted with a fully unsaturated five to six membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, $(C_1-C_6)$alkyl, $(C_1-C_6)$alkoxy or $(C_1-C_4)$alkylthio wherein said $(C_1-C_6)$ alkyl and $(C_1-C_6)$alkoxy substituents are also optionally mono-, di- or tri-substituted independently with halo, hydroxy or from one to nine fluorines or a pharmaceutically acceptable salt thereof.

A group of compounds which is preferred among the I group of compounds, designated the J Group, contains those compounds wherein E is a bicyclic ring consisting of two fused fully unsaturated six membered rings, taken independently, each of said rings optionally having one nitrogen atom;

wherein said E ring is optionally mono- or di-substituted independently on each ring with halo, $(C_1-C_6)$alkyl or $(C_1-C_6)$alkoxy wherein said $(C_1-C_6)$alkyl and $(C_1-C_6)$ alkoxy substituents are also optionally mono-, di- or tri-substituted independently with halo; and wherein said E bicyclic ring is mono-substituted with a fully unsaturated six membered ring $R^{10}$ optionally having one heteroatom selected independently from oxygen and nitrogen;

wherein said $R^{10}$ ring is optionally mono- or di-substituted independently on each ring with halo, $(C_1-C_6)$ alkyl or $(C_1-C_6)$alkoxy wherein said $(C_1-C_6)$alkyl and $(C_1-C_6)$alkoxy substituents are also optionally mono-, di- or tri-substituted independently with halo or a pharmaceutically acceptable salt thereof.

A preferred group of compounds, designated the K Group, contains those compounds having the Formula I as shown above wherein A-B is CH—N;

D is carbonyl;

G is carbonyl and the asterisked carbon to which it is attached has R stereochemistry;

m and n are each 2;

r is 3;

the dashed line is absent; and

J is $NR^2R^3$ wherein $R^2$ and $R^3$ can be taken together with the nitrogen atom to which they are attached to form a partially saturated or fully saturated five to seven membered ring optionally having one additional heteroatom selected independently from oxygen and nitrogen and said ring optionally bridged with $(C_1-C_3)$alkyl said bridge optionally having one heteroatom selected independently from oxygen, sulfur and nitrogen;

wherein said $NR^2R^3$ ring is optionally mono-, di-, tri- or tetra-substituted independently with halo, hydroxy, amino, cyano, oxo, carboxy, $(C_1-C_6)$ alkyl, $(C_1-C_6)$alkoxy wherein said $(C_1-C_6)$alkyl substituent is optionally mono-, di- or tri-substituted independently with chloro, hydroxy, amino, cyano, oxo, carboxy, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, amino, nitro, cyano, carboxy, $(C_1-C_4)$alkylthio, $(C_1-C_6)$alkyloxycarbonyl, or mono-N- or di-N,N-$(C_1-C_6)$ alkylamino or $Q^1$;

wherein Q and $Q^1$ are each independently a partially saturated, fully saturated or fully unsaturated three to eight membered ring optionally having one to two heteroatoms selected independently from oxygen, sulfur and nitrogen;

wherein said Q and $Q^1$ ring are each independently optionally mono-, di-, tri-, or tetra-substituted independently with halo, hydroxy, amino, cyano, oxo, carboxy, $(C_1-C_6)$ alkyl, $(C_2-C_6)$alkenyl, $(C_2-C_6)$alkynyl, $(C_1-C_6)$alkoxy, $(C_1-C_4)$alkylthio, wherein said $(C_1-C_6)$alkyl substituent is also optionally substituted with from one to nine fluorines or a pharmaceutically acceptable salt thereof.

A group of compounds which is preferred among the K group of compounds, designated the L Group, contains those compounds wherein J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono-, di-, tri- or tetra-substituted independently with halo, hydroxy, amino, oxo, $(C_1-C_6)$ alkyl, $(C_1-C_6)$alkoxy wherein said $(C_1-C_6)$ alkyl substituent is optionally mono-, di- or tri-substituted independently with chloro, hydroxy, oxo, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, $(C_1-C_4)$alkylthio, $(C_1-C_6)$alkyloxycarbonyl, or mono-N- or di-N,N-$(C_1-C_6)$alkylamino or $Q^1$;

wherein Q and $Q^1$ are each independently a partially saturated, fully saturated or fully unsaturated three to seven membered ring optionally having one heteroatom selected independently from oxygen and nitrogen;

wherein said Q and $Q^1$ ring are each independently optionally mono-, di- or tri-substituted independently with halo, hydroxy, oxo, $(C_1-C_6)$ alkyl or $(C_1-C_6)$alkoxy wherein said $(C_1-C_6)$alkyl substituent is also optionally substituted with from one to nine fluorines or a pharmaceutically acceptable salt thereof.

A group of compounds which is preferred among the L group of compounds, designated the M Group, contains those compounds wherein J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono- or di-substituted independently with halo, oxo, $(C_1-C_6)$ alkyl or $(C_1-C_6)$alkoxy wherein said $(C_1-C_6)$alkyl substituent is optionally mono-, di- or tri-substituted independently with oxo, $(C_1-C_6)$alkoxy and said $(C_1-C_6)$alkyl substituent is also optionally substituted with from one to nine fluorines or a pharmaceutically acceptable salt thereof.

A group of compounds which is preferred among the L group of compounds, designated the N Group, contains those compounds wherein J is $NR^2R^3$ wherein $R^2$ and $R^3$ are each independently H, Q, or $(C_1-C_6)$ alkyl wherein said $(C_1-C_6)$alkyl is optionally mono-, di- or tri-substituted independently with halo or $Q^1$;

wherein Q and $Q^1$ are each independently a fully saturated or fully unsaturated five to six membered ring optionally having one heteroatom selected independently from oxygen and nitrogen;

wherein said Q and $Q^1$ are each independently is optionally mono- or di-substituted independently with halo, $(C_1-C_6)$ alkyl or $(C_1-C_6)$alkoxy wherein said $(C_1-C_6)$alkyl substituent is also optionally substituted with from one to nine fluorines or a pharmaceutically acceptable salt thereof.

A preferred group of compounds, designated the O Group, contains those compounds having the Formula I as shown above wherein E is a bicyclic ring consisting of two fused fully unsaturated five to seven membered rings, taken independently, each of said rings optionally having one to four nitrogen atoms;

wherein said E ring is optionally mono-, di- or tri-substituted independently on each ring with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$alkoxy substituents are also optionally mono-, di- or tri-substituted independently with halo, hydroxy or from one to nine fluorines; and wherein said E bicyclic ring is mono-substituted with a fully unsaturated five to seven membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, $(C_1-C_6)$alkyl, $(C_1-C_6)$alkoxy, $(C_1-C_4)$alkylthio, or mono-N- or di-N,N-$(C_1-C_6)$alkylamino wherein said $(C_1-C_6)$alkyl and $(C_1-C_6)$alkoxy substituents are also optionally mono-, di- or tri-substituted independently with halo, hydroxy or from one to nine fluorines J is $NR^2R^3$ wherein $R^2$ and $R^3$ can be taken together with the nitrogen atom to which they are attached to form a partially saturated or fully saturated five to seven membered ring optionally having one additional heteroatom selected independently from oxygen and nitrogen and said ring optionally bridged with $(C_1-C_3)$alkyl said bridge optionally having one heteroatom selected independently from oxygen, sulfur and nitrogen;

wherein said $NR^2R^3$ ring is optionally mono-, di-, tri- or tetra-substituted independently with halo, hydroxy, amino, cyano, oxo, carboxy, $(C_1-C_6)$ alkyl, $(C_1-C_6)$alkoxy wherein said $(C_1-C_6)$alkyl substituent is optionally mono-, di- or tri-substituted independently with chloro, hydroxy, amino, cyano, oxo, carboxy, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, amino, nitro, cyano, carboxy, $(C_1-C_4)$alkylthio, $(C_1-C_6)$alkyloxycarbonyl, or mono-N- or di-N,N-$(C_1-C_6)$ alkylamino or $Q^1$;

wherein Q and $Q^1$ are each independently a partially saturated, fully saturated or fully unsaturated three to eight membered ring optionally having one to two heteroatoms selected independently from oxygen, sulfur and nitrogen;

wherein said Q and $Q^1$ ring are each independently optionally mono-, di-, tri-, or tetra-substituted independently with halo, hydroxy, amino, cyano, oxo, carboxy, $(C_1-C_6)$ alkyl, $(C_2-C_6)$alkenyl, $(C_2-C_6)$alkynyl, $(C_1-C_6)$alkoxy, $(C_1-C_4)$alkylthio, wherein said $(C_1-C_6)$alkyl substituent is also optionally substituted with from one to nine fluorines or a pharmaceutically acceptable salt thereof.

A group of compounds which is preferred among the O group of compounds, designated the P Group, contains those compounds wherein E is a bicyclic ring consisting of two fused fully unsaturated five to six membered rings, taken independently, each of said rings optionally having one to two nitrogen atoms;

wherein said E ring is optionally mono- or di-substituted independently on each ring with halo, hydroxy, $(C_1-C_6)$ alkyl, $(C_1-C_6)$alkoxy or $(C_1-C_4)$alkylthio wherein said $(C_1-C_6)$alkyl and $(C_1-C_6)$alkoxy substituents are also optionally mono-, di- or tri-substituted independently with halo, hydroxy or from one to nine fluorines; and wherein said E bicyclic ring is mono-substituted with a fully unsaturated five to six membered ring $R^{10}$ optionally having one to two heteroatoms selected independently from oxygen, sulfur and nitrogen;

wherein said $R^{10}$ ring is optionally mono-, di- or tri-substituted independently with halo, hydroxy, $(C_1-C_6)$alkyl, $(C_1-C_6)$alkoxy or $(C_1-C_4)$alkylthio wherein said $(C_1-C_6)$ alkyl and $(C_1-C_6)$alkoxy substituents are also optionally mono-, di- or tri-substituted independently with halo, hydroxy or from one to nine fluorines J is $NR^2R^3$ wherein $R^2$ and $R^3$ can be taken together with the nitrogen atom to which they are attached to form a partially saturated or fully saturated five to six membered ring optionally having one additional heteroatom selected independently from oxygen and nitrogen;

wherein said $NR^2R^3$ ring is optionally mono-, di-, tri- or tetra-substituted independently with halo, hydroxy, amino, oxo, $(C_1-C_6)$ alkyl, $(C_1-C_6)$alkoxy wherein said $(C_1-C_6)$ alkyl substituent is optionally mono-, di- or tri-substituted independently with chloro, hydroxy, oxo, $(C_1-C_6)$alkoxy and said $(C_1-C_6)$alkyl substituent is also optionally substituted with from one to nine fluorines;

or wherein $R^2$ and $R^3$ are each independently H, Q, or $(C_1-C_6)$ alkyl wherein said $(C_1-C_6)$alkyl is optionally mono-, di- or tri-substituted independently with halo, hydroxy, $(C_1-C_4)$alkylthio, $(C_1-C_6)$alkyloxycarbonyl, or mono-N- or di-N,N-$(C_1-C_6)$alkylamino or $Q^1$;

wherein Q and $Q^1$ are each independently a partially saturated, fully saturated or fully unsaturated three to seven membered ring optionally having one heteroatom selected independently from oxygen and nitrogen;

wherein said Q and $Q^1$ ring are each independently optionally mono-, di- or tri-substituted independently with halo, hydroxy, oxo, $(C_1-C_6)$ alkyl or $(C_1-C_6)$alkoxy wherein said $(C_1-C_6)$alkyl substituent is also optionally substituted with from one to nine fluorines or a pharmaceutically acceptable salt thereof.

A preferred group of compounds, designated the Q Group, contains those compounds having the Formula I as shown above wherein a. D is carbonyl;
G is carbonyl;
m and n are each 2;
r is 3;
the dashed line is absent;
A-B is N—CH;
E is 9-anthryl; and
J is morpholino; or
b. D is carbonyl;
G is carbonyl;
m and n are each 2;
r is 3;

the dashed line is absent;
A-B is N—CH;
E is 9-anthryl; and
J is di-N,N isopropylamino; or
c. D is carbonyl;
G is carbonyl;
m and n are each 2;
r is 3;
the dashed line is absent;
A-B is N—CH;
E is 9-anthryl; and
J is 2,2,2,-tri-fluoroethylamino; or
d. D is carbonyl;
G is carbonyl;
m and n are each 2;
r is 3;
the dashed line is absent;
A-B is N—CH;
E is 7-chloro-2-(4-chloro-phenyl)-6-methyl-quinolin-4-yl; and
J is morpholino; or
e. D is carbonyl;
G is carbonyl;
m and n are each 2;
r is 3;
the dashed line is absent;
A-B is N—CH;
E is 9-anthryl; and
J is N-cyclohexyl, N-isopropyl amino; or
f. D is carbonyl;
G is carbonyl;
m and n are each 2;
r is 3;
the dashed line is absent;
A-B is N—CH
E is 9-anthryl; and
J is N-cyclohexyl, N-ethyl amino; or
g. D is carbonyl;
G is carbonyl;
m and n are each 2;
r is 3;
the dashed line is absent;
A-B is N—CH
E is 9-anthryl; and
J is 6-fluoro-2-methyl-3,4-dihydro-2H-quinolin-1-yl; or
h. D is carbonyl;
G is carbonyl;
m and n are each 2;
r is 3;
the dashed line is absent;
A-B is N—CH;
E is 9-anthryl; and
J is N-cyclobutylamino; or
i. D is carbonyl;
G is carbonyl;
m and n are each 2;
r is 3;
the dashed line is absent;
A-B is N—CH;
E is 2,6-diphenyl-pyridin-4-yl; and
J is morpholino; or
j. D is carbonyl;
G is carbonyl;
m and n are each 2;
r is 3;
the dashed line is absent;
A-B is N—CH;
E is 9-anthryl; and
J is 4-dimethylaminocarbonylpiperazino; or
k. D is carbonyl;
G is carbonyl;
m and n are each 2;
r is 3;
the dashed line is absent;
A-B is CH—N
E is 9-anthryl; and
J is morpholino; or
l. D is carbonyl;
G is carbonyl;
m and n are each 2;

r is 3;
the dashed line is absent;
A-B is N—CH;
E is 2,6-diphenyl-pyridin-4-yll; and
J is 2-oxa-5-aza-bicyclol[2.2.1]hept-5-yl; or
m. D is carbonyl;
G is carbonyl;
m and n are each 2;
r is 3;
the dashed line is absent;
A-B is N—CH;
E is 9-anthryl; and
J is 3,5-dimethylmorpholino; or
n. D is carbonyl;
G is carbonyl;
m and n are each 2;
r is 3;
the dashed line is absent;
A-B is N—CH;
E is 9-anthryl; and
J is 3,5-dimethylmorpholino; or
o. D is carbonyl;
G is sulfonyl;
m and n are each 2;
r is 3;
the dashed line is absent;
A-B is N—CH;
E is 9-anthryl; and
J is morpholino; or
p. D is carbonyl;
G is carbonyl;
m and n are each 1;
r is 3;
the dashed line is absent;
A-B is N—CH;
E is 9-anthryl; and
J is morpholino;
or pharmaceutically acceptable salts of said compounds.

A preferred group of compounds are the compounds
(3R)-Anthracen-9-yl-[3-(morpholine-4-carbonyl)-[1,4']bipiperidinyl-1'-yl]-methanone;
(3R)-1'-(Anthracene-9-carbonyl)-[1,4']bipiperidinyl-3-carboxylic acid diisopropylamide;
(3R)-1'-(Anthracene-9-carbonyl)-[1,4']bipiperidinyl-3-carboxylic acid (2,2,2-trifluoro-ethyl)-amide;
(3R)-[7-chloro-2-(4-Chloro-phenyl)-6-methyl-quinolin-4-yl]-[3-(morpholine-4-carbonyl)-[1,4']bipiperidinyl-1'-yl]-methanone;
(3R)-1'-(Anthracene-9-carbonyl)-[1,4']bipiperidinyl-3-carboxylic acid cyclohexyl-isopropyl-amide;
(3R)-1'-(Anthracene-9-carbonyl)-[1,4']bipiperidinyl-3-carboxylic acid cyclohexyl-ethyl-amide;
(3R)-Anthracen-9-yl-[3-(6-fluoro-2-methyl-3,4-dihydro-2H-quinoline-1-carbonyl)-[1,4']bipiperidinyl-1'-yl]-methanone;
(3R)-1'-(Anthracene-9-carbonyl)-[1,4']bipiperidinyl-3-carboxylic acid cyclobutylamide;
(3R)-(2,6-Diphenyl-pyridin-4-yl)-[3-(morpholine-4-carbonyl)-[1,4']bipiperidinyl-1'-yl]-methanone;
(3R)-4-[1'-(Anthracene-9-carbonyl)-[1,4']bipiperidinyl-3-carbonyl]-piperazine-1-carboxylic acid dimethylamide;
(cis-)(1'S,3'R)-anthracen-9-yl-{4-[3-(morpholine-4-carbonyl)-cyclohexyl]-piperazin-1-yl}-methanone;
(3R)-[1'-(2,6-Diphenyl-pyridine-4-carbonyl)-[1,4']bipiperidinyl-3-yl]-(2-oxa-5-aza-bicyclo[2.2.1]hept-5-yl)-methanone;
(3R)-Anthracen-9-yl-[3-(meso-3,5-dimethyl-morpholine-4-carbonyl)-[1,4']bipiperidinyl-1'-yl]-methanone;
(3R)- Anthracen-9-yl-[3-(3R,5R-dimethyl-morpholine-4-carbonyl)-[1,4']bipiperidinyl-1'-yl]-methanone;
Anthracen-9-yl-[3-(morpholine-4-sulfonyl)-[1,4']bipiperidinyl-1'-yl]-methanone (3R)-Anthracen-9-yl-[3-

(3S,5S-dimethyl-morpholine-4-carbonyl)-[1,4']bipiperidinyl-1'-yl]-methanone;
(3R)-Anthracen-9-yl-{3-[3-(morpholine-4-carbonyl)-piperidin-1-yl]-azetidin-1-yl}-methanone;
or pharmaceutically acceptable salts of said compounds.

Another aspect of this invention is directed to methods of treating obesity, an overweight condition, hypertriglyceridemia, hyperlipidemia, hypoalphalipoproteinemia, Metabolic Syndrome, diabetes mellitus (especially Type II), hyperinsulinemia, impaired glucose tolerance, insulin resistance, diabetic complications, atherosclerosis, hypertension, coronary heart disease, hypercholesterolemia, stroke, polycystic ovary disease, cerebrovascular disease or congestive heart failure in a mammal (including a human being) which comprise administering to said mammal a therapeutically effective amount of a compound of Formula I, a prodrug of said compound, or a pharmaceutically acceptable salt of said compound or prodrug.

Yet another aspect of this invention is directed to methods for treating obesity in a mammal (including a human being) by administering to a mammal in need of such treatment an obesity treating amount of a Formula I compound, a prodrug thereof, or a pharmaceutically acceptable salt of said compound or of said prodrug.

Yet another aspect of this invention is directed to methods for inducing weight loss in a mammal (including a human being) by administering to a mammal a therapeutically effective amount of a Formula I compound, a prodrug of thereof, or a pharmaceutically acceptable salt of said compound or of said prodrug.

Yet another aspect of this invention is directed to methods for treating an overweight condition in a mammal (including a human being) by administering to a mammal in need of such treatment an overweight condition treating amount of a Formula I compound, a prodrug thereof, or a pharmaceutically acceptable salt of said compound or of said prodrug.

Yet another aspect of this invention is directed to methods for treating hypertriglyceridemia in a mammal (including a human being) by administering to a mammal in need of such treatment a hypertriglyceridemia treating amount of a Formula I compound, a prodrug thereof, or a pharmaceutically acceptable salt of said compound or of said prodrug.

Yet another aspect of this invention is directed to methods for treating hyperlipidemia in a mammal (including a human being) by administering to a mammal in need of such treatment a hyperlipidemia treating amount of a Formula I compound, a prodrug thereof, or a pharmaceutically acceptable salt of said compound or of said prodrug.

Yet another aspect of this invention is directed to methods for treating hypoalphalipoproteinemia in a mammal (including a human being) by administering to a mammal in need of such treatment a hypoalphalipoproteinemia treating amount of a Formula I compound, a prodrug thereof, or a pharmaceutically acceptable salt of said compound or of said prodrug.

Yet another aspect of this invention is directed to methods for treating Metabolic Syndrome in a mammal (including a human being) by administering to a mammal in need of such treatment a Metabolic Syndrome treating amount of a Formula I compound, a prodrug thereof, or a pharmaceutically acceptable salt of said compound or of said prodrug.

Yet another aspect of this invention is directed to methods for treating diabetes mellitus (Type I or especially Type II) in a mammal (including a human being) by administering to a mammal in need of such treatment a diabetes mellitus treating amount of a Formula I compound, a prodrug thereof, or a pharmaceutically acceptable salt of said compound or of said prodrug.

Yet another aspect of this invention is directed to methods for treating hyperinsulinemia in a mammal (including a human being) by administering to a mammal in need of such treatment a hyperinsulinemia treating amount of a Formula I compound, a prodrug thereof, or a pharmaceutically acceptable salt of said compound or of said prodrug.

Yet another aspect of this invention is directed to methods for treating impaired glucose tolerance in a mammal (including a human being) by administering to a mammal in need of such treatment an impaired glucose tolerance disease treating amount of a Formula I compound, a prodrug thereof, or a pharmaceutically acceptable salt of said compound or of said prodrug.

Yet another aspect of this invention is directed to methods for treating insulin resistance in a mammal (including a human being) by administering to a mammal in need of such treatment an insulin resistance treating amount of a Formula I compound, a prodrug thereof, or a pharmaceutically acceptable salt of said compound or of said prodrug.

Yet another aspect of this invention is directed to methods for treating diabetic complications (e.g., neuropathy, nephropathy, retinopathy or cataracts) in a mammal (including a human being) by administering to a mammal in need of such treatment a diabetic complications treating amount of a Formula I compound, a prodrug thereof, or a pharmaceutically acceptable salt of said compound or of said prodrug.

Yet another aspect of this invention is directed to methods for treating atherosclerosis in a mammal (including a human being) by administering to a mammal in need of such treatment an atherosclerotic treating amount of a Formula I compound, a prodrug thereof, or a pharmaceutically acceptable salt of said compound or of said prodrug.

Yet another aspect of this invention is directed to methods for treating hypertension in a mammal (including a human being) by administering to a mammal in need of such treatment a hypertension treating amount of a Formula I compound, a prodrug thereof, or a pharmaceutically acceptable salt of said compound or of said prodrug.

Yet another aspect of this invention is directed to methods for treating coronary heart disease in a mammal (including a human being) by administering to a mammal in need of such treatment a coronary heart disease treating amount of a Formula I compound, a prodrug thereof, or a pharmaceutically acceptable salt of said compound or of said prodrug.

Yet another aspect of this invention is directed to methods for treating hypercholesterolemia in a mammal (including a human being) by administering to a mammal in need of such treatment a hypercholesterolemia treating amount of a Formula I compound, a prodrug thereof, or a pharmaceutically acceptable salt of said compound or of said prodrug.

Yet another aspect of this invention is directed to methods for treating stroke in a mammal (including a human being) by administering to a mammal in need of such treatment a therapeutically effective amount of a Formula I compound, a prodrug thereof, or a pharmaceutically acceptable salt of said compound or of said prodrug.

Yet another aspect of this invention is directed to methods for treating polycystic ovary disease in a mammal (including a human being) by administering to a mammal in need of such treatment a therapeutically effective amount of a Formula I compound, a prodrug thereof, or a pharmaceutically acceptable salt of said compound or of said prodrug.

Yet another aspect of this invention is directed to methods for treating cerebrovascular disease in a mammal (including a human being) by administering to a mammal in need of such treatment a therapeutically effective amount of a Formula I compound, a prodrug thereof, or a pharmaceutically acceptable salt of said compound or of said prodrug.

Yet another aspect of this invention is directed to methods for treating congestive heart failure in a mammal (including a human being) by administering to a mammal in need of such treatment a congestive heart failure treating amount of a Formula I compound, a prodrug thereof, or a pharmaceutically acceptable salt of said compound or of said prodrug.

Yet another aspect of this invention is directed to methods for treating obesity, an overweight condition, hypertriglyceridemia, hyperlipidemis, hypoalphalipoproteinemia, Metabolic Syndrome, diabetes mellitus, hyperinsulinemia, impaired glucose tolerance, insulin resistance, diabetic complications, atherosclerosis, hypertension, coronary heart disease, hypercholesterolemia, stroke, polycystic ovary disease, cerebrovascular disease or congestive heart failure in a mammal by administering to a mammal in need of such treatment a therapeutically effective amount of 1'-(anthracene-9-carbonyl)-[1,4'] bipiperidinyl-3-carboxylic acid diethylamide or a pharmaceutically acceptable salt of said compound.

Another aspect of this invention is a pharmaceutical composition which comprises 1'-(anthracene-9-carbonyl)-[1,4']bipiperidinyl-3-carboxylic acid diethylamide or a pharmaceutically acceptable salt of said compound and a pharmaceutically acceptable carrier, vehicle or diluent.

A preferred dosage is about 0.001 to about 100 mg/kg/day of a Formula I compound, a prodrug thereof, or a pharmaceutically acceptable salt of said compound or of said prodrug. An especially preferred dosage is about 0.01 to about 10 mg/kg/day of a Formula I compound, a prodrug thereof, or a pharmaceutically acceptable salt of said compound or of said prodrug.

This invention is also directed to pharmaceutical compositions which comprise a compound of Formula I, a prodrug thereof, or a pharmaceutically acceptable salt of said compound or of said prodrug and a pharmaceutically acceptable vehicle, carrier or diluent. Preferably the composition comprises a therapeutically effective amount of the Formula I compound.

This invention is also directed to pharmaceutical compositions for the treatment of obesity, an overweight condition, hypertriglyceridemia, hyperlipidemia, hypoalphalipoproteinemia, Syndrome X, diabetes mellitus (especially Type II), hyperinsulinemia, impaired glucose tolerance, insulin resistance, diabetic complications, atherosclerosis, hypertension, coronary heart disease, hypercholesterolemia, stroke, polycystic ovary disease, cerebrovascular disease or congestive heart failure in a mammal (including a human being) which comprise a therapeutically effective amount of a compound of Formula I, a prodrug thereof, or a pharmaceutically acceptable salt of said compound or of said prodrug and a pharmaceutically acceptable vehicle, diluent or carrier.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second a compound, said second compound being an antiatherosclerosis agent such as lipase inhibitor, an HMG-CoA reductase inhibitor, an HMG-CoA synthase inhibitor, an HMG-CoA reductase gene expression inhibitor, an HMG-CoA synthase gene expression inhibitor, a microsomal triglyceride transfer protein (MTP)/Apo B secretion inhibitor, a cholesterol ester transfer protein (CETP) inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a PPAR agonist, an ion-exchange resin, an antioxidant, an acyl-CoA:cholesterol acyl transferase (ACAT) inhibitor, a bile acid sequestrant, an antiplatelet agent, an antithrombotic agent or an estrogen receptor modulator; and/or optionally a pharmaceutically acceptable vehicle, diluent or carrier.

Preferred among the second compounds are an HMG-CoA reductase inhibitor and a CETP inhibitor.

A particularly preferred HMG-CoA reductase inhibitor is lovastatin, rosuvastatin, itavastatin, simvastatin, pravastatin, fluvastatin, atorvastatin (and its hemicalcium salt) or rivastatin or a pharmaceutically acceptable salt thereof.

Another aspect of this invention is methods for treating atherosclerosis in a mammal comprising administering to a mammal suffering from atherosclerosis a first compound, said first compound being a Formula I compound, a prodrug thereof, or a pharmaceutically acceptable salt of said compound or of said prodrug; and a second compound, said second compound being an antiatherosclerosis agent such as a lipase inhibitor, an HMG-CoA reductase inhibitor, an HMG-CoA synthase inhibitor, an HMG-CoA reductase gene expression inhibitor, an HMG-CoA synthase gene expression inhibitor, a MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a PPAR agonist, an ion-exchange resin, an antioxidant, an ACAT inhibitor, a bile acid sequestrant an antiplatelet agent, an antithrombotic agent, or an and estrogen receptor modulator wherein the amounts of the first and second compounds result in a therapeutic effect.

A preferred aspect of the above methods is wherein the second compound is an HMG-CoA reductase inhibitor or a CETP inhibitor.

A particularly preferred aspect of the above method is wherein the HMG-CoA reductase inhibitor is lovastatin, rosuvastatin, itavastatin, simvastatin, pravastatin, fluvastatin, atorvastatin or rivastatin or a pharmaceutically acceptable salt thereof. Yet another aspect of this invention is kit for achieving a therapeutic effect in a mammal which has been prescribed the joint administration of the active ingredients designated as (a) and (b) below, each active ingredient forming a portion of said kit, comprising in association:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being an antiatherosclerosis agent such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, a PPAR agonist, an ion-exchange resin, an antioxidant, an ACAT inhibitor, a bile acid sequestrant, an antiplatelet agent, an antithrombotic agent or an estrogen receptor modulator; and a pharmaceutically acceptable carrier, vehicle or diluent in a second unit dosage form; and c. directions for the administration of active ingredients (a) and (b) in a manner to achieve a desired therapeutic effect and wherein the amounts of the first and second compounds result in a therapeutic effect.

A preferred second compound is an HMG-CoA reductase inhibitor or a CETP inhibitor.

A particularly preferred HMG-CoA reductase inhibitor is lovastatin, rosuvastatin, itavastatin, simvastatin, pravastatin, fluvastatin, atorvastatin or rivastatin or pharmaceutically acceptable salts thereof.

This invention is also directed to pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being a diabetes treating agent such as aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas, sulfonylureas analogs, biguanides, imidazolines, insulin secretagogues, linogliride, glitazones, glucosidase inhibitors, acarbose, miglitol, emiglitate, voglibose, camiglibose, β-agonists, phosphodiesterase inhibitors (e.g., PDE5 or PDE11), vanadate, vanadium complexes (e.g. Naglivan®), peroxovanadium complexes, amylin antagonists, amylase inhibitors, glucagon antagonists, gluconeogenesis inhibitors, somatostatin analogs, antilipolytic agents, nicotinic acid, acipimox, pramlintide (Symlin™), nateglinide, activators of AMP-activated protein kinase, PPARδ agonists, duel PPARα or/PPAR-δ agonists, protein kinase C-B inhibitors, PTP1B inhibitors, glycogen synthase kinase-3 inhibitors, GLP-1 agonists or soluble guanylate cyclase (sGc) activators; and/or optionally a pharmaceutical vehicle, diluent or carrier.

Preferred among the second compounds are chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

Particularly preferred second compounds are glibenclamide, Glypizide®, glimepiride, repaglinide, metformin or pioglitazone.

Another aspect of this invention is methods for treating diabetes in a mammal comprising administering to a mammal suffering from diabetes a first compound, said first compound being a Formula I compound a prodrug thereof, or a pharmaceutically acceptable salt of said compound or of said prodrug; and a second compound, said second compound being a diabetes treating agent such as aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, α-glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), activators of AMP-activated protein kinase, PPARδ agonists, duel PPARα or /PPAR-δ agonists, protein kinase C-B inhibitors, PTP1B inhibitors, glycogen synthase kinase-3 inhibitors, GLP-1 agonists, soluble guanylate cyclase (sGc) activators or nateglinide wherein the amounts of the first and second compounds result in a therapeutic effect.

A preferred aspect of the above methods is wherein the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particularly preferred aspect of the above methods is wherein the second compound is glibenclamide, Glypizide®, glimepiride, repaglinide, metformin or pioglitazone.

Yet another aspect of this invention is a kit for achieving a therapeutic effect in a mammal which has been prescribed the joint administration of the active ingredients designated as (a) and (b) below, each active ingredient forming a portion of said kit, comprising in association:

a. a first compound, said first compound being a Formula I compound, a prodrug thereof, or a pharmaceutically acceptable salt of said compound or of said prodrug and a pharmaceutically acceptable vehicle, diluent or carrier in a first unit dosage form;

b. a second compound, said second compound being a diabetes treating agent such as aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), nateglinide, activators of AMP-activated protein kinase, PPARδ agonists, duel PPARα or /PPAR-δ agonists, protein kinase C-B inhibitors, PTP1B inhibitors, glycogen synthase kinase-3 inhibitors, GLP-1 agonists or soluble guanylate cyclase (sGc) activators and a pharmaceutically acceptable vehicle, diluent or carrier in a second unit dosage form; and c. directions for the administration of active ingredients (a) and (b) in a manner to achieve a desired therapeutic effect and wherein the amounts of the first and second compounds result in a therapeutic effect.

A preferred second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particularly preferred second compound is glibenclamide, Glypizide®, glimepiride, repaglinide, metformin or pioglitazone.

This invention is also directed to pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being an obesity treating agent such as phenylpropanolamine, ephedrine, pseudoephedrine, phentermine, a neuropeptide Y antagonist, a β-adrenergic receptor agonist, a cholecystokinin-A agonist, a monoamine reuptake inhibitor, a sympathomimetic agent, a serotonin modulator, a dopamine agonist, a melanocortin receptor modulator, a cannabinoid receptor antagonist, a melanin concentrating hormone antagonist, leptin, a leptin analog, a leptin receptor agonist, a galanin antagonist, a lipase inhibitor, a phosphatase 1B inhibitor, a bombesin agonist, dehydroepiandrosternone or analogs thereof, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, an eating behavior modifying agent, a ciliary neurotrophic factor, a neurokinin receptor antagonist, a noradrenalin transport modulator or a dopamine transport modulator; and/or optionally a pharmaceutical vehicle, diluent or carrier.

Preferred among the second compounds are orlistat, sibutramine or bromocriptine.

Another aspect of this invention is s method for treating obesity in a mammal comprising administering to a mammal suffering from obesity a first compound, said first compound being a Formula I compound a prodrug thereof, or a pharmaceutically acceptable salt of said compound or of said prodrug; and a second compound, said second compound being an obesity treating agent such as phenylpropanolamine, ephedrine, pseudoephedrine, phentermine, a neuropeptide Y antagonist, a β-adrenergic receptor agonist, a cholecystokinin-A agonist, a monoamine reuptake inhibitor, a sympathomimetic agent, a serotonin modulator, a dopamine agonist, a melanocortin receptor modulator, a cannabinoid receptor antagonist, a melanin concentrating hormone antagonist, leptin, a leptin analog, a leptin receptor agonist, a galanin antagonist, a lipase inhibitor, a phosphatase 1B inhibitor, a bombesin agonist, dehydroepiandrosternone or analogs thereof, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, an eating behavior modifying agent, a ciliary neurotrophic factor, a neurokinin receptor antagonist, a noradrenalin transport modulator or a dopamine transport modulator; wherein the amounts of the first and second compounds result in a therapeutic effect.

A preferred aspect of the above methods is wherein the second compound is orlistat, sibutramine or bromocriptine.

Yet another aspect of this invention is a kit for achieving a therapeutic effect in a mammal which has been prescribed the joint administration of the active ingredients designated as (a) and (b) below, each active ingredient forming a portion of said kit, comprising in association:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being an obesity treating agent such as phenylpropanolamine, ephedrine, pseudoephedrine, phentermine, a neuropeptide Y antagonist, a β-adrenergic receptor agonist, a cholecystokinin-A agonist, a monoamine reuptake inhibitor, a sympathomimetic agent, a serotonin modulator, a dopamine agonist, a melanocortin receptor modulator, a cannabinoid receptor antagonist, a melanin concentrating hormone antagonist, leptin, a leptin analog, a leptin receptor agonist, a galanin antagonist, a lipase inhibitor, a phosphatase 1B inhibitor, a bombesin agonist, dehydroepiandrosternone or analogs thereof, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, an eating behavior modifying agent, a ciliary neurotrophic factor, a neurokinin receptor antagonist, a noradrenalin transport modulator or a dopamine transport modulator; or a pharmaceutically acceptable vehicle, diluent or carrier in a second unit dosage form; and c. directions for the administration of active ingredients (a) and (b) in a manner to achieve a desired therapeutic effect and wherein the amounts of the first and second compounds result in a therapeutic effect.

A preferred second compound is orlistat, sibutramine or bromocriptine.

This invention is also directed to pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being a cardiovascular agent; and/or optionally a pharmaceutical vehicle, diluent or carrier.

Preferred anti-hypertensive agents are a calcium channel blocker, an angiotensin converting enzyme (ACE) inhibitor or a diuretic.

Another aspect of this invention is a method for treating cardiovascular disease/conditions in a mammal comprising administering to a mammal a first compound, said first compound being a Formula I compound a prodrug thereof, or a pharmaceutically acceptable salt of said compound or of said prodrug; and a second compound, said second compound being a cardiovascular agent wherein the amounts of the first and second compounds result in a therapeutic effect.

Preferred anti-hypertensive agents are a calcium channel blocker, an angiotensin converting enzyme (ACE) inhibitor or a diuretic.

Yet another aspect of this invention is a kit for achieving a therapeutic effect in a mammal which has been prescribed the joint administration of the active ingredients as (a) and (b) below, each active ingredient forming a portion of said kit, comprising in association:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being a cardiovascular agent and a pharmaceutically acceptable vehicle, diluent or carrier in a second unit dosage form; and c. directions for the administration of active ingredients (a) and (b) in a manner to achieve a desired therapeutic effect and wherein the amounts of the first and second compounds result in a therapeutic effect.

Preferred anti-hypertensive agents are a calcium channel blocker, an angiotensin converting enzyme (ACE) inhibitor or a diuretic.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

Metabolic Syndrome (also known as Syndrome X or insulin resistant syndrome) refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

The expression "prodrug" refers to compounds that are drug precursors which, following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

The following paragraphs describe exemplary ring(s) for the generic ring descriptions contained herein.

Exemplary five to six membered aromatic heterocyclic rings include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered heterocyclic rings include cyclopentyl, cyclohexyl, cycloheptyl, cyclooctyl and phenyl. Further exemplary five membered rings include 2H-pyrrolyl, 3H-pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings include azepinyl, oxepinyl, and thiepinyl.

Further exemplary eight membered rings include cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen include indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, 7-bicyclo[4.2.0]octa-1,3,5-trienyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene).

By halo is meant chloro, bromo, iodo, or fluoro.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture thereof which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

The subject invention also includes isotopically-labeled compounds, which are structurally identical to those disclosed herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine and chlorine, such as $^2H$ $^3H$, $^{13}C$, $^{14}C$, $^{15}N$, $^{18}O$, $^{17}O$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

All patents and patent applications referred to herein are hereby incorporated by reference.

DTT means dithiothreitol. DMSO means dimethyl sulfoxide. EDTA means ethylenediamine tetraacetic acid.

Other features and advantages of this invention will be apparent from this description and the appendant claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes are described in the experimental section.

Scheme 1

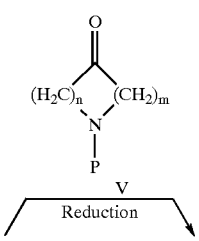

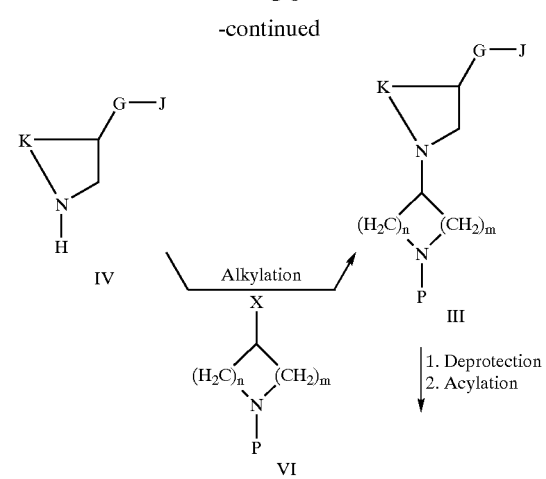

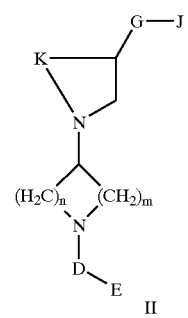

Scheme 2

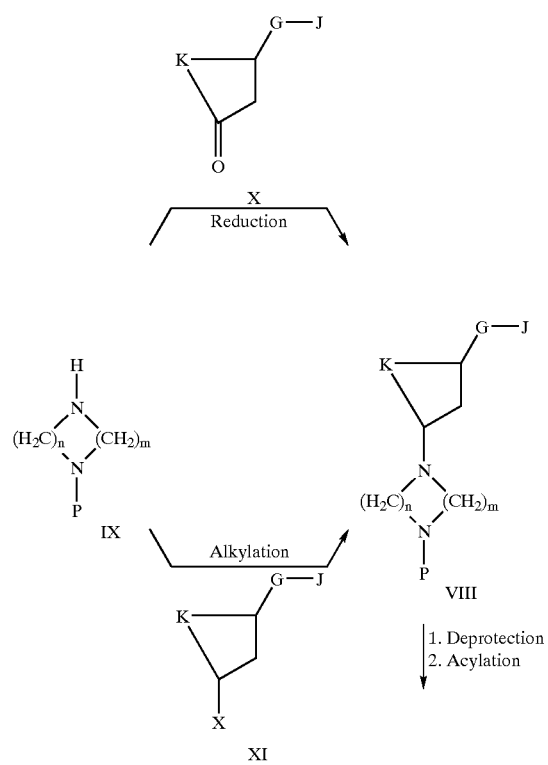

-continued

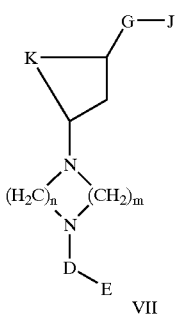

VII preparation methods. The need for such protection is readily determined by one skilled in the art. The use of such protection/deprotection methods is also within the skill in the art. For a general description of protecting groups and their use, see T. W. Greene and P. G. M. Wuts, *Protective Groups in Organic Synthesis*, John Wiley & Sons, New York, 1991.

For example, in Reaction Schemes I and II certain Formula I compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly Scheme 3

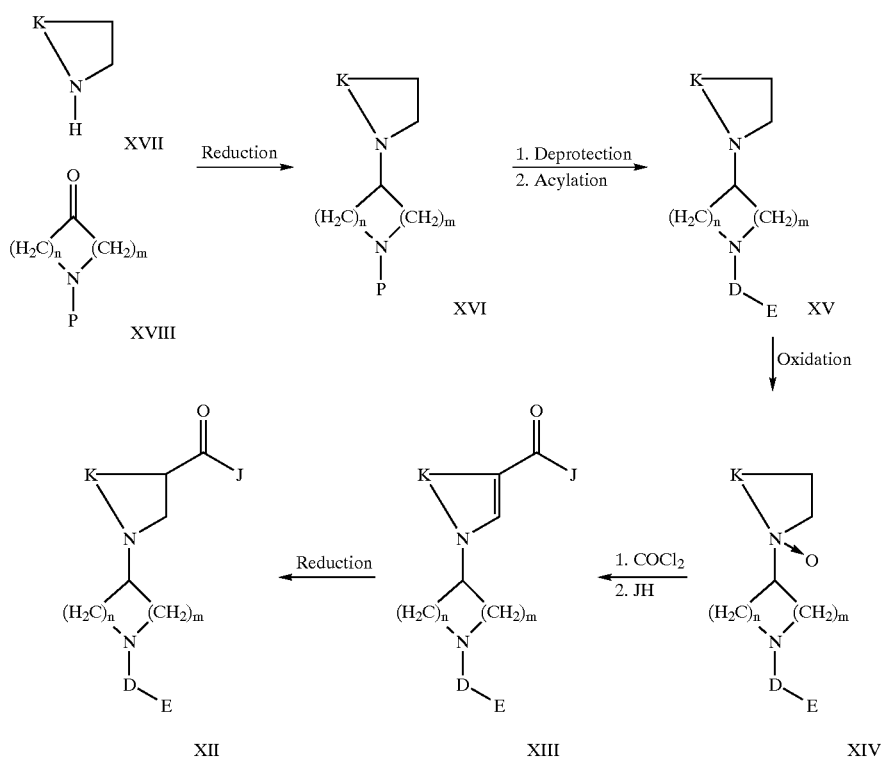

The Reaction Schemes described herein are intended to provide a general description of the methodology employed in the preparation of many of the Examples given. However it will be evident from the detailed descriptions given in the Experimental section that the modes of preparation employed extend further than the general procedures described here. In particular it is noted that the compounds prepared according to these Schemes may be modified further to provide new Examples within the scope of this invention. For example an ester functionality may be reacted further using procedures well known to those skilled in the art to give another ester, an amide, a carbinol or a ketone.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

According to reaction Scheme 1 the desired Formula I compounds wherein A-B is N—CH; D, E, G, J, K, m and n are as described above and the bond represented by a dashed line is absent (depicted as Formula II compounds) may be prepared from the corresponding Formula III compounds by removal of the protecting group P. If the protecting group is benzyl (Bn), benzhydryl (diphenylmethyl) or benzyloxycarbonyl (Z), this may alternatively be removed by hydrogenation in a reaction inert solvent such as methanol, ethanol or acetic acid with a catalyst such as palladium or rhodium on carbon under a hydrogen pressure equal to about 15 to 50 p.s.i. for a period of about 2 to 24 hours, or by transfer hydrogenation using ammonium formate in refluxing methanol in the presence of a catalyst such as palladium on carbon in a reaction inert solvent such as methanol or ethanol at a temperature between about 0° C. to 80° C., typically about 25° C. to 60° C. Alternatively the protecting group (e.g., benzyloxycarbonyl) may be removed by treatment with hydrogen bromide in acetic acid at a temperature between about 0° C. to 60° C., typically ambient, for a period of about 1 to 24 hours. Alternatively the benzyl or diphenylmethyl group may be removed by treatment with 1-Chloroethyl chloroformate in a reaction inert solvent such as 1,2-dichloroethane at a temperature between about 25° C. to 60° C., typically at reflux followed by heating with methanol.

Alternatively the benzyl or diphenylmethyl group may be removed by treatment with 2,2,2-trichloroethyl chloroformate in a reaction inert solvent such as acetonitrile at a temperature between about 25° C. to 60° C., typically ambient followed by heating with zinc in ethanol. If the protecting group is t-butoxycarbonyl (BOC), this may be removed by treatment with trifluoroacetic acid in a solvent such as methylene chloride at a temperature between about 0° C. to 30° C., typically ambient, for a period of about 10 minutes to 3 hours. Alternatively the BOC group may be removed by treatment with hydrogen chloride in a reaction inert solvent such as ethyl acetate, diethyl ether or dioxane at a temperature between about −78° C. to 25° C. for a period of about 10 minutes to 24 hours. Many other suitable protecting groups and means for their removal are described in T. W. Greene and P. G. M. Wuts, *Protective Groups in Organic Synthesis*, John Wiley and Sons, New York, 1991.

Following removal of the protecting group the amine may be combined with the appropriate acyl chloride, acyl anhydride or sulfonyl chloride in a suitable reaction inert solvent such as methylene chloride or chloroform containing a suitable base such as triethylamine or N,N-diisopropylethylamine at a temperature of about 25° C. to about 60° C., typically ambient to provide the desired product of Formula II. Alternatively the amine can combined with a carboxylic acid in the presence of a suitable coupling agent such as benzotriazo-1-yloxytris(dimethylamino)phosphonium hexafluorophosphate (BOP), 1-ethyl-3-(3'-dimethylaminopropyl)carbodiimide hydrochloride (EDCI), 3-(diethoxyphosphoryloxy)-1,2,3-benzotriazin-4(3H)-one (DEPBT) or O-benzotriazol-1-yl-N,N,N',N'-tetramethyluronium hexafluorophosphate (HBTU) in the presence of a suitable base such as triethylamine or N,N-diisopropylethylamine in a suitable reaction inert solvent such as methylene chloride or chloroform at a temperature of about 25° C. to about 60° C., typically ambient to provide the desired product of Formula II.

The desired Formula III compounds wherein D, E, G, J, K, m and n are as described above and P is a known amine protecting group may be prepared by reductive coupling of an amine of Formula IV wherein G, J and K are as described above with a ketone of Formula V, wherein P, n and m are as described above, using a borohydride-type reducing agent such as sodium borohydride, sodium cyanoborohydride or sodium triacetoxyborohydride in a reaction-inert solvent such as tetrahydrofuran, methanol or ethanol at a temperature between about 0° C. to 50° C., typically ambient, for a period of about 1 to 24 hours to provide the desired product of Formula III. Particularly suitable conditions are described by R. J. Mattson et al in *Journal of Organic Chemistry*, 1989, 55, 2552 wherein the reductive alkylation is assisted by pretreating the mixture of amine and ketone with titanium tetraisopropoxide for about 1 hour prior to addition of sodium cyanoborohydride in ethanol. Under these conditions, when G-K represents an ester functionality, there is a tendency for the ester to undergo a degree of transesterification to produce an isopropyl ester. Typically this does not adversely effect the outcome of the subsequent steps. When K is ethoxy the titanium tetraisopropoxide may be replaced with titanium tetraethoxide to avoid this issue. In some cases the protecting group P may advantageously be the group D-E in which case the reductive alkylation provides the desired Formula II compounds directly. When K is not missing the R enantiomer of the compounds of Formula IV are preferred.

In another aspect of Scheme 1 the desired Formula III compounds wherein D, E, G, J, K, m and n are as described above and P is a known amine protecting group may be prepared from an amine of Formula IV wherein G, J and K are as described above and a compound of Formula VI wherein n and m are as described above, P is a suitable amine protecting group (preferably benzyl or diphenylmethyl) and X represents a leaving group exemplified by but not restricted to methanesulfonyl, p-toluenesulfonyl or bromo. The compounds of Formula IV and VI are mixed in a reaction inert solvent such as dimethylformamide or N-methylpyrrolidinone at a temperature between about 25° C. to about 140° C., typically about 110° C., for a period of about 1 to 24 hours to provide the desired product of Formula III.

When n is not equal to m the compounds of Formula II and III are typically prepared as a mixture of diastereoisomers.

According to reaction Scheme 2 the desired Formula I compounds wherein A-B is CH—N; D, E, G, J, K, m and n are as described above and the bond represented by a dashed line is absent (depicted as Formula VII compounds) may be prepared from the corresponding Formula VIII compounds by removal of the protecting group P followed by acylation as described above for the preparation of the compounds of Formula II from the compounds of Formula III.

The desired Formula VIII compounds wherein G, J, K, m and n are as described above and P is a known amine protecting group may be prepared by reductive coupling of an amine of Formula IX wherein n and m are as described above with a ketone of Formula X wherein G, J and K are as described above using a procedure analogous to that used for the preparation of the compounds of Formula III from the compounds of Formula IV and V. In some cases the protecting group P may advantageously be the group D-E in which case the reductive alkylation provides the desired Formula VII compounds directly.

In another aspect of Scheme 2 the desired Formula VIII compounds wherein G, J, K, m and n are as described above and P is a known amine protecting group may be prepared from an amine of Formula IX wherein m, n and P are as described above and a ketone of Formula X wherein G, J and K are as described above using a procedure analogous to that used for the preparation of the compounds of Formula III from the compounds of Formula IV and VI. In some cases the protecting group P may advantageously be the group D-E in which case the reaction provides the desired Formula VII compounds directly.

The compounds of Formula VII and VIII are typically prepared as a mixture of diastereoisomers.

According to reaction Scheme 3 the desired Formula I compounds wherein A-B is N—CH; G is CO; D, E, m, n and K are as described above, J is $OR^1$ or $NR^2R^3$ where $R^1$, $R^2$ and $R^3$ are as described above and the bond represented by a dashed line is present (depicted as Formula XIII compounds) may be prepared from the corresponding Formula XIV compounds by reaction with carbonyl chloride (phosgene) in a reaction inert solvent such as dichloromethane in the presence of a base such as N,N-diisopropylethylamine at about −78° C. for a period of about 1 to 3 hours, typically 2 hours, followed by brief warming to ambient temperature before addition of the appropriate nucleophile JH to give the desired Formula XIII compounds.

The desired Formula XII compounds wherein D, E, J, m, n and K are as described above may be prepared from the corresponding Formula XIII compounds by catalytic hydrogenation in a reaction inert solvent such as methanol, ethanol or acetic acid with a catalyst such as palladium on carbon under a hydrogen pressure equal to about 15 to 50 p.s.i. for a period of about 2 to 72 hours. Alternatively, such compounds may be prepared by transfer hydrogenation using ammonium formate in refluxing methanol in the presence of a catalyst such as palladium on carbon in a reaction inert solvent such as methanol or ethanol at a temperature between about 0° C. to about 80° C., typically about 25° C. to about 60° C. to give the desired Formula XII compounds. When m is not equal to n the Formula XII are typically obtained as a mixture of diastereoisomers all of which are intended to be within the scope of this Invention.

The desired Formula XIV compounds wherein D, E, m, n and K are as described above may be prepared from the corresponding Formula XV compounds by oxidation with a suitable oxidizing agent such as metachlorperbenzoic acid in a reaction inert solvent such as dichloromethane at a temperature between about −78° C. to about 25° C. to give the desired Formula XIV compounds.

The desired Formula XV compounds wherein D, E, m, n and K are as described above may be prepared from the corresponding Formula XVI compounds by a deprotection and acylation procedure analogous to that described for the preparation of the compounds of Formula II from the compounds of Formula Ill. The desired Formula XVI compounds wherein m, n and K are as described above and P is a suitable amine protecting group may be prepared from the corresponding cyclic amine of Formula XVII and ketone of Formula XVIII compounds by a procedure analogous to that described for the preparation of the compounds of Formula III from the compounds of Formulas IV and V. In some cases the protecting group P may advantageously be the group D-E in which case the reaction provides the desired Formula XV compounds directly.

Prodrugs of the compounds of Formula I may be prepared according to methods analogous to those known to those skilled in the art. Exemplary processes are described below.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0° C. to 100° C. for about 1 to 24 hours. Alternatively, the acid is combined with appropriate alcohol as solvent in the presence of a catalytic amount of acid such as concentrated sulfuric acid at a temperature of about 20° C. to 100° C., preferably at a reflux, for about 1 hour to 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0° C. to 100° C. for about 1 to 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides and N-(1-hydroxy-1-(alkoxycarbonyl)methyl) amides may be prepared by the reaction of the parent amide with the appropriate aldehyde under neutral or basic conditions (e.g., sodium ethoxide in ethanol) at temperatures between about 25° C. and 70° C. N-alkoxymethyl or N-1-(alkoxy)alkyl derivatives can be obtained by reaction of the N-unsubstituted compound with the necessary alkyl halide in the presence of a base in an inert solvent.

The compounds of this invention may also be used in conjunction with other pharmaceutical agents for the treatment of the diseases/conditions described herein, as described hereinabove and below. In combination therapy treatment, both the compounds of this invention and the other drug therapies are administered to mammals (e.g., humans, male or female) by conventional methods. Any antiatherosclerosis agent may be used as the second compound in the combination aspect of this invention. Such agents include the classes of anti-atherosclerotic agents (and specific agents) described above in the Summary of the Invention and herein below. For example, they may be used in combination with cholesterol synthesis inhibitors, fibrates, niacin, garlic extract, ion-exchange resins, antioxidants and bile acid sequestrants.

Any cholesterol absorption inhibitor may be used as the second compound in the combination aspect of this invention. The term cholesterol absorption inhibition refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (e.g., J. Lipid Res. (1993) 34: 377–395). Cholesterol absorption inhibitors are known to those skilled in the art and are described, for example, in PCT WO 94/00480.

Any HMG-CoA reductase inhibitor may be used as the second compound in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below however other HMG- CoA reductase inhibitors will be known to those skilled in the art. U.S. Pat. No. 4,231,938 discloses certain compounds isolated after cultivation of a microorganism belonging to the genus *Aspergillus*, such as lovastatin. Also, U.S. Pat. No. 4,444,784 discloses synthetic derivatives of the aforementioned compounds, such as simvastatin. Also, U.S. Pat. No. 4,739,073 discloses certain substituted indoles, such as fluvastatin. Also, U.S. Pat. No. 4,346,227 discloses ML-236B derivatives, such as pravastatin. Also, EP-491226A discloses certain pyridyldihydroxyheptenoic acids, such as rivastatin. In addition, U.S. Pat. No. 5,273,995 discloses certain 6-[2-(substituted-pyrrol-1-yl)alkyl]pyran-2-ones such as atorvastatin and the hemicalcium salt thereof (Lipitor®). Additional HMG-CoA reductase inhibitors include rosuvastatin, itavostatin and cerivastatin.

Any MTP/Apo B secretion (microsomal triglyceride transfer protein and/or apolipoprotein B secretion) inhibitor may be used as the second compound in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are known to those skilled in the art, including those disclosed in WO 96/40640 and WO 98/23593.

Any HMG-CoA synthase inhibitor (or HMG-CoA synthase gene expression inhibitor) may be used as the second compound in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (e.g., Meth. Enzymol. 1985; 110:9–19). Inhibitors of HMG-CoA reductase gene expression will be known to those skilled in the art, for example, U.S. Pat. No. 5,041,432 discloses certain 15-substituted lanosterol derivatives. Other oxygenated sterols that suppress synthesis of HMG-CoA reductase are discussed by E. I. Mercer (Prog.Lip. Res. 1993;32:357–416).

Any compound having activity as a CETP inhibitor can serve as the second compound in the combination therapy aspect of the instant invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned allowed U.S. application Ser. No. 09/391,152. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively.

Any squalene synthetase inhibitor may be used as the second compound of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (e.g., Meth. Enzymol. 1969; 15: 393–454 and Meth. Enzymol. 1985; 110:359–373 and references contained therein). A variety of these compounds are known to those skilled in the art, for example, U.S. Pat. No. 5,026,554 discloses fermentation products of the microorganism MF5465 (ATCC 74011) including zaragozic acid. A summary of other squalene synthetase inhibitors has been compiled (Curr. Op. Ther. Patents (1993) 861–4).

Any squalene epoxidase inhibitor may be used as the second compound in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., Biochim. Biophys. Acta 1984; 794:466–471). A variety of these compounds are known to those skilled in the art, for example, U.S. Pat. Nos. 5,011,859 and 5,064,864 disclose certain fluoro analogs of squalene. EP publication 395,768 A discloses certain substituted allylamine derivatives. PCT publication WO 9312069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (e.g., FEBS Lett. 1989;244:347–350). Squalene cyclase inhibitors are known to those skilled in the art. For example, PCT publication W09410150 and French patent publication 2697250 disclose squalene cyclase inhibitors.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors. However, these assays are recognized by those skilled in the art. Thus, inhibition by combined squalene epoxidase/ squalene cyclase inhibitors is readily determined by those skilled in art according to the aforementioned standard assays for squalene cyclase or squalene epoxidase inhibitors. A variety of squalene epoxidase/squalene cyclase inhibitors are known to those skilled in the art. U.S. Pat. Nos. 5,084,461 and 5,278,171 disclose certain azadecalin derivatives. EP publication 468,434 discloses certain piperidyl ether and thio-ether derivatives such as 2-(1-piperidyl)pentyl isopentyl sulfoxide and 2-(1-piperidyl)ethyl ethyl sulfide. PCT publication WO 9401404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

Any ACAT inhibitor can serve as the second compound in the combination therapy aspect of this invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity.

Any PPAR agonist may be used as the second compound in the combination aspect of this invention. The term agonist refers to agents that activate peroxisome proliferator activator receptor activity in mammals, particularly humans. Thus, it is believed that such compounds, by activating the PPAR receptor stimulate transcription of key genes involved in fatty acid oxidation and also those involved in high density lipoprotein (HDL) assembly (for increasing HDL cholesterol). Particular agonists are PPAR-α agonist and a suitable PPAR-α agonist is, e.g., fenofibrate. Other exemplary compounds include those disclosed in commonly assigned U.S. provisional application Ser. No. 60/269,057 filed Feb. 15, 2001 and commonly assigned U.S. provisional application Ser. No. 60/269,058 filed Feb. 15, 2001.

Any antiplatelet and antithrombotic agent may be used as the second compound in the combination aspect of this invention. Suitable antiplatelet and antithrombotic agents include, e.g., tPA, uPA, warfarin, hirudin and other thrombin inhibitors, heparin and thromboplastin activating factor inhibitors.

Any estrogen receptor modulator, estrogen agonist or estrogen antagonist may be used as the second compound in the combination aspect of this invention. Such compounds are known to mediate lipid levels. Suitable estrogen receptor modulators, estrogen agonists or estrogen antagonists include the compounds disclosed in International Patent Application Publication No. WO96/21656 and U.S. Pat. No. 5,552,412. Preferred such compounds include raloxifene, lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof.

Any lipase inhibitor maybe used as the second compound in the combination aspect of this invention. A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286: 190–231).

Any pancreataic lipase inhibitor may be used as the second compound in the combination aspect of this invention. Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides. Such pancreatic lipase inhibition activity is readily determined by those skilled in the art according to standard assays (e.g., Methods Enzymol. 286: 190–231).

Any gastric lipase inhibitor may be used as the second compound in the combination aspect of this invention. Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987). Such gastric lipase inhibition activity is readily determined by those skilled in the art according to standard assays (e.g., Methods Enzymol. 286: 190–231).

A variety of lipase inhibitors are known to one of ordinary skill in the art. Preferred gastric and/or pancreatic lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949).

A variety of pancreatic lipase inhibitors are described herein below. The pancreatic lipase inhibitors lipstatin, (2S,3S,5S,7Z,1 OZ)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl) cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., *J. Antibiotics,* 40 (11), 1647–1650 (1987). The pancreatic lipase inhibitors, ebelactone A and ebelactone B, and a process for the preparation thereof by the microbial cultivation of *Actinomycetes* strain MG7-G1, are disclosed in Umezawa, et al., *J. Antibiotics,* 33,1594–1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, or the like, or any of the diabetic complications such as neuropathy, nephropathy, retinopathy or cataracts, a therapeutically effective amount of a Formula I compound in combination with other agents (e.g., insulin) that can be used to treat diabetes. Such agents include the classes of anti-diabetic agents (and specific agents) described above in the Summary of the Invention and herein below.

Any glycogen phosphorylase inhibitor may be used as the second agent in combination with a Formula I compound. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934–2938). A variety of glycogen phosphorylase inhibitors are known to those skilled in the art including those described in WO 96/39384 and WO 96/39385.

Any aldose reductase inhibitor may be used in a combination with a Formula I compound. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, *Diabetes,* 29:861–864 (1980). "Red Cell Sorbitol, an Indicator of Diabetic Control"). A variety of aldose reductase inhibitors are known to those skilled in the art such as zopolrestat, epalrestat, ponalrestat, zenarestat and fidarestat.

Any sorbitol dehydrogenase inhibitor may be used in combination with a Formula I compound. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329–331). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase. Other SDIs include those dislcosed in International Patent Application Publication No. WO00/59510. A particuarly preferred SDI is 1R-(4-(4-(4,6-dimethyl)-[1,3,5]triazin-2-yl)-2R,6S-dimethyl-piperazin-1-yl)-pyrimidin-2-yl)-ethanol.

Any glucosidase inhibitor may be used in combination with a Formula I compound. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor comprises an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634, 765. The glucosidase inhibitor, camiglibose, methyl 6-deoxy-6-[(2R,3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

Any amylse inhibitor may be used in combination with a Formula I compound. A variety of amylase inhibitors are known to one of ordinary skill in the art. The amylase inhibitor, tendamistat and the various cyclic peptides related thereto, are disclosed in U.S. Pat. No. 4,451,455. The amylase inhibitor Al-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Any PDE5 or PDE11 inhibitor may be used as the second compound of a combination of this invention. It is particularly preferred that a PDE5 inhibitor be used as the second compound of this invention. Suitable PDE5 inhibitors include the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in International Patent Application Publication No. WO93/07149; the quinazolin-4-ones disclosed in International Patent Application Publication No. WO93/12095; the pyrido [3,2-d]pyrimidin-4-ones disclosed in International Patent Application Publication No. WO94/05661; the purin-6-ones disclosed in International Patent Application Publication No. WO94/00453; the pyrazolo [4,3-d]pyrimidin-7-ones disclosed in International Patent Application Publication No. WO98/49166; the pyrazolo [4,3-d]pyrimidin-7-ones disclosed in International Patent Application Publication No. WO99/54333; the pyrazolo [4,3-d]pyrimidin-4-ones disclosed in EP-A-0995751; the pyrazolo [4,3-d]pyrimidin-7-ones disclosed in International Patent Application Publication No. WO00/24745; the pyrazolo [4,3-d]pyrimidin-4-ones disclosed in EP-A-0995750; the compounds disclosed in International Patent Application Publication No. WO95/19978; the compounds disclosed in International Patent Application Publication No. WO99/24433; the pyrazolo [4,3-d]pyrimidin-7-ones disclosed in International Patent Application Publication No. WO01/27112; the pyrazolo [4,3-d]pyrimidin-7-ones disclosed in International Patent Application Publication No. WO01/27113; the compounds disclosed in EP-A-1092718; the compounds disclosed in EP-A-1092719; and the compounds disclosed in International Patent Application Publication No. WO93/07124.

Preferred PDE5 inhibitors for use as a second compound in a combination of this invention include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d] pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); 6-benzo[1,3]dioxol-5-yl-2-methyl-2,3,6,7,12,12a-hexahydro-pyrazino[1',2':1,6]pyrido[3,4-b]indole-1,4-dione (cialis); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO01/27113, Example 8); 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO01/27113, Example 15); 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO01/27113, Example 66); 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one (see WO01/27112, Example 124); 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one (see WO01/27112, Example 132); (6R, 12aR)-2,3,6,7,12,12a-hexahydro-2-methyl-6-(3,4-methylenedioxyphenyl) -pyrazino[2',1':6,1]pyrido[3,4-b]indole-1,4-dione (IC-351), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 in WO93/07124 (EISAI); and compounds 3 and 14 from Rotella D P, *J. Med. Chem.*, 2000, 43, 1257.

Any activator of AMP-activated protein kinase may be used as the second compound of a combination of this invention. A suitable such activator is, e.g., 5-amino-4-imidazolecarboxamide ribonucleoside.

Any PPAR-γ agonist may be used as the second compound of a combination of this invention. Suitable PPAR-γ agonists include Avandia or Actos.

Any dual PPAR-α/PPAR-γ agonist may be used as the second compound of a combination of this invention. Suitable dual agonists include farglitazar.

Other anti-diabetic agents that may be used as the second compound of a combination of this invention include protein kinase C-β inhibitors, PTP1B inhibitor, glucagon antagonists, glycogen synthase kinase-3 (GSK-3) inhibitors, GLP-1 agonists or soluble guanylate cyclase (sGC) activator.

The Formula I compounds can be used in combination with anti-obesity agents. Any anti-obesity agent may be used as the second agent in such combinations and examples are provided below and in the Summary of the Invention. Such anti-obesity activity is readily determined by those skilled in the art according to standard assays (e.g., as detailed below).

Any thyromimetic may be used as the second agent in combination with a Formula I compound. Such thyromimetic activity is readily determined by those skilled in the art according to standard assays (e.g., Atherosclerosis (1996) 126: 53–63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other anti-obesity agents include sibutramine which can be prepared as described in U.S. Pat. No. 4,929,629. and bromocriptine which can be prepared as described in U.S. Pat. Nos. 3,752,814 and 3,752,888.

Any melanocortin receptor agonist, melanocortin receptor modulator or melanocortin receptor enhancer may be used as the second compound of a combination of this invention. Suitable melanocortin receptor agonists, modulators or enhancers include melanotan II; and compounds disclosed in International Patent Application Publication Nos. WO99/64002, WO00/74679, WO99/55679, WO01/05401, WO00/58361, WO01/14879, WO01/13112 and WO99/54358.

Any serotonin receptor agonist, antagonist or modulator may be used as the second compound in a combination of this invention. It is particularly preferred to use agonists, antagonists or modulators of 5HT1A. Suitable agonists, antagonists or modulators include 5HT2A; 5HT2C; 5HT3; and 5HT6 receptors, including those described in International Patent Application Publication Nos. WO99/02159, WO00/02550 and WO00/28993.

Any neurokinin receptor (NK) antagonist may be used as the second compound of a combination of this invention. Suitable NK receptor antagonists include those described in International Patent Application Publication No. WO99/64008.

Any modulator of transporters for noradrenaline or dopamine may be used as the second compound of a combination of this invention. Suitable such modulators include bupropion.

Any $\beta$-adrenergic agonist may be used as the second compound in the combination aspect of this invention. $\beta$-Adrenergic agents have been categorized into $\beta_1$, $\beta_2$, and $\beta_3$ subtypes. Agonists of $\beta$-receptors promote the activation of adenyl cyclase. Activation of $\beta_1$ receptors invokes increases in heart rate. Activation of $\beta_2$ receptors induces relaxation of smooth muscle tissue which produces a drop in blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Such activity is readily determined by those skilled in the art according to standard assays. Several compounds are described and referenced below; however, other $\beta$-adrenergic agonists will be known to those skilled in the art. International Patent Application, Publication No. WO 96/35671 (the disclosure of which is incorporated herein by reference) discloses compounds, such as substituted aminopyridines, which are $\beta$-adrenergic agonists. International Patent Application, Publication No. 93/16189 (the disclosure of which is incorporated herein by reference) discloses the use of selective $\beta_3$ receptor agonists in combination with compounds which modify eating behavior for the treatment of obestiy.

Any NPY receptor antagonist may be used as the second component in the combination aspect of this invention. The term NPY receptor antagonist refers to compounds which interact with NPY receptors and inhibit the activity of neuropeptide Y at those receptors and thus are useful in treating disorders associated with neuropeptide Y, such as feeding disorders, including obesity. Such inhibition is readily determined by those skilled in the art according to standard assays (such as those described in International Patent Application, Publication No. WO 99/07703). In addition, the compounds described and referenced below are NPY receptor antagonists; however, other NPY receptor antagonists will also be known to those skilled in the art. WO 99/07703 (the disclosure of which is hereby incorporated by reference) discloses certain 4-aminopyrrole (3,2-d) pyrimidines as neuropeptide Y receptor antagonists. WO 96/14307, WO 96/40660, WO 98/03492; WO 98/03494; WO 98/03493; WO 96/14307; WO 96/40660, (the disclosures of which are hereby incorporated by reference) disclose additional compounds, such as substituted benzylamine derivatives, which are useful as neuropeptide Y specific ligands.

Other anti-obesity agents include phenylpropanolamine, ephedrine, pseudoephedrine, a cholecystokinin-A (hereinafter referred to as CCK-A) agonist, a monoamine reuptake inhibitor (such as sibutramine), a sympathomimetic agent, a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a galanin antagonist or a GI lipase inhibitor or decreaser (such as orlistat). Other antiobesity agents include phosphatase 1B inhibitors, bombesin agonists, dehydroepiandrosterone or analogs thereof, glucocorticoid receptor modulators, orexin receptor antagonists, urocortin binding protein antagonists, glucagon-like peptide-1 (insulinotropin) agonists or dipeptidyl peptidase IV (DPPIV) inhibitors. A particularly preferred monoamine reuptake inhibitor is sibutramine, which can be prepared as disclosed in U.S. Pat. No. 4,929,629, the disclosure of which is incorporated herein by reference. A particularly preferred dopamine agonist is bromocriptine, which can be prepared as disclosed in U.S. Pat. Nos. 3,752,814 and 3,752,888, the disclosures of which are incorporated herein by reference. Another preferred anorectic agent is phentermine, which can be prepared as disclosed in U.S. Pat. No. 2,408,345, the disclosure of which is incorporated herein by reference.

The Formula I compounds can also be used in combination with other cardiovascular (e.g., antihypertensive agents). Any cardiovascular agent may be used as the second agent in such combinations and classes and specific examples are provided in the Summary of the Invention and below. Such cardiovascular activity is readily determined by those skilled in the art according to standard assays (e.g., blood pressure measurements).

Any $\alpha$-adrenergic receptor antagonist compound may be used as the second compound of a combination of this invention. Suitable $\alpha$-adrenergic receptor antagonists for use herein include the $\alpha$-adrenergic receptor blockers described in International Patent Application Publication No. WO99/30697. Selective $\alpha_1$-adrenoceptor, $\alpha_2$-adrenoceptor blockers and non-selective adrenoceptor blockers may also be used as the second $\alpha$-adrenergic receptor antagonist compound of this invention. Suitable $\alpha_1$-adrenoceptor blockers include phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, doxazosin, terazosin, abanoquil and prazosin. Suitable $\alpha_2$-adrenoceptor blockers include those disclosed in U.S. Pat. No. 6,037,346, dibenarnine, tolazoline, trimazosin and dibenarnine. Suitable α-adrenergic receptors for use as the second compound of a combination of this invention are also described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000. Other suitable $\alpha_2$-adrenoceptor blockers include clonidine, papaverine, papaverine hydrochloride, each of which may optionally be administered in the presence of a cariotonic agent such as, but not limited to, pirxamine.

Any nitrous oxide donor (NO-donor or NO-agonist) compound may be used as the second compound of a combination of this invention. Suitable NO-donor compounds include organic nitrates, such as mono-, di- or tri-nitrates; organic nitrate esters such as glyceryl binitrate (also known as nitroglycerin), isosorbide 5-mononitrate, isosorbide dinitrate, pentaerythritol tetranitrate, erythrityl tetranitrate, amylnitrate, a diazenium diolate (NONOate), and 1,5-pentanedinitrate; sodium nitroprusside (SNP); 3-morpholinosydnonimine molsidomine; S-nitroso-N-acetyl penicilliamine (SNAP); S-nitroso-N-glutathione (SNO-GLU); N-hydroxy-L-arginine; linsidomine; linsidomine chlorohydrate; (SIN-1) S-nitroso-N-cysteine; L-arginine; ginseng; zizphi fructus; molsidomine; and nitrosylated maxisylyte derivatives such as NMI-678-11 and NMI-937 (International Patent Application Publication No. WO00/12075).

Any potassium channel opener or modulator may be used as the second compound of a combination of this invention. Suitable potassium channel openers/modulators for use herein include nicorandil, cromokalim, levcromakalim, lemakalim, pinacidil, cliazoxide, minoxidil, charybdotoxin, glyburide, 4-aminopyridine and barium chloride ($BaCl_2$).

Any vasodilator agent may be used as the second compound of a combination of this invention. Suitable vasodilator agents for use herein include nimodepine, pinacidil, cyclandelate, isoxsuprine, chloroprumazine, halo peridol and trazodone.

Any ergot alkoloid may be used as the second compound of a combination of this invention. Suitable ergot alkaloids include those disclosed in U.S. Pat. No. 6,037,346; acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride.

Any angiotensin receptor antagonist may be used as the second compound of a combination of this invention. Suitable angiotensin receptor antagonists include losartan, candersartan, eprosartan, irbesartan and valsartan.

Any substrate for NO-synthase may be used as the second compound of a combination of this invention. Suitable NO-synthase substrates include, inter alia, L-arginine.

Any calcium channel blocker may be used as the second compound of a combination of this invention. Suitable calcium channel blockers include, amlodipine and amlodipine besylate (also known as Norvasc®). Specific examples of antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®.

Any angiotensin converting enzyme inhibitor (ACE inhibitor) may be used as the second compound of a combination of this invention. Suitable ACE inhibitors include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S Pat. No. 4,344,949; ramipril, which may be prepared as disclosed in U.S Pat. No. 4,587,258; spirapril, which may be prepared as disclosed in U.S Pat. No. 4,470,972; temocapril, which may be prepared as disclosed in U.S Pat. No. 4,699,905; and trandolapril, which may be prepared as disclosed in U.S Pat. No. 4,933,361;

Any compound which is a combined inhibitor of angiotensin-converting enzyme and neutral endopeptidase may be used as the second compound of a combination of this invention. A suitable such combined inhibitor is, e.g., omapatrilat.

Any acetylcholinesterase inhibitor may be used as the second compound of a combination of this invention. A suitable acetylcholinesterase inhibitor is, e.g., donezipil.

Any hormone replacement therapy (HRT) agent may be used as the second compound of a combination of this invention. Suitable HRT agents include Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS and Tibolone.

The starting materials and reagents for the above described Formula I compounds and combination agents, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the Formula I compounds of this invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compounds or an intermediate in their synthesis which contain an acidic or basic moiety may be separated into their component pure enantiomers by forming a diastereomeric salt with an optically pure chiral base or acid (e.g. 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

More specifically, the Formula I compounds of this invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD [obtained from Chiral Technologies, Exton, Pa.]) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the Formula I compounds of this invention are acidic and they form a salt with a pharmaceutically acceptable cation. Most of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Those skilled in the art will recognize that some of the compounds herein can exist in several tautomeric forms. All such tautomeric forms are considered as part of this invention. For example all enol-keto forms of the compounds of Formula I are included in this invention.

In addition, when the Formula I compounds of this invention form hydrates or solvates they are also within the scope of the invention.

The Formula I compounds of this invention, their prodrugs and the salts of such compounds and prodrugs are all adapted to therapeutic use as agents that inhibit acetyl-CoA carboxylase (ACC) activity in mammals, particularly humans. Thus, it is believed that the compounds of this invention, by inhibiting ACC activity and reducing malonyl-CoA levels, both increase fatty acid utilization in oxidative tissues such as the skeletal muscles and the liver and also inhibit denovo fatty acid synthesis in lipogenic tissues such as the liver and adipose tissue. As a consequence this leads to depletion of tissue triglyceride stores and ultimately leads to increased insulin sensitivity in tissues of the body including the liver, skeletal muscles, and adipose tissues, reduction in VLDL secretion by the liver, and modification of insulin secretion by the pancreas. Furthermore, it is believed, by increasing fatty acid utilization and by preventing increases in de novo fatty acid synthesis, chronic administration of an ACC-inhibitor depletes liver and adipose tissue triglyceride stores in obese subjects consuming a low-fat diet, leading to selective loss of body fat. Accordingly, an ACC inhibitor favorably affects a broad array of disease states including metabolic syndrome (Syndrome X or insulin resistant syndrome), diabetes, obesity, atherosclerosis, hypertension, and coronary heart disease in mammals, including humans.

The utility of the Formula I compounds of the invention, their prodrugs and the salts of such compounds and prodrugs (as well as the combination agents—the "second compounds") as medical agents in the treatment of the above described disease/conditions in mammals (e.g., humans, male or female) is demonstrated by the activity of the compounds of this invention in conventional assays and the in vitro and in vivo assays described below. The in vivo assays (with appropriate modifications within the skill in the art) may be used to determine the activity of other insulin sensitizing, anti-hyperinsulinemia, anti-diabetic, anti-obesity, anti-dyslipidemic and anti-atherosclerotic agents as well as the compounds of this invention. The combination protocol described below is useful for demonstrating the utility of the combinations of the agents (e.g., the compounds of this invention) described herein. Such assays also provide a means whereby the activities of the Formula I compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols can of course be varied by those skilled in the art.

Direct Inhibition of the Activities of ACC1 and ACC2

The ACC inhibitory activity of the Formula I compounds of this invention, their prodrugs and the salts of such compounds and prodrugs can be demonstrated by methods based on standard procedures. For example direct inhibition of ACC1 and ACC2 activity and the specificity of the inhibition can be determined using preparations of ACC1 from mammalian liver and ACC2 from mammalian skeletal muscle.

[1] Preparation of ACC1 and ACC2. ACC1 can be obtained from rat liver and ACC2 can be obtained from rat skeletal muscle based upon standard procedures such as those described by Thampy and Wakil (J. Biol. Chem. 260: 6318–6323; 1985). Male CD rats weighing 150–200 g are fasted for 2 days and then fed a high sucrose diet diet (AIN-76A rodent diet; Cat # D10001, Research Diets Inc., New Brunswick, N.J.), for 3 days at which time they are killed by $CO_2$ asphyxiation. The livers (for ACC1 preparation) or skeletal muscle tissue (for ACC2 preparation) are removed, rinsed in ice-cold phosphate-buffered saline (PBS), and homogenized in 5 volumes of homogenization buffer (50 mM potassium phosphate, pH 7.5, 10 mM EDTA, 10 mM 2-mercaptoethanol, 2 mM benzamidine, 0.2 mM phenylmethylsulfonylfluoride (PMSF), 5 mg/L each leupeptin, aprotinin, and antitrypsin) in a Waring blender for 1 minute at 4° C. All subsequent operations are carried out at 4° C. The homogenate is made 3% with respect to polyethylene glycol (PEG) by the addition of 50% PEG solution and centrifuged at 20,000×g for 15 minutes. The resulting supernatant is adjusted to 5% PEG with the addition of 50% PEG solution and stirred for 5 minutes. The pellet (contains ACC activity) is collected by centrifugation at 20,000×g for 20 minutes, rinsed with ice-cold doubly distilled $H_2O$ to remove excess PEG and resuspended in one-fourth the original homogenate volume with homogenization buffer. Ammonium sulfate (200 g/liter) is slowly added with stirring. After 45 minutes the enzyme is collected by centrifugation for 30 minutes at 20,000×g, resuspended in 10 ml of 50 mM HEPES, pH7.5, 0.1 mM DTT, 1.0 mM EDTA, and 10% glycerol and desalted on a G-25 column (2.5 cm×50 cm) (Pharmacia Piscataway New Jersey) equilibrated with the same buffer. The desalted enzyme preparation is stored in aliquots at −70° C. Immediately prior to use, frozen ACC1 or ACC2 aliquots are thawed, diluted to 500 µg/ml in buffer containing 50 mM HEPES, pH7.5, 10 mM MgCl2, 10 mM tripotassium citrate, 2.0 mM dithiothreitol (DTT), and 0.75 mg/ml fatty acid-free borine serum albumin (BSA) and preincubated at 37° C. for 30 minutes.

[2] Measurement of ACC inhibition. The procedures for measuring ACC1 inhibition and ACC2 inhibition are identical except for the source of the isozyme. For measurement of ACC activity and assessment of ACC inhibition, test compounds are dissolved in dimethylsulfoxide (DMSO) and 1 µl aliquots are placed in 0.5 ml polypropylene tubes. Control tubes contain 1 µl of DMSO alone. Tubes are incubated at 37° C. in a constant temperature water bath. All assay tubes receive 139 µl of substrate buffer containing 50 mM HEPES, pH7.5, 2.0 mM MgCl$_2$. 2.0 mM tripotassium citrate, 2 mM DTT, 0.75 mg/ml BSA, 25 µM acetyl-CoA, 4.0 mM ATP, and 12.5 mM KH[$^{14}$C]O$_3$ (2×10$^6$ cpm). The reaction is then initiated by the addition of 10 µl of preincubated ACC fraction prepared as described above. After 7 minutes the reaction is terminated by the addition of 50 µl of 6N HCl and a 150 µl aliquot of the reaction mixture is transferred to glass scintillation vials and evaporated to dryness at 90° C. for at least 1 hour. The dried vials are then cooled, 0.5 ml of water and 5.5 ml of Beckman Readisafe liquid scintillation fluid are added, and the radioactivity is determined using a liquid scintillation counter. Tubes that received HCl before ACC served as blanks.

[3] Specificity for ACC1 vs ACC2 inhibition. The specificity of a compound for inhibiting ACC1 vs ACC2 can be determined by comparing the concentration of test compound required to inhibit 50% of the activity contained in an aliquot of ACC1 as compared with the concentration of the same compound required to inhibit 50% of the activity of an aliquot of ACC2.

Measurement of ACC Inhibition in Cultured Cells

The ACC inhibitory activity of the Formula I compounds of this invention, their prodrugs and the salts of such compounds and prodrugs can be confirmed in cultured human cells using methods based on standard procedures. For example, since ACC catalyzes the first committed step in the biosynthesis of fatty acids, the in vivo activity of these compounds can be confirmed by measuring the ability of Formula I compounds of this invention, their prodrugs and the salts of such compounds and prodrugs to prevent the formation of radiolabeled fatty acids from radiolabeled acetate in cultured mammalian hepatocytes or in cultured human hepatoma cells of the Hep-G2 cell line (ATCC HB 8065). Direct assessment of malonyl-CoA production in cells isolated from tissues that do (e.g. liver and adipose tissue) or do not synthesize fatty acids (e.g. skeletal muscle) can also be used to determine ACC inhibition in cells isolated from those tissues.

[1] Measurement of fatty acid synthesis inhibition in cultured cells. Fatty acid synthesis is assessed in cultured mammalian hepatocytes or in human hepatoma cells of the Hep-G2 cell line by measuring incorporation of [2-$^{14}$C] acetate into saponifyable lipids essentially as previously described for assessment of sterol synthesis (Harwood et al. Biochem. Pharmacol. 53: 839–864,1997; Petras et al. J. Lipid Res. 40: 24–38,1999) with the following modifications to allow assessment fatty acid synthesis. For example, Hep-G2 cells grown in T-75 flasks and released by trypsin treatment as previously described (Harwood et al. Biochem. Pharmacol. 53: 839–864,1997; Petras et al. J. Lipid Res. 40: 24–38, 1999), are seeded in 24 well plates at a density of 1.2×10$^5$ cells/well and maintained in 1.0 mL of Supplemented Dulbecco's minimal essential media (DMEM) medium (DMEM medium containing 10% heat-inactivated fetal bovine serum, 2 mM L-glutamine, 40 µg/mL gentamicin) for 7 days in a 37° C., 5% CO$_2$ incubator with medium changes on days 3 and 5. At this time, cultures reach 80–90% confluency and maintained a >90% cell viability (Trypan blue dye exclusion). On day 8, the medium is removed and replaced with fresh medium containing 1% DMSO±the test compound. Immediately after compound addition, 25 µL of media containing 4 µCi of [2-$^{14}$C]acetate (56 mCi/mmol) is added to each incubation well. Plates are then sealed with parafilm to avoid evaporation, and cells are incubated at 37° C. for 6 hours with gentle shaking. After incubation, the samples are saponified by addition to each well of 1 ml of 5 N KOH in MeOH, followed first by incubation for 2 hours at 70° C. and then by overnight incubation at room temperature. Mixtures are transferred to glass conical tubes and extracted three times with 4.5 ml hexane to remove the nonsaponifyable lipids (e.g. cholesterol, post-squalene cholesterol precursors and other nonsaponifyable lipids). The remaining aqueous phase (containing fatty acid sodium salts) is acidified to pH<2 by addition of 0.5 ml of 12 M HCl. The resulting mixtures are transferred to glass conical tubes and extracted three times with 4.5 ml hexane. The pooled organic fractions (containing protonated fatty acids) are dried under nitrogen, resuspended in 50 µL of chloroform:methanol::1:1(v/v) and applied to 1×20 cm channels of Silica Gel 60C TLC plates. Channels containing non-radioactive fatty acids were included on selected TLC plates as separation markers. TLC plates were developed in hexane:diethyl ether:acetic acid (70:30:2), air dried, and visualized for radioactive fatty acids by analysis using a Berthold Linear Radioactivity Analyzer (Berthold, Gaithersburg, Md., USA) that reports radioactive peak location and integrated peak area. Inhibition of fatty acid synthesis by the test compound can is expressed as the concentration required to reduce by 50% the dpm [2-$^{14}$C] acetate incorporated into saponifyable lipids during the 6 hour incubation at 37° C.

[2] Measurement of malonyl-CoA production inhibition in cultured cells. Direct assessment of malonyl-CoA production in cells isolated from tissues that either do (e.g. liver and adipose tissue) or do not synthesize fatty acids (e.g. skeletal muscle), through its stoichiometric conversion to radiolabeled palmitate in the presence of purified fatty acid synthetase and radiolabeled acetate, can also be used to determine ACC inhibition in cells isolated from those tissues as previously described (McGarry et al. J. Biol. Chem. 253: 8291–8293,1978). The procedure as it relates to whole tissues is outlined below and can be readily adapted to cultured cells by those skilled in the art.

Acute in vivo Assessment of ACC Inhibition in Experimental Animals

The ACC inhibitory activity of the Formula I compounds of this invention their prodrugs and the salts of such compounds and prodrugs can be confirmed in vivo by evaluation of their ability to inhibit hepatic fatty acid production and to stimulate whole body fatty acid oxidation using methods based on standard procedures. For example, since ACC catalyzes the first committed step in the biosynthesis of fatty acids, the in vivo activity of these compounds can be confirmed by measuring the ability of the Formula I compounds of this invention, their prodrugs and the salts of such compounds and prodrugs to prevent the formation of radiolabeled fatty acids from radiolabeled acetate in the livers of treated mammals.

Direct assessment of radiolabeled malonyl-CoA production from radiolabeled acetate in tissues that either do (e.g. liver and adipose tissue) or do not synthesize fatty acids (e.g. skeletal muscle) can also be used to determine ACC inhibition in those tissues. Since reduced malonyl-CoA levels as a consequence of ACC inhibition, relieve the malonyl-CoA mediated feedback inhibition of carnitine-palmitoyltransferase 1 (CPT1), the enzyme that catalyzes the rate limiting reaction in mitochondrial fatty acid oxidation, the in vivo activity of the Formula I compounds of this invention, their prodrugs and the salts of such compounds and prodrugs can be confirmed by measuring their ability to increase the utilization of fatty acids as a source of energy, as assessed by a reduction in respiratory quotient in treated mammals.

[1] Measurement of fatty acid synthesis inhibition in experimental animals. Incorporation of [2-$^{14}$C]acetate into saponifyable lipids in the livers of mammals (e.g. CD1 mice, C57BI/6J-ob/ob mice, Sprague Dawley rats(available from Charles River Boston, Mass. or Jackson Labs Bar Harbor, Me.)) can be measured essentially as previously described for assessment of hepatic sterol synthesis (Harwood et al, Biochem. Pharmacol, 40: 1281–1293, 1990; Harwood et al. Biochem. Pharmacol. 53: 839–864,1997) with the following modifications to allow for assessment fatty acid synthesis. For example, Sprague Dawley rats are administered a 0.1 ml per 40 g body weight of an oral bolus of vehicle (e.g. water or 0.5% methylcellulose in water)±test compound. One to four hours after compound administration, animals receive an intraperitoneal injection of 0.5 ml of [2-$^{14}$C]acetate (64 $\mu$Ci/ml; 57 mCi/mmol). One hour after radiolabel administration, animals are killed by $CO_2$ asphyxiation and two, 0.75 g liver pieces are removed and saponified at 70° C. for 120 minutes in 1.5 ml of 2.5 M NaOH. After saponification, 2.5 ml of absolute EtOH are added to each sample and the solutions are mixed and allowed to stand overnight. Petroleum ether, 4.8 ml, is then added to each sample and the mixtures are first shaken vigorously for 2 minutes then centrifuged at 1000×g in a bench-top Sorvall for 5 minutes. The resultant petroleum ether layers, which contain the nonsaponifyable lipids (e.g. cholesterol, post-squalene cholesterol precursors and other nonsaponifyable lipids), are removed and discarded. The remaining aqueous layer (containing fatty acid sodium salts) is acidified to pH<2 by addition of 0.6 ml of 12 M HCl and extracted two times with 4.8 ml of petroleum ether. The pooled organic fractions (containing protonated fatty acids) are transferred to liquid scintillation vials, dried under nitrogen, dissolved in 7 ml of Aquasol liquid scintillation fluid, and assessed for radioactivity using a liquid scintillation counter. Inhibition of fatty acid synthesis by the test compound is expressed as the concentration required to reduce by 50% the dpm [2-$^{14}$C]acetate incorporated into saponifyable lipids during the 1 hour interval between radiolabeled acetate injection and $CO_2$ asphyxiation.

[2] Measurement of malonyl-CoA production inhibition in experimental animals. Direct assessment of malonyl-CoA production in tissues that either do (e.g. liver and adipose tissue) or do not synthesize fatty acids (e.g. skeletal muscle), through its stoichiometric conversion to radiolabeled palmitate in the presence of purified fatty acid synthetase and radiolabeled acetyl-CoA, can also be used to determine ACC inhibition in those tissues as previously described (McGarry et al. J. Biol. Chem. 253: 8291–8293, 1978). The animals are treated with vehicle±test compound as described in [1] Measurement of fatty acid synthesis inhibition in experimental animals above. Briefly, assays are carried out in duplicate in stoppered glass test tubes. Reaction mixtures contain, in 1.025 ml of 200 mM potassium phosphate buffer (pH=7.0), 2.5 mM dithiothreitol, 2.0 mM EDTA, 0.2 mM NADPH, 1 mg/ml fatty acid free bovine serum albumin, 4.4 uM [3H]acetyl-CoA (~150,000 dpm/nmol), and appropriate quantities of malonyl-CoA standard or test tissue extract. Tissue extracts are prepared from tissues (e.g. liver and skeletal muscle) that are freeze-clamped within 10 seconds after $CO_2$ asphyxiation by first pulverizing the tissue under liquid nitrogen then extracting 1 g of powdered tissue with 5 ml of 6% (w/v) $HClO_4$ and neutralizing the extract to pH 6.0 with KOH and centrifugation to remove particulate residue. Reactions are initiated by addition of 25 mU of purified fatty acid synthetase. After a 45 min incubation at 37° C., reactions are terminated by addition of 25 ul of 70% (w/v) $HClO_4$ and nascent palmitate is then extracted by addition to each tube of 1 ml EtOH then 5 ml petroleum ether. After vigorous mixing for 30 seconds and centrifugation to facilitate phase separation, the petroleum ether phase is transferred to a second glass tube containing 2 ml water, shaken, recentrifuged, and 2.0 ml of the petroleum ether phase is transferred to liquid scintillation vials, dried, and assessed for radioactivity in a liquid scintillation counter after addition of 10 ml Aquasol liquid scintillation fluid. Blanks containing no added malonyl-CoA nor liver extract are included with each series of determinations and subtracted from all values. Inhibition of malonyl-CoA production by the test compound is expressed as the concentration required to reduce by 50% the dpm [2-$^{14}$C]acetyl-CoA incorporated into palmitate during the 45 minute incubation at 37° C.

[3] Measurement of Fatty Acid Oxidation Stimulation in Rats.

The ACC inhibitory activity of the Formula I compounds of this invention, their prodrugs and the salts of such compounds and prodrugs can be further confirmed in vivo by assessing the ability of ACC inhibition to increase fatty acid utilization by employing methods based on standard procedures. For example, during a shift from the oxidation of carbohydrate to the oxidation of fatty acids or a shift from fatty acid synthesis to oxidation, there is a decrease in respiratory quotient (RQ)=ratio of $CO_2$ production/$O_2$ consumption. Because fatty acids are in a more reduced state than carbohydrates (such as glucose), there is greater amount of oxygen consumed for each $CO_2$ produced and therefore a lower RQ. If an animal is utilizing only carbohydrate, RQ=1.0, whereas if an animal is utilizing only fatty acids, RQ=0.7. Thus, the RQ in animals, including humans and companion animals, is an indirect measure of type of fuel being utilized. Indirect calorimetry is commonly used in animals, including humans, by those skilled in the relevant art to measure RQ.

Those skilled in the art understand that decreased RQ and the concomitant shifting fuel utilization from the oxidation of carbohydrate to the oxidation of fat may decrease body fat stores and be efficacious with respect to the treatment of, e.g., obesity, metabolic syndrome and diabetes.

The ability of the Formula I compounds of this invention, their prodrugs and the salts of such compounds and prodrugs to generate a decrease in RQ response may be demonstrated according to the following protocol. This in vivo screen is designed to evaluate the efficacy of compounds that are ACC inhibitors, using as an efficacy endpoint measurement of whole body oxygen consumption, $CO_2$ production and RQ. The protocol involves administering a single dose of compound to Sprague Dawley rats. Male Sprague Dawley rats having a body weight range of from about 350–400 g are housed under standard laboratory conditions prior to the initiation of the study.

On the day of testing the compound, oxygen consumption and RQ is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment. The subject rats are removed from their home cages and their body weights recorded. The rats are placed into the sealed chambers (43×43×10 cm) of the Oxymax (one rat per chamber), the chambers are placed in the activity monitors, and the air flow rate through the chambers is set at about 1.6 L/min. The Oxymax software calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Baseline oxygen consumption, RQ and ambulatory activity are measured about every 10 minutes for about 1 to 3.5 hours. After obtaining baseline data, the chambers are opened and a test compound and a vehicle are administered by oral gavage as a single dose. A test compound is dissolved in vehicle containing about 0.5% of methyl cellulose in water or other vehicle. The dosing volume is about 1 ml. After dosing the rats are returned to the Oxymax chambers, the lids of the chambers are closed and measurements are made every 10 minutes for about 3 to 6 hours after dosing. Change in RQ in response to test compound or vehicle is calculated on individual rats by dividing the average of the post-dosing values (excluding values obtained during time periods where ambulatory activity exceeds 100 counts) by the average of the predosing baseline values (excluding the first 5 values and values obtained during time periods where ambulatory activity exceeds 100 counts) and expressing the data as % change in RQ.

Sub-Chronic and Chronic Efficacy in Experimental Animals

The compounds of the present invention are readily adapted to clinical use as hyperinsulinemia reversing agents, insulin sensitizing agents, anti-obesity agents and anti-atherosclerotic agents. Such activity can be determined by the amount of test compound that reduces insulin levels, blunts the rise and/or accelerates the reduction in insulin and glucose levels in response to an oral glucose challenge, reduces body weight and/or reduces body composition (e.g. reduces the percentage of body fat), and reduces the accumulation of lipid deposition in the blood vessel walls relative to a control vehicle without test compound in mammals, for example Sprague Dawley rats fed either chow, a high sucrose diet or a high fat diet for from 3–8 weeks prior to and during test compound administration or male ob/ob mice or cholesterol-fed rabbits.

Also, since the concentration of insulin in blood is related to the promotion of vascular cell growth and increased renal sodium retention, (in addition to the other actions, e.g., promotion of glucose utilization) and these functions are known causes of hypertension, the compounds of this invention, by virtue of their hypoinsulinemic action, prevent, arrest and/or regress hypertension.

[1] Subchronic assessment of anti-diabetic efficacy in rats and mice. The antidiabetic potential of a Formula I compound of this invention, their prodrugs and the salts of such compounds and prodrugs can be demonstrated by evaluating their anti-hyperinsulinemia potential and insulin sensitizing potential using methods based on standard procedures. For example, the anti-hyperinsulinemia potential and insulin sensitizing potential of these compounds can be demonstrated in Sprague Dawley rats fed either a standard rodent diet, a high sucrose diet (AIN-76A rodent diet; Cat # D10001, Research Diets Inc., New Brunswick, N.J.) or a high fat diet (Cat # D12451, Research Diets Inc., New Brunswick, N.J.) ad libitum for from 3–4 weeks prior to and during test compound administration or in 4–8 week old male C57BL/6J-ob/ob mice (obtained from Jackson Laboratory, Bar Harbor, Me.) fed standard rodent diet ad libitum. Animals are treated for 1 to 8 weeks with test compound administered either by oral gavage in water or in 0.25% methylcellulose in water using a S.D., B.I.D. or T.I.D. dosing regimen or via in feed administration using a powdered version of the above-mentioned diets.

For studies in which the anti-hyperinsulinemia potential of Formula I compounds are evaluated, at various times during the study or at sacrifice (by $CO_2$ asphyxiation), blood is collected either from a tail vein of unanesthetized rats or from the retro-orbital sinus of unanesthetized mice, or from the vena cava of rats or mice at sacrifice into 0.5 ml serum separator tubes. The freshly collected samples are centrifuged for two minutes at 10,000×g at room temperature, and the serum supernatant is stored at −80° C. until analysis. Serum insulin concentration is determined using Equate® RIA INSULIN kits (double antibody method; as specified by the manufacturer) available from Binax, South Portland, Me. The interassay coefficient of variation is $\leqq 10\%$. The serum insulin lowering activity of the test compounds are determined by statistical analysis (unpaired t-test) of the mean serum insulin concentration between the test compound group and the vehicle-treated control group.

For studies in which the insulin-sensitizing potential of test compounds is evaluated, at various times during the study fasted animals are administered an oral or intraperitoneal 1.0 g/kg body weight bolus of glucose, and blood is collected either from a tail vein of unanesthetized rats or from the retro-orbital sinus of unanesthetized mice, at various times up to 2 hours after glucose administration into 0.5 ml serum separator tubes. The freshly collected samples are centrifuged for two minutes at 10,000×g at room temperature, and the serum supernatant is stored at −80° C. until analysis. Serum insulin concentration is determined using Equate® RIA INSULIN kits as described above. Serum glucose concentration is determined using the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™ Glucose-UV Test reagent system (Abbott Laboratories, Irving, Tex.) (a modification of the method of Richterich and Dauwalder, *Schweizerische Medizinische Wochenschrift*, 101: 860 (1971)). The insulin-sensitizing activity of the test compounds are determined by statistical analysis (unpaired t-test) of the mean difference in peak insulin and glucose concentrations and the rate of insulin and glucose disappearance from the plasma after their respective peak levels between the test compound group and the vehicle-treated control group.

For studies in which the lipid-lowering potential of test compounds is evaluated, at various times during the study or at sacrifice (by $CO_2$ asphyxiation), blood is collected either from a tail vein of unanesthesized rats or from the retro-orbital sinus of unanesthesized mice, or from the vena cava of rats or mice at sacrifice into 0.5 ml serum separator tubes. The freshly collected samples are centrifuged for two minutes at 10,000×g at room temperature, and the serum supernatant is stored at −80° C. until analysis. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from Amano International Enzyme Co., Inc., as adapted for use with the Abbott VP™ and VP Super System® Autoanalyzer (Abbott Laboratories, Irving, Tex.), or the Abbott Spectrum CCX™ (Abbott Laboratories, Irving, Tex.). The serum triglyceride, cholesterol and free fatty acid lowering activity of the test compounds are determined by statistical analysis (unpaired t-test) of the mean serum triglyceride, cholesterol, and free fatty acid concentrations between the test compound group and the vehicle-treated control group.

[2] Subchronic assessment of anti-obesity efficacy in rats and mice. The antiobesity potential of a Formula I compound of this invention, their prodrugs and the salts of such compounds and prodrugs can be demonstrated by evaluating their potential to produce a reduction in body weight, a reduction in percentage body fat, and a reduction in plasma leptin levels.

For example, the body weight reduction, percentage body fat reduction, and plasma leptin reduction potential of test compounds can be demonstrated in Sprague Dawley rats fed either a standard rodent diet, a high sucrose diet (AIN-76A rodent diet; Cat # D10001, Research Diets Inc., New Brunswick, N.J.) or a high fat diet (Cat # D12451, Research Diets Inc., New Brunswick, N.J.) ad libitum for from 3–4 weeks prior to and during test compound administration or in 4–8 week old male C57BL/6J-ob/ob mice (obtained from Jackson Laboratory, Bar Harbor, Me.) fed standard rodent diet ad libitum. Animals are treated for 1 to 8 weeks with a test compound administered either by oral gavage in water or 0.25% methylcellulose in water using a S.D., B.I.D. or T.I.D. dosing regimen or via in feed administration using a powdered version of the above-mentioned diets.

Whole body weight loss can be assessed simply be comparison of total body weighy before and after treatment with a test compound. For assessment of weight loss and change in body composition (e.g. the change in percentage body fat and in the ratio of lean body mass to fat mass) treated and control animals were lightly anesthetized and scanned using dual-energy x-ray absorptiometry (DEXA, QDR-1000/W, Hologic Inc., Waltham, Mass.) equipped with "Regional High Resolution Scan" software. The scan field size was adjusted to accommodate the size of the species being evaluated. Resolution was 0.0254×0.0127 cm and scan speed was 7.25 mm/second. The whole body weight, percentage body fat, and ratio of fat mass to lean body mass lowering activity of the test compounds are determined by statistical analysis (unpaired t-test) of the mean whole body weight, percentage body fat, and ratio of fat mass to lean body mass between the test compound group and the vehicle-treated control group.

Changes in plasma leptin levels closely parallel changes in percentage body fat and are therefore a useful marker for assessing anti-obesity potential. For assessment of changes in plasma leptin levels in response to treatment with test compounds, at various times during the study or at sacrifice (by $CO_2$ asphyxiation), blood is collected either from a tail vein of unanesthesized rats or from the retro-orbital sinus of unanesthesized mice, or from the vena cava of rats or mice at sacrifice into 0.5 ml serum separator tubes. The freshly collected samples are centrifuged for two minutes at 10,000×g at room temperature, and the serum supernatant is stored at −80° C. until analysis. Serum leptin concentration is determined using LINCO rat leptin RIA kit (Cat # RL-83K; double antibody method as specified by the manufacturer) available from LINCO, St Charles, Mo. The serum leptin lowering activity of the test compounds is determined by statistical analysis (unpaired t-test) of the mean serum leptin concentration between the test compound group and the vehicle-treated control group.

[3] Chronic assessment of anti-atherosclerotic efficacy in rabbits. To demonstrate the anti-atherosclerotic potential of a Formula I compound of this invention, their prodrugs and the salts of such compounds and prodrugs, anti-atherosclerotic effects of the can be determined by the amount of test compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean±SD for total plasma cholesterol concentration, HDL cholesterol concentration and/or triglyceride concentration. After group assignment, rabbits are dosed daily with test compound given as a dietary admix or on a small piece of gelatin based confection. Control rabbits receive only the dosing vehicle, be it the food or the gelatin confection. The cholesterol/coconut oil diet is continued along with the test compound administration throughout the study. Plasma cholesterol and/or triglyceride values can be determined at any point during the study by obtaining blood from the marginal ear vein. After 3–5 months, the rabbits are sacrificed and the aorta are removed from the thoracic arch to the branch of the iliac arteries. The aorta are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the compound-receiving group in comparison with the control rabbits.

Administration of the compounds of this invention their prodrugs and the salts of such compounds and prodrugs can be via any method which delivers such compounds systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate or where the patient is unable to ingest the drug.

In general an amount of a compound of this invention is used that is sufficient to achieve the therapeutic effect desired.

In general an effective dosage for the Formula I compounds of this invention, their prodrugs and the salts of such compounds and prodrugs is in the range of about 0.001 to about 100 mg/kg/day, preferably about 0.01 to about 10 mg/kg/day.

A dosage of the combination pharmaceutical agents to be used in conjuction with the ACC inhibitor is used that is effective for the indication being treated. Such dosages can be determined by standard assays such as those referenced above and provided herein. The combination agents may be administered simultaneously or sequentially in any order.

For example, typically an effective dosage for HMG-CoA reductase inhibitors is in the range of about 0.01 to about 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, e.g., atherosclerosis.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof or a salt of such compound or prodrugs and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of this invention can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other-or other compounds generally will be administered in a convenient formulation. The following formulation examples only are illustrative and are not intended to limit the scope of the present invention.

In the formulations which follow, "active ingredient" means a compound of this invention, or as appropriate a combination of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

Formulation 8: Soft Gelatin Capsule with Oil Formulation

| Ingredient | Quantity (mg/capsule) |
| --- | --- |
| Active ingredient | 10–500 |
| Olive Oil or Miglyol ™ Oil | 500–1000 |

The active ingredient above may also be a combination of agents.

Genereal Experimental Procedures

NMR spectra were recorded on a Varian XL-300 (Varian Co., Palo Alto, Calif.), a Bruker AM-300 spectrometer (Bruker Co., Billerica, Mass.), a Varian Unity 400 or a Bruker DRX500 (Bruker Co., Billerica, Mass.) at ambient temperature. Chemical shifts are expressed in parts per million (δ) relative to an external standard (tetramethylsilane). The peak shapes are denoted as follows: s, singlet; d, doublet, t, triplet, q, quartet, m, multiplet with the prefix br indicating a broadened signal. Mass spectra were obtained by (1) atmospheric pressure chemical ionization (APCI) in alternating positive and negative ion mode using a Fisons Platform II Spectrometer or a Micromass MZD Spectrometer (Micromass, Manchester, UK) or (2) electrospray ionization in alternating positive and negative ion mode using a Micromass MZD Spectrometer (Micromass, Manchester, UK) with a Gilson LC-MS interface (Gilson Instruments, Middleton, Wis.). Where the intensity of chlorine- or bromine-containing ions are described, the expected intensity ratio was observed (approximately 3:1 for $^{35}Cl/^{37}Cl$-containing ions and 1:1 for $^{79}Br/^{81}Br$-containing ions) and the position of only the lower mass ion is given. It was generally found that the Formula I compounds exist as mixtures of amide rotamers which give rise to more complex NMR spectra. In these cases the NMR spectra described below may be incomplete and only clearly defined signals are provided.

Column chromatography was performed with either Baker Silica Gel (40 μm) (J. T. Baker, Phillipsburg, N.J.) or Silica Gel 60 (40–63 μm)(EM Sciences, Gibbstown, N.J.). Flash chromatography was performed using a Flash 40 column (Biotage, Dyar Corp., Charlotteville, Va.). Radial chromatography was performed using a Chromatron (model 7924T, Harrison Research, Palo Alto, Calif.). Unless otherwise specified, reagents were used as obtained from commercial sources. Dimethylformamide, tetrahydrofuran, toluene and dichloromethane were the anhydrous grade supplied by Aldrich Chemical Company (Milwaukee, Wis.). The terms "concentrated and "evaporated" refer to removal of solvent at 5–200 mm of mercury pressure on a rotary evaporator with a bath temperature of less than 45° C. The abbreviation "min" and "h" stand for "minutes" and "hours" respectively.

Intermediate 1

(3R)-[1,4']Bipiperidinyl-3,1'-dicarboxylic acid 1'-tert-butyl ester 3-ethyl ester To a mixture of tert-butyl 4-oxo-1-piperidinecarboxylate (12.40 g, 62.2 mmol) and (R)-ethyl nipecotate (1.05 eq, 65.3 mmol, 10.27 g) was added titanium tetraisopropoxide (1.25 eq, 23 mL) under nitrogen. A viscous, clear golden yellow solution was formed. After 1 h a solution of sodium cyanoborohydride (0.7 eq, 2.74 g) in anhydrous ethanol (65 mL) was added. An exothermic reaction took place and some gas evolution occurred. The solution was stirred overnight at ambient temperature then water (13 mL) was added slowly, along with additional ethanol as necessary to permit stirring to continue. The mixture was stirred for 30 minutes then filtered through a large pad of Celite®, washing through with ethanol. The filtrate was evaporated to dryness, toluene added and again evaporated to dryness. The residue was purified by chromatography on 150 g silica gel eluting with 5% methanol-dichloromethane. Fractions containing product were combined and evaporated to dryness to give an oil which became semi-solid on standing. The product was dissolved in dichloromethane, washed with dilute sodium hydroxide solution to remove titanium-containing impurities, dried over anhydrous sodium sulfate and evaporated to yield the title compound as a colorless oil, 21.14 g (containing a small amount of the isopropyl ester from transesterification).

MS: 341.3 [M+H]$^+$ found $^1$H-NMR (CDCl$_3$) δ 4.12 (brs, 2H), 4.08 (q, 2H, J=7.1 Hz), 2.98–2.89 (m, 1H) 2.69–2.55 (m, 2H), 2.54–2.45 (m, 1H), 2.45–2.28 (m, 2H), 2.22–2.12 (m, 1H), 1.94–1.84 (m, 1H), 1.77–1.65 (m, 4H), 1.57–1.34 (m, 4H), 1.41 (s, 9H), 1.24 (t, 3H, J=7.1 Hz).

Intermediate 2

(3R)-[1,4']Bipiperidinyl-3-carboxylic acid ethyl ester bishydrochloride

[1,4']Bipiperidinyl-3,1'-dicarboxylic acid 1'-tert-butyl ester 3-ethyl ester (21.14 g, containing some isopropyl ester) was dissolved in ethyl acetate (80 mL) under nitrogen, cooled to −78° C. and hydrogen chloride passed in for several minutes until the solution became saturated. The solution was allowed to warm to ambient temperature with provision for the evolved gases to be trapped by water in a scrubber. After 3 hr the solution was evaporated to dryness in a stream of dry nitrogen to give the title compound as a white solid.

MS: 241.3 [M+H]$^+$ found

Intermediate 3

Anthracene-9-carbonyl chloride

Anthracene-9-carboxylic acid (recrystallized from ethanol, 12.05 g, 54.3 mmol) was suspended in a mixture of chloroform (60 mL, Aldrich, amylenes-stabilized) and thionyl chloride (12 mL) and heated under reflux until a clear solution was obtained (about 30 minutes). The solvent was removed by distillation under reduced pressure and the residual hot oil was dissolved in toluene (20 mL) and hexane (100 mL) was added. After cooling to ambient temperature the crystalline product was collected by filtration and dried in a stream of nitrogen then under high vacuum to give the title compound as a yellow solid (7.69 g, 59%). Non-commercially available carboxylic acids referred to in this section were prepared as described below. If desired they were converted to the corresponding carbonyl chloride using thionyl chloride as described above.

Intermediate 4

9-Phenanthroic acid

9-Bromophenanthrene (7.78 mmol, 2.0 g), magnesium turnings (18.5 mmol, 0.45 g) and a crystal of iodine were added to anhydrous tetrahydrofuran (10 mL). The mixture was heated under reflux for 1 hr then allowed to cool. The mixture was decanted into a mixture of dry ice pellets under anhydrous tetrahydrofuran. A vigorous reaction occurred and a white precipitate was formed. The mixture was evaporated in a slow stream of nitrogen overnight then the residue was agitated with 2M hydrochloric acid. The solid was collected by filtration and recrystallized from ethanol to give the title compound (1.09 g, 63%).

MS: 221.2 [M-H]$^-$

Intermediate 5

2-Pyridin-4-yl-6-trifluoromethyl-quinoline-4-carboxylic acid

To a three-necked flask equipped with a stirring bar, thermometer and 2 addition funnels was added a solution of 4-trifluoromethylaniline (0.088 mol, 11.05 mL) in dichloromethane (300 mL). The solution was cooled to −70° C.

and a solution of t-butyl hypochlorite (0.088 mol, 9.95 mL) in dichloromethane (20 mL) was added dropwise over a period of 30 minutes maintaining the temperature at −60° C. The mixture was then stirred at −70° C. for 1 h and a solution of methylsulfanyl-acetic acid methyl ester (0.088 mol, 9.52 mL) in dichloromethane (20 mL) was added over a period of 30 minutes maintaining the temperature at −65° C. The reaction mixture was stirred for 1 hour at −70° C. Triethylamine (0.088 mol, 12.3 mL) was added dropwise and stirring at −70° C. continued for 30 minutes before allowing the mixture to warm to room temperature. After 1 hour at ambient temperature the dichloromethane was evaporated under vacuum and ether (200 mL) was added to the residue followed by water (150 mL). The ether layer was separated, 1N hydrochloric acid (50 mL) added and the mixture was stirred for 16 hr at room temperature. The organic layer was separated, dried over anhydrous sodium sulfate and the solvent removed under vacuum. The residue was purified by chromatography on silica gel eluting with dichloromethane followed by 19:1 dichloromethane-ethyl acetate then 9:1 dichloromethane-ethyl acetate to give 3-methylsulfanyl-5-trifluoromethyl-1,3-dihydro-indol-2-one as a yellow solid (12.9 g, 59%). N-Chlorosuccimide (1.5 eq, 4.87 g, 36.46 mmol) was added to a solution of 3-methylsulfanyl-5-trifluoromethyl-1,3-dihydro-indol-2-one (6 g, 24.29 mmol) in chloroform (100 mL). After stirring for 2 hours at room temperature the precipitate was removed by filtration through a pad of Celite® and the solvent was removed under vacuum. The residue was dissolved in tetrahydrofuran (30 mL) and added to a solution prepared from red mercury (II) oxide (1.0 eq., 5.26 g, 24.29 mmol) in a mixture of tetrahydrofuran (80 mL) and water (20 mL) to which was added boron trifluoride etherate (1.0 eq, 2.99 mL). The solution was stirred overnight at room temperature then filtered through a pad of Celite®, rinsing through with tetrahydrofuran. The solution was extracted with dichloromethane (4×100 mL) and the combined organic layers dried over anhydrous sodium sulfate and the solvent was removed under vacuum. The residue was purified by chromatography on silica gel eluting with 10% ethyl acetate-dichloromethane to give 5-trifluoromethyl-1H-indole-2,3-dione as a yellow solid (2.79 g, 53%). To a solution of 5-trifluoromethyl-1H-indole-2,3-dione (0.93 mmol, 200 mg) in ethanol (30 mL) was added 1M sodium hydroxide (15 mL) and the mixture was stirred for 30 min. 4-Acetylpyridine (1.02 mmol, 0.072 mL) was added and the solution was heated under reflux for 16 hr. After cooling the mixture was extracted with diethyl ether and the organic layer was dried over anhydrous sodium sulfate and the solvent was removed under vacuum. The residue was purified by chromatography on a 4 mm silica gel rotor eluting with 9:1 dichloromethane-methanol to give the title compound (300 mg, 100%).

The following carboxylic acids were prepared from commercially available anilines or isatins using an analogous procedure:

Intermediate 6

7-Trifluoromethyl-2-(4-trifluoromethyl-phenyl)-quinoline-4-carboxylic acid

Intermediate 7

2-(4-Chloro-phenyl)-6-fluoro-quinoline-4-carboxylic acid

Intermediate 8

2-(4-Chloro-phenyl)-6-trifluoromethoxy-quinoline-4-carboxylic acid

Intermediate 9

2-(4-Chloro-phenyl)-6-methyl-quinoline-4-carboxylic acid

Intermediate 10

2-(3,5-Bis-trifluoromethyl-phenyl)-6-fluoro-quinoline-4-carboxylic acid

Intermediate 11

2-(2,6-Difluoro-phenyl)-6-fluoro-quinoline-4-carboxylic acid

Intermediate 12

3-Methyl-2-phenyl-quinoline-4-carboxylic acid (from isatin and propiophenone)

Intermediate 13

6-Trifluoromethyl-2-(4-trifluoromethyl-phenyl)-quinoline-4-carboxylic acid

4-Trifluoromethylaniline (0.015 mmol, 1.88 mL), pyruvic acid (1.0 eq, 0.015 mmol, 2.04 mL) and 4-trifluoromethylbenzaldehyde were dissolved in acetic acid (10 mL). Concentrated sulfuric acid (10 mL) was cautiously added (exothermic) and stirred for 30 minutes. Chloroform (50 mL) and water (50 mL) were added followed by ammonium hydroxide until the solution was basic to pH paper. The layers were separated and the aqueous solution was extracted with chloroform (3×50 mL). The combined organic layers were dried over anhydrous sodium sulfate and the solvent was evaporated under vacuum. The solid residue was purified by recrystallization from 95% ethanol to give the title compound as a yellow solid (580 mg, 10%).

EXAMPLE 1

(3R)-1'-(Anthracene-9-carbonyl)-[1,4']bipiperidinyl-3-carboxylic acid ethyl ester Anthracene-9-carbonyl chloride (62.2 mmol) was suspended in anhydrous dichloromethane (30 mL) and added slowly by pipette to a solution of [1,4']bipiperidinyl-3-Carboxylic acid ethyl ester bishydrochloride (62.2 mmol) and triethylamine (4 eq., 35 mL) in anhydrous dichloromethane (50 mL) at such a rate that a gentle reflux was maintained. The resulting suspension was stirred overnight at ambient temperature then shaken with ice-cold water containing sodium hydroxide (0.19 mol, 7.6 g). The dichloromethane layer was separated and the aqueous layer was extracted with dichloromethane. The combined dichloromethane solution was washed with water, dried with anhydrous sodium sulfate, diluted with a little xylene and evaporated to dryness to give the title compound (containing a small amount of the corresponding isopropyl ester) as a pale yellow gummy foam (30.8 g).

MS: 445.4 [M+H]+ (ethyl ester) and 459.4 [M+H]+ (isopropyl ester) found $R_F$ 0.29 (19:1 dichloromethane-methanol) $^1$H-NMR (CDCl$_3$) δ 8.44 (s, 1H), 8.09–7.90 (m, 3H), 7.85–7.75 (m, 1H), 7.60–7.40 (m, 4H), 5.17 (brd, 1H, J=13.2 Hz), 4.17–4.04 (m, 2H), 3.20 (dm, 1H, J=13.5 Hz), 3.06–2.92 (m, 2H), 2.87 (tm, 1H, J=13.0 Hz), 2.80–2.67 (m, 1H), 2.56–2.43 (m, 2H), 2.39–2.28 (m, 1H), 2.21–2.11 (m, 1H), 2.11–2.03 (m, 1H), 1.96–1.83 (m, 2H), 1.78–1.65 (m, 2H), 1.58–1.36 (m, 3H), 1.27–1.15 (m, 3H).

EXAMPLE 2

(3R)-1'-[2,6-Bis-(4-chloro-phenyl)-pyridine-4-carbonyl]-[1,4']bipiperidinyl-3-carboxylic acid ethyl ester The title compound was obtained from (3R)-[1,4'] bipiperidinyl-3-Carboxylic acid ethyl ester bishydrochloride by procedures similar to those described above using 2,6-bis-(4-Chloro-phenyl)-isonicotinic acid (P. Blumbergs et al. *J. Med. Chem.* 1972, 15, 808.)

MS: 566.0 [M+H]+

EXAMPLE 3

(3R)-1'-[2,6-Diphenyl-pyridine-4-carbonyl]-[1,4'] bipiperidinyl-3-carboxylic acid ethyl ester The title compound was obtained from (3R)-[1,4'] bipiperidinyl-3-carboxylic acid ethyl ester bishydrochloride by procedures similar to those described above using 2,6-diphenyl-isonicotinic acid which was prepared according to a procedure analogous to that described by P. Blumbergs et al. *J. Med. Chem.* 1972, 15, 808.

MS: 498.1 [M+H]+

EXAMPLE 4

(3R)-1'-(Anthracene-9-carbonyl)-[1,4']bipiperidinyl-3-carboxylic acid (3R)-1'-(Anthracene-9-carbonyl)-[1,4']bipiperidinyl-3-carboxylic acid ethyl ester (containing a small amount of the corresponding isopropyl ester) (10 g, approx. 22 mmol) was dissolved with warming in dioxane (50 mL) and 2N hydrochloric acid (50 mL) was added. The clear yellow solution was heated at 110° C. (slight reflux) and a pinkish red color soon developed. After 165 min the solution was allowed to cool to ambient temperature. After standing overnight the dioxane was evaporated and an oily solid precipitated out. The mixture was washed with dichloromethane and the insoluble oil was separated from the aqueous layer, dissolved in a dioxane-water mixture (100 mL), xylene (100 mL) was added and the mixture was evaporated to dryness, finally under high vacuum, to give the title compound as a yellow foam which was used in the following procedure without further purification.

$R_F$ 0.50 (7:3 dichloromethane-methanol) MS: 417.3 [M+H]+

EXAMPLE 5

(3R)-Anthracen-9-yl-[3-(morpholine-4-carbonyl)-[1,4']bipiperidinyl-1'-yl]-methanone The crude (3R)-1'-(anthracene-9-carbonyl)-[1,4'] bipiperidinyl-3-carboxylic acid as prepared above (approx 22 mmol) was heated under reflux in a mixture of chloroform (75 mL, Aldrich, amylenes-stabilized) and thionyl chloride (10 mL, 0.137 mmol) until all the solid had dissolved. The mixture was diluted with toluene, evaporated to dryness under vacuum and anhydrous dichloromethane (40 mL) added. A mixture of morpholine (21 mmol, 1.81 mL) and triethylamine (62 mmol, 8.7 mL) in anhydrous dichloromethane (40 mL) was added and the solution was stirred for 16 hr at ambient temperature. The mixture was washed with ice-cold 0.1M sodium hydroxide solution, dried over anhydrous sodium sulfate, diluted with toluene and evaporated to dryness. The residue was purified by chromatography on 240 g silica gel eluting with a 4%–7%–10% methanol-dichloromethane gradient to give the title compound as a pale yellow glassy foam.

$R_F$ 0.25 (9:1 dichloromethane-methanol) MS: 486.4 [M+H]+ $^1$H-NMR (CDCl$_3$) δ 8.43 (s, 1H), 8.02–7.91 (m, 3H), 7.84–7.76 (m, 1H), 7.54–7.38 (m, 4H), 5.20 (dm, 1H, J=13.4 Hz), 3.67–3.50 (m, 6H), 3.49–3.39 (m, 2H), 3.15 (dm, 1H, J=13.4 Hz), 3.04–2.77 (m, 4H), 2.66 (tm, 1H, J=10.9 Hz), 2.48 (tm, 1H, J=11.2 Hz), 2.36 (t, 1H, J=10.9 Hz), 2.16–2.02 (m, 2H), 1.81–1.61 (m, 3H), 1.61–1.38 (m, 3H), 1.35–1.16 (m, 1H). $^{13}$C-NMR (CDCl$_3$) δ 172.57, 168.26, 168.24, 130.99, 130.85, 130.63, 130.61, 128.45, 127.44, 127.33, 127.20, 126.52, 126.48, 125.40, 125.37, 125.33, 124.69, 124.67, 124.51, 66.68, 66.58, 62.22, 52.17, 52.05, 49.18, 49.06, 46.16, 45.68, 41.67, 40.93, 40.89, 39.35, 39.31, 29.11, 28.84, 28.26, 28.04, 27.77, 25.07.

Intermediate 14

4-[1'-(2,6-Diphenyl-pyridine-4-carbonyl)-[1,4'] bipiperidinyl-3-carbonyl]-piperazine-1-carboxylic acid tert-butyl ester (3R)-1'-[2,6-Diphenyl-pyridine-4-carbonyl]-[1,4'] bipiperidinyl-3-carboxylic acid ethyl ester (1.96 g, 3.94 mmol) was dissolved in tetrahydrofuran (20 mL) and lithium hydroxide monohydrate (3 eq, 0.5 g) in water (10 mL) was added. The two phase mixture was stirred for 16 hr at ambient temperature. Thin layer chromatography (19:1 dichloromethane-methanol) indicated no remaining starting material. 2M hydrochloric acid (6 mL) was added to adjust the pH to ~5, about 2× the volume of the xylene was added and the mixture was evaporated to give a pale oil. This was further dried briefly under high vacuum then suspended in ethanol-free chloroform (~30 mL), thionyl chloride added (5 mL) and the mixture heated under reflux, directing the evolved gases to a scrubber. After 30 minutes a further aliquot of thionyl chloride (5 mL) and chloroform (20 mL) were added and the reflux continued. After all the solid had dissolved (~2 hr) the solvent was evaporated under vacuum. Anhydrous dichloromethane (30 mL) was added followed by a mixture of tert-butyl 1-piperazinecarboxylate (1.1 eq, 810 mg) and N,N-diisopropylethylamine (5 eq, 3.4 mL) in anhydrous dichloromethane (10 mL) was added. The cloudy mixture was stirred for 16 hr at ambient temperature then washed with 0.1M sodium hydroxide solution and the aqueous layer was extracted with dichloromethane (×3). The combined organic layers were dried over anhydrous sodium sulfate and evaporated to dryness under vacuum. The residue was purified by chromatography on 100 g silica gel/5% methanol-dichloromethane to give the title compound (1.78 g, 71%).

$R_F$ 0.39 (9:1 dichloromethane-methanol) MS: 638.3 [M+H]+ $^1$H-NMR (CDCl$_3$) δ 8.13 (d, 4H, J=7.5 Hz), 7.62 (s, 2H), 7.53–7.40 (m, 6H), 4.81 (brd, 1H, J=12.9 Hz), 3.78 (brd, 1H, J=12.9 Hz), 3.64–3.50 (m, 2H), 3.49–3.31 (m, 7H), 3.04 (brt, 1H, J=12.5 Hz), 2.95–2.85 (m, 2H), 2.84–2.63 (m, 2H), 2.56 (brt, 1H, J=11.2 Hz), 2.42 (brt, 1H, J=10.8 Hz)

2.18 (brt, 1H, J=10.8 Hz), 1.98 (brd, 1H, J=12.4 Hz), 1.89–1.70 (m, 4H), 1.68–1.51 (m, 2H), 1.45 (s, 9H).

EXAMPLE 6

(3R)-anthracen-9-yl-[3-(morpholine-4-carbonyl)-[1,4']bipiperidinyl-1'-yl]-methanone hydrochloride The free base was converted to its hydrochloride salt by dissolving in a mixture of dichloromethane (10 mL), ethyl acetate (30 mL) and diethyl ether (30 mL). The solution was cooled to –78° C. under nitrogen and a freshly prepared solution of hydrogen chloride in diethyl ether was added until precipitation was complete. A mixture of diethyl ether and hexane (1:1) was added as necessary to keep the suspension mobile. The solid was collected by filtration under a positive pressure of nitrogen and dried under high vacuum to give the title compound, 5.35 g (53% based on (3R)-[1,4']bipiperidinyl-3,1'-dicarboxylic acid 1'-tert-butyl ester 3-ethyl ester, 5 steps).

Intermediate 15

(3R)-Piperidine-1,3-dicarboxylic acid 1-tert-butyl ester

To a stirred suspension of (3R)-ethyl nipecotate (120 mmol, 18.96 g) in saturated sodium hydrogen carbonate solution (100 mL) was added di-tert-butyl dicarbonate (1 eq, 120 mmol, 26.32 g). The di-tert-butyl dicarbonate was washed into the mixture with 20 mL of ethyl acetate. The mixture was stirred in a water bath maintained at 10–15° C. The pH of the mixture was maintained at pH 9–10 by addition of 2M sodium hydroxide solution (pH paper). A total of about 20 mL of 2N sodium hydroxide was added. A white crystalline precipitated was formed. After 90 minutes the precipitate was filtered off and washed with a little water and the two phase mixture extracted with ethyl acetate. The organic layer was washed with water and diluted hydrochloric acid and the organic layer was dried over anhydrous sodium sulfate and evaporated under vacuum to a colorless oil. To the oil solution was added a solution of lithium hydroxide monohydrate (2 eq, 10.2 g) in water (250 mL) and tetrahydrofuran (100 mL) was added. After approximately 1 h the solution became clear. The mixture was stirred for 16 hr at ambient temperature then the tetrahydrofuran was evaporated under vacuum. Concentrated hydrochloric acid was added until the solution was strongly acidic. The white crystalline solid was collected by filtration, rinsed with water and dried under high vacuum to give the title compound (26.16 g, 95%).

Intermediate 16

(3R)-Morpholin-4-yl-piperidin-3-yl-methanone (3R)-Piperidine-1,3-dicarboxylic acid 1-tert-butyl ester (2.64 g, 11.5 mmol), benzotriazo-1-yloxytris(dimethylamino)phosphonium hexafluorophosphate (BOP, 1.1 eq., 5.61 g) and 1-hydroxybenzotriazole hydrate (0.1 eq., 180 mg) were dissolved in anhydrous dichloromethane (30 mL) under nitrogen and morpholine (1.1 eq., 1.11 mL) was added followed by triethylamine (3 eq., 4.82 mL). The solution briefly came to reflux and was then allowed to stir for 16 hr at ambient temperature. The solution was washed with 0.2M sodium hydroxide solution (×2), dried over anhydrous sodium sulfate and the solvent was removed under vacuum. The residue was dissolved in anhydrous toluene and the solvent again removed under vacuum. The product was purified by chromatography on silica gel eluting with a 5% to 10% methanol in dichloromethane gradient. The product was dissolved in ethyl acetate (30 mL), saturated with hydrogen chloride at –78° C. then stirred at room temperature for 1 hr. The solvent was evaporated in a stream of dry nitrogen. The solid residue was dissolved in water (~5 mL) followed by sodium hydroxide (1 g). Xylene was added and the solvent was removed under vacuum. The residue was extracted with dichloromethane, the organic solution was filtered through Celite® and the solvent was evaporated under vacuum to give the title compound as a colorless oil which crystallized on refrigeration (2.25 g, 100%).

MS: 199.2 [M+H]$^+$

Intermediate 17

(3R)-[1,4']Bipiperidinyl-3-yl-morpholin-4-yl-methanone bishydrochloride (3R)-Morpholin-4-yl-piperidin-3-yl-methanone (2.25 g, 11.4 mmol) was reacted with tert-butyl 4-oxo-1-piperidinecarboxylate (1 eq., 2.27 g) under conditions analogous to those described above for the preparation of Intermediate 1 to give (3R)-3-(morpholine-4-carbonyl)-[1,4']bipiperidinyl-1'-carboxylic acid tert-butyl ester (3.00 g, 69%).

$^1$H-NMR (CDCl$_3$) δ 4.29–3.94 (brs, 2H), 3.66–3.61 (m, 4H), 3.61–3.54 (m, 2H), 3.51–3.46 (m, 2H), 2.86 (brd, 2H, J=10.8 Hz), 2.73–2.58 (m, 3H), 2.46–2.35 (m, 2H), 2.15 (brt, 1H, J=11.6 Hz), 1.80–1.69 (m, 4H), 1.60–1.35 (m, 4H), 1.42 (s, 9H).

The t-butylcarbamyl group was removed using a procedure similar to that described above for the preparation of Intermediate 2 to give the title compound as an off-white solid (3.05 g).

Intermediate 18

Piperidine-3-carboxylic acid benzyl ester

Piperidine-1,3-dicarboxylic acid 1-tert-butyl ester was prepared from racemic ethyl nipecotate by an exactly analogous route to that described for the preparation of Intermediate 15. A suspension of benzaldehyde tosylhydrazone (0.5 g, 1.82 mmol) and benzyltriethylammonium chloride (100 mg) in a mixture of toluene (50 mL) and sodium hydroxide solution (14% w/v, 50 mL) was heated under a nitrogen atmosphere at 70±5° C. for 1.25 h. The mixture was cooled in ice then transferred to a separating funnel. The lower layer was removed and the pink organic layer washed with ice water (×2) then briefly dried over anhydrous sodium sulfate. This solution of phenyldiazomethane was added to a suspension of piperidine-1,3-dicarboxylic acid 1-tert-butyl ester (1.82 mmol, 420 mg) in dichloromethane (20 mL). The pink color was rapidly discharged. The reaction mixture was shaken with 0.1M sodium hydroxide (×2), dried over anhydrous sodium sulfate and evaporated to an oil. This was purified by chromatography on silica gel eluting with 3% methanol/dichloromethane to give piperidine-1,3-dicarboxylic acid 3-benzyl ester 1-tert-butyl ester (580 mg, 100%). This material was dissolved in ethyl acetate (~50 mL) cooled to –78° C. under nitrogen and hydrogen chloride passed in for a few minutes. The solution was allowed to warm to ambient temperature then evaporated in a stream of nitrogen overnight (effluent gas passing into a water scrubber). The solid residue was dissolved in water, a small amount of 0.1M hydrochloric acid added and extracted with dichloromethane (×3). 2 N sodium hydroxide was added until cloudiness persisted (pH>13) then the mixture was extracted with dichloromethane (×3). The organic phase was dried over anhydrous sodium sulfate and the solvent was evaporated under vacuum to give the title compound (287 mg, 72%).

MS: 220.3 [M+H]$^+$

Intermediate 19

[1,4']Bipiperidinyl-3-carboxylic acid benzyl/isopropyl esters

A mixture of piperidine-3-carboxylic acid benzyl ester (287 mg, 1.31 mmol), tert-butyl 4-oxo-1-piperidinecarboxylate (1 eq., 261 mg) and titanium (IV) isopropoxide (1.25 eq, 1.64 mmol, 485 µl) was stirred at room temperature for 1 h. Sodium cyanoborohydride (0.7 eq, 0.92 mmol, 58 mg) in anhydrous ethanol (3 mL) was added. After stirring at room temperature for 24 h water (0.5 mL) was added to produce a white precipitate. The suspension was filtered through Celite®, rinsing through with ethanol and the solvent was evaporated to give a nearly colorless oil. HPLC/MS indicated that the product contained a significant amount of isopropyl ester by titanium (IV) isopropoxide-induced transesterification. The product was purified by chromatography on silica gel eluting with 2% methanol/dichloromethane containing 2 drops of concentrated ammonium hydroxide per 100 mL. The benzyl ester (88.4 mg, 16.8%) eluted first followed by fractions containing the slightly more polar isopropyl ester (146.3 mg, 27.8%). Both compounds were deprotected in a similar manner to that described above for piperidine-3-carboxylic acid benzyl ester to give the title compounds as their hydrochloride salts.

Intermediate 20

1-(1-tert-Butoxycarbonyl-azetidin-3-yl)-piperidine-3-carboxylic acid ethyl ester Methanesulfonic acid 1-benzhydryl-azetidin-3-yl ester (A. G. Anderson, Jr. and R. Lok, *J. Org. Chem.*, 1972, 37, 3953)(2.22 g, 7 mmol) and ethyl nipecotate (1.0 g, 6.37 mmol) were dissolved in dimethylformamide (3 mL) and heated at 110° C. for 1 hr. The mixture was cooled to ambient temperature, diluted with water and extracted with dichloromethane (3×15 mL). The extract was dried over anhydrous magnesium sulfate and the solvent removed under vacuum to give an impure sample of 1-(1-benzhydryl-azetidin-3-yl)-piperidine-3-carboxylic acid ethyl ester (2.91 g).

$R_F$ 0.45 (1:1 ethyl acetate:hexanes)

Without further purification this material was dissolved in 1,2-dichloroethane (30 mL) and 1-Chloroethyl chloroformate (0.91 mL, 8.44 mmol) was added. The mixture was heated under reflux for 2 hr and the solvent was removed under vacuum. Methanol (50 mL) was added and the solution was heated under reflux for 1 hr. The solvent was removed under vacuum to give a dark-colored oil which was dissolved in a mixture of dichloromethane (10 mL) and triethylamine (3 eq., 3.21 mL, 23 mmol). After 10 min the flask was placed in an ice bath and di-tert-butyl dicarbonate (2 eq., 15.34 mmol, 3.35 g) in dichloromethane (10 mL) was added over 5 min. The cooling bath was removed and the mixture was allowed to warm to ambient temperature. Water was added, the aqueous layer was separated and extracted with dichloromethane (×3). The combined organic layers was dried over anhydrous magnesium sulfate and the solvent was removed under vacuum. The residue was purified by chromatography on silica gel eluting with 1:1 ethyl acetate-hexanes to give 1-(1-tert-butoxycarbonyl-azetidin-3-yl)-piperidine-3-carboxylic acid ethyl ester (620 mg, 26%).

$R_F$ 0.40 (1:1 ethyl acetate:hexanes)

Intermediate 21

(3R)-1-(1-tert-Butoxycarbonyl-azetidin-3-yl)-piperidine-3-carboxylic acid ethyl ester The title compound was prepared by an exactly analogous procedure to that used for the preparation of Intermediate 20 using R-ethyl nipecotate.

EXAMPLE 7

(3R)-Anthracen-9-yl-{3-[3-(morpholine-4-carbonyl)-piperidin-1-yl]-azetidin-1-yl}-methanone To a solution of (3R)-1-(1-tert-butoxycarbonyl-azetidin-3-yl)-piperidine-3-carboxylic acid ethyl ester (22.8 mmol, 7.1 g) in tetrahydrofuran (120 mL) was added a solution of lithium hydroxide monohydrate (3 eq, 4 mmol, 2.87 g) in water (69 mL). The mixture was stirred at room temperature until all of the ester had been hydrolyzed, monitoring the progress of the reaction by thin layer chromatography (10% methanol/dichloromethane). After 3 hours the mixture was adjusted to pH8 by the addition of 2N hydrochloric acid (2 eq, 22.8 mL, 45.6 mmol) and the solvent removed under vacuum to give an oil. Toluene was added and evaporated under vacuum (3×) to remove water and the residue was further dried under high vacuum to give the lithium salt of (3R)-1-(1-tert-butoxycarbonyl-azetidin-3-yl)-piperidine-3-carboxylic acid as a white solid (10.8 g).

A portion of this material (5 g, 10.5 mmol), N,N-diisopropylethylamine (4 eq, 42 mmol, 7.3 mL) and 3-(diethoxyphosphoryloxy)-1,2,3-benzotriazin-4(3H)-one (2 eq, 21 mmol, 6.3 g) were suspended in dichloromethane (100 mL) and dimethylformamide was added to give an homogenous solution (~10 mL). The solution was stirred for 1 hour at room temperature during which time a white precipitate formed. Morpholine (1 eq, 10.5 mmol, 915 µl) was added and the mixture was stirred at room temperature for 10 minutes. The mixture was diluted with dichloromethane and washed with water (×2). The organic layer was washed with saturated sodium hydrogen carbonate, brine, dried over anhydrous sodium sulfate and concentrated to a yellow oil. This was purified by flash chromatography (2.5%–10% methanol/dichloromethane) to give (3R)-3-[3-(morpholine-4-carbonyl)-piperidin-1-yl]-azetidine-1-carboxylic acid tert-butyl ester as a viscous yellow oil (3.3 g, 89%).

$R_F$ 0.48 (10% methanol/dichloromethane).

The title compound was prepared from this compound using a procedure analogous to those described above for the preparations of Intermediate 2 followed by the preparation of Example 1.

$R_F$ 0.46 (9:1 dichloromethane-methanol) MS: 458.4 [M+H]$^+$ $^1$H-NMR (CDCl$_3$) δ 8.47 (s, 1H), 8.07–7.97 (m, 4H), 7.56–7.45 (m, 4H), 4.49 (t, 1H, J=10.0 Hz), 4.31–4.17 (m, 1H), 3.74–3.33 (m, 10 H), 3.30–3.17 (m, 1H), 2.92–2.81 (m, 1H), 2.80–2.57 (s, 1H), 2.56–2.44 (s, 1H), 2.17–1.93 (s, 1H), 1.90–1.73 (m, 2H), 1.72–1.61 (m, 1H), 1.54–1.3 (m, 2H).

The following Intermediate and Examples were prepared from either (3R)- or racemic 1'-(anthracene-9-carbonyl)-[1, 4']bipiperidinyl-3-carboxylic acid and an amine (commercially available except where indicated otherwise) by a reaction analogous to that described above for the preparation of Example 5:

Intermediate 22

(3R)-1'-(Anthracene-9-carbonyl)-[1,4']bipiperidinyl-3-carboxylic acid diethylamide $R_F$ 0.30 (9:1 dichloromethane-methanol) MS: 472.3 $[M+H]^+$

EXAMPLE 8

1'-(Anthracene-9-carbonyl)-[1,4']bipiperidinyl-3-carboxylic acid amide $R_F$ 0.25 (9:1 dichloromethane-methanol) MS: 416.5 $[M+H]^+$

EXAMPLE 9

1'-(Anthracene-9-carbonyl)-[1,4']bipiperidinyl-3-carboxylic acid ethylamide $R_F$ 0.31 (9:1 dichloromethane-methanol) MS: 444.5 $[M+H]^+$

EXAMPLE 10

1'-(Anthracene-9-carbonyl)-[1,4']bipiperidinyl-3-carboxylic acid dipropylamide $R_F$ 0.43 (9:1 dichloromethane-methanol) MS: 500.4 $[M+H]^+$

EXAMPLE 11

Anthracen-9-yl-[3-(pyrrolidine-1-carbonyl)-[1,4']bipiperidinyl-1'-yl]-methanone $R_F$ 0.34 (9:1 dichloromethane-methanol) MS: 470.4 $[M+H]^+$

EXAMPLE 12

Anthracen-9-yl-[3-(piperidine-1-carbonyl)-[1,4']bipiperidinyl-1'-yl]-methanone $R_F$ 0.38 (9:1 dichloromethane-methanol) MS: 484.4 $[M+H]^+$

EXAMPLE 13

(3R)-1'-(Anthracene-9-carbonyl)-[1,4']bipiperidinyl-3-carboxylic acid dimethylamide $R_F$ 0.27 (9:1 dichloromethane-methanol) MS: 444.3 $[M+H]^+$

EXAMPLE 14

(3R)-1'-(Anthracene-9-carbonyl)-[1,4']bipiperidinyl-3-carboxylic acid tert-butyl-amide $R_F$ 0.34 (9:1 dichloromethane-methanol) MS: 472.3 $[M+H]^+$

EXAMPLE 15

(3R)-1'-(Anthracene-9-carbonyl)-[1,4']bipiperidinyl-3-carboxylic acid ethyl-methyl-amide $R_F$ 0.28 (9:1 dichloromethane-methanol) MS: 458.4 $[M+H]^+$

EXAMPLE 16

(3R)-1'-(Anthracene-9-carbonyl)-[1,4']bipiperidinyl-3-carboxylic acid diisopropylamide $R_F$ 0.34 (9:1 dichloromethane-methanol) MS: 500.5 $[M+H]^+$

EXAMPLE 17

(3R)-1'-(Anthracene-9-carbonyl)-[1,4']bipiperidinyl-3-carboxylic acid (2,2,2-trifluoro-ethyl)-amide $R_F$ 0.41 (9:1 dichloromethane-methanol) MS: 498.2 $[M+H]^+$

EXAMPLE 18

(3R)-1'-(Anthracene-9-carbonyl)-[1,4']bipiperidinyl-3-carboxylic acid methylamide $R_F$ 0.22 (9:1 dichloromethane-methanol) MS: 430.3 $[M+H]^+$

EXAMPLE 19

1'-(Anthracene-9-carbonyl)-[1,4']bipiperidinyl-3-carboxylic acid diisobutylamide

MS: 528.8 $[M+H]^+$

EXAMPLE 20

1'-(Anthracene-9-carbonyl)-[1,4']bipiperidinyl-3-carboxylic acid bis-(2-methoxy-ethyl)-amide

MS: 532.2 $[M+H]^+$

EXAMPLE 21

Anthracen-9-yl-[3-(2,6-dimethyl-morpholine-4-carbonyl)-[1,4']bipiperidinyl-1'-yl]-methanone

MS: 514.1 $[M+H]^+$

EXAMPLE 22

(3R)-1'-(Anthracene-9-carbonyl)-[1,4']bipiperidinyl-3-carboxylic acid (2,2-dimethyl-propyl)-amide $R_F$ 0.38 (9:1 dichloromethane-methanol) MS: 486.0 $[M+H]^+$

EXAMPLE 23

1'-(Anthracene-9-carbonyl)-[1,4']bipiperidinyl-3-carboxylic acid dicyclohexylamide

MS: 580.3 $[M+H]^+$

EXAMPLE 24

1-[1'-(Anthracene-9-carbonyl)-[1,4']bipiperidinyl-3-carbonyl]-pyrrolidine-2-carboxylic acid amide

MS: 513.2 $[M+H]^+$

EXAMPLE 25

1'-(Anthracene-9-carbonyl)-[1,4']bipiperidinyl-3-carboxylic acid tert-butyl-methyl-amide

MS: 487.1 $[M+H]^+$

EXAMPLE 26

1'-(Anthracene-9-carbonyl)-[1,4']bipiperidinyl-3-carboxylic acid (3,5-difluoro-phenyl)-amide

MS: 528.1 [M+H]$^+$

EXAMPLE 27

Anthracen-9-yl-[3-(thiomorpholine-4-carbonyl)-[1,4']bipiperidinyl-1'-yl]-methanone

MS: 502.1 [M+H]$^+$

EXAMPLE 28

1'-(Anthracene-9-carbonyl)-[1,4']bipiperidinyl-3-carboxylic acid (4-trifluoromethyl-phenyl)-amide

MS: 560.1 [M+H]$^+$

EXAMPLE 29

1'-(Anthracene-9-carbonyl)-[1,4']bipiperidinyl-3-carboxylic acid diphenylamide

MS: 568.1 [M+H]$^+$

EXAMPLE 30

Anthracen-9-yl-[3-(2-methyl-2,3-dihydro-indole-1-carbonyl)-[1,4']bipiperidinyl-1'-yl]-methanone

MS: 532.1 [M+H]$^+$

EXAMPLE 31

1'-(Anthracene-9-carbonyl)-[1,4']bipiperidinyl-3-carboxylic acid bicyclo[2.2.1]hept-2-ylamide

MS: 510.2 [M+H]$^+$

EXAMPLE 32

1-[1'-(Anthracene-9-carbonyl)-[1,4']bipiperidinyl-3-carbonyl]-piperidine-2-carboxylic acid ethyl ester

MS: 556.2 [M+H]$^+$

EXAMPLE 33

1'-(Anthracene-9-carbonyl)-[1,4']bipiperidinyl-3-carboxylic acid (1-methyl-1-phenyl-ethyl)-amide

MS: 534.2 [M+H]$^+$

EXAMPLE 34

1'-(Anthracene-9-carbonyl)-[1,4']bipiperidinyl-3-carboxylic acid (2-cyano-ethyl)-cyclopentyl-amide

MS: 537.3 [M+H]$^+$

EXAMPLE 35

1'-(Anthracene-9-carbonyl)-[1,4']bipiperidinyl-3-carboxylic acid (2-cyano-ethyl)-cyclopropyl-amide

MS: 509.2 [M+H]$^+$

EXAMPLE 36

1'-(Anthracene-9-carbonyl)-[1,4']bipiperidinyl-3-carboxylic acid (3-acetylamino-phenyl)-amide

MS: 549.2 [M+H]$^+$

EXAMPLE 37

1'-(Anthracene-9-carbonyl)-[1,4']bipiperidinyl-3-carboxylic acid adamantan-1-ylamide

MS: 550.3 [M+H]$^+$

EXAMPLE 38

Anthracen-9-yl-[3-(3,6-dihydro-2H-pyridine-1-carbonyl)-[1,4']bipiperidinyl-1'-yl]-methanone

MS: 482.2 [M+H]$^+$

EXAMPLE 39

Anthracen-9-yl-[3-(2-methyl-3,4-dihydro-2H-quinoline-1-carbonyl)-[1,4']bipiperidinyl-1'-yl]-methanone

MS: 546.2 [M+H]$^+$

EXAMPLE 40

[1'-(Anthracene-9-carbonyl)-[1,4']bipiperidinyl-3-yl]-(dodecahydro-carbazol-9-yl)-methanone

MS: 578.4 [M+H]$^+$

EXAMPLE 41

N-{1-[1'-(Anthracene-9-carbonyl)-[1,4']bipiperidinyl-3-carbonyl]-pyrrolidin-3-yl}-acetamide

MS: 528.9 [M+H]$^+$

EXAMPLE 42

1'-(Anthracene-9-carbonyl)-[1,4']bipiperidinyl-3-carboxylic acid (1,3,5-trimethyl-1H-pyrazol-4-yl)-amide

MS: 524.2 [M+H]$^+$

EXAMPLE 43

1'-(Anthracene-9-carbonyl)-[1,4']bipiperidinyl-3-carboxylic acid benzyl-tert-butyl-amide

MS: 562.3 [M+H]$^+$

EXAMPLE 44

4-{[1'-(Anthracene-9-carbonyl)-[1,4']bipiperidinyl-3-carbonyl]-methyl-amino}-benzoic acid methyl ester

MS: 564.2 [M+H]$^+$

EXAMPLE 45

1'-(Anthracene-9-carbonyl)-[1,4']bipiperidinyl-3-carboxylic acid (4-acetylamino-phenyl)-amide

MS: 549.0 [M+H]$^+$

EXAMPLE 46

1'-(Anthracene-9-carbonyl)-[1,4']bipiperidinyl-3-carboxylic acid (2-ethoxy-phenyl)-amide

MS: 536.2 [M+H]$^+$

EXAMPLE 47

1'-(Anthracene-9-carbonyl)-[1,4']bipiperidinyl-3-carboxylic acid ethyl-o-tolyl-amide

MS: 534.3 [M+H]$^+$

EXAMPLE 48

1'-(Anthracene-9-carbonyl)-[1,4']bipiperidinyl-3-carboxylic acid (2,2,6,6-tetramethyl-piperidin-4-yl)-amide

MS: 555.3 [M+H]+

EXAMPLE 49

1'-(Anthracene-9-carbonyl)-[1,4']bipiperidinyl-3-carboxylic acid cyclopropylamide

MS: 456.0 [M+H]+

EXAMPLE 50

1'-(Anthracene-9-carbonyl)-[1,4']bipiperidinyl-3-carboxylic acid benzyl-(2-dimethylamino-ethyl)-amide

MS: 577.3 [M+H]+

EXAMPLE 51

Anthracen-9-yl-[3-(5-nitro-2,3-dihydro-indole-1-carbonyl)-[1,4']bipiperidinyl-1'-yl]-methanone

MS: 563.0 [M+H]+

EXAMPLE 52

1'-(Anthracene-9-carbonyl)-[1,4']bipiperidinyl-3-carboxylic acid (2,4,6-trimethyl-phenyl)-amide

MS: 534.2 [M+H]+

EXAMPLE 53

1'-(Anthracene-9-carbonyl)-[1,4']bipiperidinyl-3-carboxylic acid phenylamide

MS: 492.2 [M+H]+

EXAMPLE 54

1'-(Anthracene-9-carbonyl)-[1,4']bipiperidinyl-3-carboxylic acid isoxazol-3-ylamide

MS: 483.2 [M+H]+

EXAMPLE 55

1'-(Anthracene-9-carbonyl)-[1,4']bipiperidinyl-3-carboxylic acid isopropyl-phenyl-amide

MS: 534.3 [M+H]+

EXAMPLE 56

Anthracen-9-yl-[3-(3,4-dihydro-2H-quinoline-1-carbonyl)-[1,4']bipiperidinyl-1'-yl]-methanone

MS: 532.3 [M+H]+

EXAMPLE 57

Anthracen-9-yl-[3-(3,5-dimethyl-piperazine-1-carbonyl)-[1,4']bipiperidinyl-1'-yl]-methanone

MS: 513.3 [M+H]+

EXAMPLE 58

Anthracen-9-yl-[3-(2,3-dimethyl-2,3-dihydro-indole-1-carbonyl)-[1,4']bipiperidinyl-1'-yl]-methanone

MS: 546.3 [M+H]+

EXAMPLE 59

1'-(Anthracene-9-carbonyl)-[1,4']bipiperidinyl-3-carboxylic acid (1-isopropyl-2-methyl-propyl)-amide

MS: 514.3 [M+H]+

EXAMPLE 60

1'-(Anthracene-9-carbonyl)-[1,4']bipiperidinyl-3-carboxylic acid (3,4-dichloro-benzyl)-ethyl-amide

MS: 602.3 [M+H]+

EXAMPLE 61

1'-(Anthracene-9-carbonyl)-[1,4']bipiperidinyl-3-carboxylic acid methyl-(1-methyl-pyrrolidin-3-yl)-amide

MS: 513.3 [M+H]+

EXAMPLE 62

Anthracen-9-yl-[3-(2,5-dihydro-pyrrole-1-carbonyl)-[1,4']bipiperidinyl-1'-yl]-methanone

MS: 468.3 [M+H]+

EXAMPLE 63

1'-(Anthracene-9-carbonyl)-[1,4']bipiperidinyl-3-carboxylic acid ethyl-phenyl-amide

MS: 520.3 [M+H]+

EXAMPLE 64

1'-(Anthracene-9-carbonyl)-[1,4']bipiperidinyl-3-carboxylic acid (1-ethynyl-cyclohexyl)-amide

MS: 522.3 [M+H]+

EXAMPLE 65

1'-(Anthracene-9-carbonyl)-[1,4']bipiperidinyl-3-carboxylic acid (3-chloro-4-fluoro-phenyl)-amide

MS: 544.2 [M+H]+

EXAMPLE 66

Anthracen-9-yl-[3-(2-pyridin-3-yl-pyrrolidine-1-carbonyl)-[1,4']bipiperidinyl-1'-yl]-methanone

MS: 547.3 [M+H]+

EXAMPLE 67

Anthracen-9-yl-[3-(octahydro-quinoline-1-carbonyl)-[1,4']bipiperidinyl-1'-yl]-methanone

MS: 538.3 [M+H]+

EXAMPLE 68

Anthracen-9-yl-[3-(2-methoxymethyl-pyrrolidine-1-carbonyl)-[1,4']bipiperidinyl-1'-yl]-methanone

MS: 514.3 [M+H]+

EXAMPLE 69

Anthracen-9-yl-[3-(3,4-dihydro-1H-isoquinoline-2-carbonyl)-[1,4']bipiperidinyl-1'-yl]-methanone

MS: 532.3 [M+H]+

EXAMPLE 70

Anthracen-9-yl-[3-(1,3,3-trimethyl-6-aza-bicyclo[3.2.1]octane-6-carbonyl)-[1,4']bipiperidinyl-1'-yl]-methanone

MS: 552.4 [M+H]+

EXAMPLE 71

1'-(Anthracene-9-carbonyl)-[1,4']bipiperidinyl-3-carboxylic acid methyl-(1-methyl-piperidin-4-yl)-amide

MS: 527.3 [M+H]+

EXAMPLE 72

1'-(Anthracene-9-carbonyl)-[1,4']bipiperidinyl-3-carboxylic acid benzo[1,3]dioxol-5-yl-ethyl-amide

MS: 564.3 [M+H]+

EXAMPLE 73

1'-(Anthracene-9-carbonyl)-[1,4']bipiperidinyl-3-carboxylic acid (1-phenyl-ethyl)-amide

MS: 520.3 [M+H]+

EXAMPLE 74

1'-(Anthracene-9-carbonyl)-[1,4']bipiperidinyl-3-carboxylic acid (1,2,3,4-tetrahydro-naphthalen-1-yl)-amide

MS: 546.3 [M+H]+

EXAMPLE 75

1'-(Anthracene-9-carbonyl)-[1,4']bipiperidinyl-3-carboxylic acid (3-imidazol-1-yl-propyl)-amide

MS: 524.3 [M+H]+

EXAMPLE 76

1'-(Anthracene-9-carbonyl)-[1,4']bipiperidinyl-3-carboxylic acid tert-butyl-(2-cyano-ethyl)-amide

MS: 525.3 [M+H]+

EXAMPLE 77

(3R)-1'-(Anthracene-9-carbonyl)-[1,4']bipiperidinyl-3-carboxylic acid benzyl-isopropyl-amide

MS: 548.4 [M+H]+

EXAMPLE 78

(3R)-1'-(Anthracene-9-carbonyl)-[1,4']bipiperidinyl-3-carboxylic acid (3,5-dimethyl-phenyl)-amide

MS: 520.3 [M+H]+

EXAMPLE 79

(3R)-1'-(Anthracene-9-carbonyl)-[1,4']bipiperidinyl-3-carboxylic acid cyclohexyl-isopropyl-amide

MS: 540.4 [M+H]+

EXAMPLE 80

(3R)-1'-(Anthracene-9-carbonyl)-[1,4']bipiperidinyl-3-carboxylic acid (1,1-dimethyl-propyl)-amide

MS: 486.3 [M+H]+

EXAMPLE 81

(3R)-1'-(Anthracene-9-carbonyl)-[1,4']bipiperidinyl-3-carboxylic acid cyclohexyl-ethyl-amide

MS: 526.4 [M+H]+

EXAMPLE 82

(3R)-Anthracen-9-yl-[3-(6-fluoro-2-methyl-3,4-dihydro-2H-quinoline-1-carbonyl)-[1,4']bipiperidinyl-1'-yl]-methanone

MS: 564.3 [M+H]+

EXAMPLE 83

(3R)-Anthracen-9-yl-[3-(2-ethyl-piperazine-1-carbonyl)-[1,4']bipiperidinyl-1'-yl]-methanone

MS: 513.4 [M+H]+

EXAMPLE 84

(3R)-1'-(Anthracene-9-carbonyl)-[1,4']bipiperidinyl-3-carboxylic acid allyl-cyclohexyl-amide

MS: 538.4 [M+H]+

EXAMPLE 85

(3R)-1'-(Anthracene-9-carbonyl)-[1,4']bipiperidinyl-3-carboxylic acid (4-diethylamino-1-methyl-butyl)-amide

MS: 557.4 [M+H]+

EXAMPLE 86

(3R)-1'-(Anthracene-9-carbonyl)-[1,4']bipiperidinyl-3-carboxylic acid (4-methyl-thiazol-2-yl)-amide

MS: 513.3 [M+H]+

EXAMPLE 87

(3R)-1'-(Anthracene-9-carbonyl)-[1,4']bipiperidinyl-3-carboxylic acid but-3-ynyl-phenyl-amide

MS: 545.3 [M+H]+

EXAMPLE 88

(3R)-1'-(Anthracene-9-carbonyl)-[1,4']bipiperidinyl-3-carboxylic acid phenyl-pyridin-2-yl-amide

MS: 569.3 [M+H]+

EXAMPLE 89

(3R)-Anthracen-9-yl-[3-(2,6-dimethyl-piperazine-1-carbonyl)-[1,4']bipiperidinyl-1'-yl]-methanone

MS: 513.4 [M+H]+

EXAMPLE 90

(3R)-1'-(Anthracene-9-carbonyl)-[1,4']bipiperidinyl-3-carboxylic acid dibenzylamide

MS: 596.4 [M+H]+

EXAMPLE 91

(3R)-1'-(Anthracene-9-carbonyl)-[1,4']bipiperidinyl-3-carboxylic acid diallylamide

MS: 496.4 [M+H]+

EXAMPLE 92

(3R)-Anthracen-9-yl-[3-(2-ethyl-piperidine-1-carbonyl)-[1,4']bipiperidinyl-1'-yl]-methanone

MS: 512.4 [M+H]$^+$

EXAMPLE 93

(3R)-Anthracen-9-yl-[3-(2,3-dihydro-indole-1-carbonyl)-[1,4']bipiperidinyl-1'-yl]-methanone

MS: 518.3 [M+H]$^+$

EXAMPLE 94

(3R)-Anthracen-9-yl-[3-(2-methyl-piperidine-1-carbonyl)-[1,4']bipiperidinyl-1'-yl]-methanone

MS: 498.4 [M+H]$^+$

EXAMPLE 95

(3R)-Anthracen-9-yl-[3-(3-methyl-piperidine-1-carbonyl)-[1,4']bipiperidinyl-1'-yl]-methanone

MS: 498.4 [M+H]$^+$

EXAMPLE 96

(3R)-Anthracen-9-yl-[3-(4-methyl-piperidine-1-carbonyl)-[1,4']bipiperidinyl-1'-yl]-methanone

MS: 498.4 [M+H]$^+$

EXAMPLE 97

(3R)-1'-(Anthracene-9-carbonyl)-[1,4']bipiperidinyl-3-carboxylic acid (3-nitro-phenyl)-amide

MS: 537.2 [M+H]$^+$

EXAMPLE 98

(3R)-1'-(Anthracene-9-carbonyl)-[1,4']bipiperidinyl-3-carboxylic acid (1,1,3,3-tetramethyl-butyl)-amide

MS: 528.4 [M+H]$^+$

EXAMPLE 99

(3R)-1-(Anthracene-9-carbonyl)-[1,4']bipiperidinyl-3-carboxylic acid bis-cyanomethyl-amide

MS: 494.2 [M+H]$^+$

EXAMPLE 100

(3R)-1'-(Anthracene-9-carbonyl)-[1,4']bipiperidinyl-3-carboxylic acid cyclobutylamide

MS: 470.3 [M+H]$^+$

EXAMPLE 101

(3R)-Anthracen-9-yl-{3-[2-(2-hydroxy-ethyl)-piperidine-1-carbonyl]-[1,4']bipiperidinyl-1'-yl}-methanone

MS: 528.4 [M+H]$^+$

EXAMPLE 102

(3R)-1'-(Anthracene-9-carbonyl)-[1,4']bipiperidinyl-3-carboxylic acid ethyl-phenyl-amide

MS: 520.3 [M+H]$^+$

EXAMPLE 103

(3R)-1'-(Anthracene-9-carbonyl)-[1,4']bipiperidinyl-3-carboxylic acid (1-phenyl-ethyl)-amide

MS: 520.3 [M+H]$^+$

EXAMPLE 104

(3R)-Anthracen-9-yl-[3-(3,4-dihydro-2H-quinoline-1-carbonyl)-[1,4']bipiperidinyl-1'-yl]-methanone

MS: 532.3 [M+H]$^+$

EXAMPLE 105

(3R)-4-[1'-(Anthracene-9-carbonyl)-[1,4']bipiperidinyl-3-carbonyl]-piperazine-1-carboxylic acid ethyl ester R$_F$ 0.33 (9:1 dichloromethane-methanol)
MS: 557.5 [M+H]$^+$

EXAMPLE 106

(3R)-4-[1'-(Anthracene-9-carbonyl)-[1,4']bipiperidinyl-3-carbonyl]-piperazine-1-carbaldehyde R$_F$ 0.29 (9:1 dichloromethane-methanol) MS: 513.4 [M+H]$^+$

EXAMPLE 107

(3R)-Anthracen-9-yl-{3-[4-(furan-2-carbonyl)-piperazine-1-carbonyl]-[1,4']bipiperidinyl-1'-yl}-methanone R$_F$ 0.33 (9:1 dichloromethane-methanol) MS: 579.4 [M+H]$^+$

EXAMPLE 108

(3R)-4-[1'-(Anthracene-9-carbonyl)-[1,4']bipiperidinyl-3-carbonyl]-piperazine-1-carboxylic acid tert-butyl ester R$_F$ 0.22 (9:1 dichloromethane-methanol) MS: 585.5 [M+H]$^+$

EXAMPLE 109

(3R)-Anthracen-9-yl-[3-(meso-3,5-dimethyl-morpholine-4-carbonyl)-[1,4']bipiperidinyl-1'-yl]-methanone The title compound was prepared from meso-3,5-dimethylmorpholine (D. Enders et al. *Synthesis*, 1994, 66).

MS: 514.4 [M+H]$^+$ $^1$H-NMR (CDCl$_3$) δ 8.44 (s, 1H), 8.00–7.74 (m, 4H), 7.55–7.41 (m, 4H), 5.21 (dm, 1H, J=13.3 Hz), 4.38 (m, 1H), 4.07–3.98 (m, 1H), 3.97–3.79 (m, 1H), 3.79–3.66 (m, 2H), 3.65–3.54 (m, 1H), 3.54–3.43 (m, 2H), 3.26–3.20 (dm, 1H, J=13.3 Hz), 3.04–2.77 (m, 4H), 2.77–2.57 (m, 1H), 2.57–2.38 (m, 2H), 2.31 (tm, 1H, J=10.4 Hz), 2.13 (tm, 2H, J=9.1 Hz), 1.81–1.64 (m, 3H), 1.63–1.46 (m, 2H), 1.46–1.41 (m, 2H), 1.41–1.20 (m, 6H).

EXAMPLE 110

(3R)-Anthracen-9-yl-[3-(3R,5R-dimethyl-morpholine-4-carbonyl)-[1,4']bipiperidinyl-1'-yl]-methanone The title compound was prepared from (R,R)-3,5-dimethylmorpholine which was prepared by a procedure analogous to that described by D. Enders et al. *Synthesis*, 1994, 66.

MS: 514.4 [M+H]+ 1H-NMR (CDCl3) δ 8.42 (s, 1H), 8.02–7.74 (m, 4H), 7.53–7.39 (m, 4H), 5.19 (brd, 1H, J=15.0 Hz), 4.05–3.96 (m, 2H), 3.96–3.85 (m, 2H), 3.64 –3.52 (m, 2H), 3.20 (dm, 1H, J=13.7 Hz), 3.03–2.80 (m, 4H), 2.71–2.58 (m, 1H), 2.54–2.37 (m, 2H), 2.18–2.03 (m, 3H), 1.80–1.66 (m, 3H), 1.36–1.27 (m, 3H).

EXAMPLE 111

(3R)-Anthracen-9-yl-[3-(3,3-dimethyl-morpholine-4-Carbonyl)-[1,4']bipiperidinyl-1'-yl]-methanone The title compound was prepared from 3,3-dimethylmorpholine which was prepared from 2-methyl-2-amino-propanol and glycolaldehyde dimer by a procedure analogous to that described by D. Enders et al. *Synthesis*, 1994, 66.

MS: 514.4 [M+H]+ 1H-NMR (CDCl3) δ 8.47 (s, 1H), 8.05–7.77 (m, 4H), 7.57–7.43 (m, 4H), 5.27 (brd, 1H, J=12.9 Hz), 3.81–3.69 (m, 2H), 3.53–3.36 (m, 2H), 3.37–3.30 (m, 2H), 3.23 (dm, 1H, J=13.7 Hz), 3.06–2.83 (m, 5H), 2.57–2.51 (m, 2H), 2.31–2.10 (m, 2H), 1.90–1.71 (m, 6H), 1.40–1.36 (m, 6H), 1.32–1.30 (m, 1H).

EXAMPLE 112

(3R)-Anthracen-9-yl-[3-(3S,5S-dimethyl-morpholine-4-Carbonyl)-[1,4']bipiperidinyl-1'-yl]-methanone The title compound was prepared from (S,S)-3,5-dimethylmorpholine (D. Enders et al. *Synthesis*, 1994, 66).

MS: 514.5 [M+H]+ 1H-NMR (CDCl3) δ 8.46 (s, 1H), 8.05–7.77 (m, 4H), 7.54–7.42 (m, 4H), 5.23 (brd, 2H, J=13.3 Hz), 4.11–4.02 (m, 2H), 3.98 (m, 1 H), 3.69–3.56 (m, 2H), 3.16 (d, 1H, J=13.7 Hz), 3.04–2.78 (m, 4H), 2.72 (m, 1H), 2.50 (m, 1H), 2.39–2.22 (m, 1H), 2.22–2.05 (m, 2H), 1.85–1.70 (m, 3H), 1.69–1.43 (m, 3H), 1.39–1.32 (m, 6H), 1.31–1.18 (m, 1H).

EXAMPLE 113

(3R)-4-[1'-(Anthracene-9-Carbonyl)-[1,4']bipiperidinyl-3-carbonyl]-3-methyl-piperazin-2-one

MS: 513.5 [M+H]+

EXAMPLE 114

(3R)-Anthracen-9-yl-[3-(2,3,5,6-tetramethyl-piperazine-1-carbonyl)-[1,4']bipiperidinyl-1'-yl]-methanone

MS: 541.5 [M+H]+

The following Examples were prepared from (3R)-1'-[2,6-bis-(4-chloro-phenyl)-pyridine-4-carbonyl]-[1,4']bipiperidinyl-3-carboxylic acid ethyl ester and commercially obtained amines using procedures analogous to those described above:

EXAMPLE 115

(3R)-1'-[2,6-Bis-(4-chloro-phenyl)-pyridine-4-Carbonyl]-[1,4']bipiperidinyl-3-carboxylic acid tert-butoxy-amide $R_F$ 0.77 (4:1 dichloromethane-methanol) MS: 609.0 [M+H]+

EXAMPLE 116

(3R)-[3-(Azetidine-1-carbonyl)-[1,4']bipiperidinyl-1'-yl]-[2,6-bis-(4-chloro-phenyl)-pyridin-4-yl]-methanone $R_F$ 0.69 (4:1 dichloromethane-methanol) MS: 577.0 [M+H]+

EXAMPLE 117

(3R)-1'-[2,6-Bis-(4-chloro-phenyl)-pyridine-4-carbonyl]-[1,4']bipiperidinyl-3-carboxylic acid methyl-(1-methyl-piperidin-4-yl)-amide $R_F$ 0.09 (4:1 dichloromethane-methanol) MS: 650.0 [M+H]+

EXAMPLE 118

(3R)-[2,6-Bis-(4-chloro-phenyl)-pyridin-4-yl]-[3-(4-hydroxy-piperidine-1-carbonyl)-[1,4']bipiperidinyl-1'-yl]-methanone $R_F$ 0.42 (4:1 dichloromethane-methanol) MS: 621.0 [M+H]+

EXAMPLE 119

(3R)-[2,6-Bis-(4-chloro-phenyl)-pyridin-4-yl]-[3-(3,5-dimethyl-piperazine-1-carbonyl)-[1,4']bipiperidinyl-1'-yl]-methanone $R_F$ 0.22 (4:1 dichloromethane-methanol) MS: 634.2 [M+H]+

EXAMPLE 120

(3R)-[2,6-Bis-(4-chloro-phenyl)-pyridin-4-yl]-[3-(4-methyl-piperazine-1-carbonyl)-[1,4']bipiperidinyl-1'-yl]-methanone $R_F$ 0.22 (4:1 dichloromethane-methanol) MS: 620.1 [M+H]+

EXAMPLE 121

(3R)-{1'-[2,6-Bis-(4-chloro-phenyl)-pyridine-4-carbonyl]-[1,4']bipiperidinyl-3-yl}-(1,4-dioxa-8-aza-spiro[4.5]dec-8-yl)-methanone $R_F$ 0.38 (9:1 dichloromethane-methanol) MS: 663.2 [M+H]+

EXAMPLE 122

(3R)-[2,6-Bis-(4-chloro-phenyl)-pyridin-4-yl]-[3-(4-pyrrolidin-1-yl-piperidine-1-carbonyl)-[1,4']bipiperidinyl-1'-yl]-methanone $R_F$ 0.10 (4:1 dichloromethane-methanol) MS: 674.1 [M+H]+

The following Examples were prepared from (3R)-1'-[2,6-diphenyl-pyridine-4-carbonyl]-[1,4']bipiperidinyl-3-carboxylic acid ethyl ester and commercially obtained amines using procedures analogous to those described above:

EXAMPLE 123

(3R)-[1'-(2,6-Diphenyl-pyridine-4-carbonyl)-[1,4']bipiperidinyl-3-yl]-(2-oxa-5-aza-bicyclo[2.2.1]hept-5-yl)-methanone

MS: 551.5 [M+H]+

EXAMPLE 124

(3R)-1'-(2,6-Diphenyl-pyridine-4-carbonyl)-[1,4']bipiperidinyl-3-carboxylic acid bis-(2,2,2-trifluoro-ethyl)-amide

MS: 633.3 [M+H]+

EXAMPLE 125

(3R)-5-[1'-(2,6-Diphenyl-pyridine-4-carbonyl)-[1,4']
bipiperidinyl-3-carbonyl]-2,5-diaza-bicyclo[2.2.1]
heptane-2-carboxylic acid tert-butyl ester

MS: 650.5 [M+H]$^+$

EXAMPLE 126

(3R)-1'-(2,6-Diphenyl-pyridine-4-carbonyl)-[1,4']
bipiperidinyl-3-carboxylic acid methoxy-methyl-
amide

MS: 513.4 [M+H]$^+$

Intermediate 23

[1,4']bipiperidinyl-3-carboxylic acid diethylamide

3-Diethylcarbamoyl-[1,4']bipiperidinyl-1'-carboxylic acid tert-butyl ester was prepared from tert-butyl 4-oxo-1-piperidinecarboxylate and N,N-diethylnipecotamide by a procedure analogous to that described for Intermediate 1 (48% yield). This compound (3.5 g, 9.52 mmol) was deprotected by treatment with hydrogen chloride in ethyl acetate (90 mL) as described for Intermediate 2. The hydrochloride salt was dissolved in water (20 mL) and the pH adjusted to 13–14 by addition of 6M sodium hydroxide solution. This mixture was extracted with dichloromethane (×3), the organic extract was dried with anhydrous sodium sulfate and evaporated to dryness under vacuum to give the title compound (1.9 g, 76%).

$^1$H NMR δ (CDCl$_3$): 3.33 (q, 2H, J=7 Hz); 3.31 (q, 2H, J=7 Hz); 3.17 (dm, 2H, J=12.5 Hz); 2.89 (m, 2H); 2.71 (m, 1H); 2.60 (tm, 2H, J=12.4 Hz); 2.42 (t, 2H, J=11 Hz); 2.19 (m, 1H); 1.83 (m, 2H); 1.75 (m, 2H); 1.65–1.41 (m, 4H); 1.16 (t, 3H, J=7.1 Hz); 1.07 (t, 3H, J=7.05 Hz) MS: 268.4 [M+H]$^+$

The following Examples were prepared from [1,4']bipiperidinyl-3-carboxylic acid diethylamide by a procedure analogous to that described in Example 1 using commercially available (unless otherwise noted) acid chlorides or carboxylic acids which were converted to their acid chlorides using a procedure analogous to that described for Intermediate 3.

EXAMPLE 127

1'-(Acridine-9-carbonyl)-[1,4']bipiperidinyl-3-
carboxylic acid diethylamide

R$_F$ 0.32 (9:1 dichloromethane-methanol) MS: 473.3 [M+H]$^+$

EXAMPLE 128

1'-(Phenanthrene-9-carbonyl)-[1,4']bipiperidinyl-3-
carboxylic acid diethylamide R$_F$ 0.25 (9:1 dichloromethane-methanol) MS: 472.4 [M+H]$^+$

EXAMPLE 129

1'-(1,2,3,4-Tetrahydro-acridine-9-carbonyl)-[1,4']
bipiperidinyl-3-carboxylic acid diethylamide R$_F$ 0.40 (4:1 dichloromethane-methanol) MS: 477.4 [M+H]$^+$

EXAMPLE 130

1'-(2-Ethoxy-naphthalene-1-carbonyl)-[1,4']
bipiperidinyl-3-carboxylic acid diethylamide R$_F$ 0.34 (9:1 dichloromethane-methanol) MS: 466.3 [M+H]$^+$

EXAMPLE 131

1'-[6-chloro-2-(4-chloro-phenyl)-quinoline-4-
carbonyl]-[1,4']bipiperidinyl-3-carboxylic acid
diethylamide

EXAMPLE 132

(3R)-1'-[7-Chloro-2-(4-chloro-phenyl)-6-methyl-
quinoline-4-carbonyl]-[1,4']bipiperidinyl-3-
carboxylic acid diethylamide

MS: 581.0 [M+H]$^+$

EXAMPLE 133

(3R)-1'-(2-Pyridin-4-yl-6-trifluoromethyl-quinoline-
4-carbonyl)-[1,4']bipiperidinyl-3-carboxylic acid
diethylamide

MS: 568.1 [M+H]$^+$

EXAMPLE 134

1'-(2,6-Diphenyl-pyridine-4-carbonyl)-[1,4']
bipiperidinyl-3-carboxylic acid diethylamide The title compound was prepared from 2,6-diphenylisonicotinic acid which was obtained according to a procedure analogous to that described by P. Blumbergs et al. *J. Med. Chem.* 1972, 15, 808.

MS: 525.3 [M+H]$^+$ $^1$H-NMR (CDCl$_3$) δ 8.20–8.13 (m, 4H), 7.79–7.75 (m, 2H), 7.53–7.40 (m, 6H), 4.74 (dm, 1H, J=13.1 Hz), 3.74 (brd, 1H, J=13.3Hz), 3.45–3.24 (m, 5H), 3.14 (brt, 1H, J=12.1 Hz), 2.98–2.70 (m, 4H), 2.62 (brt, 1H, J=11.2 Hz), 2.40–2.28 (m, 1H), 2.24–2.11 (m, 1H), 2.02–1.92 (m, 1H), 1.85–1.68 (m, 3H), 1.66–1.37 (m, 4H), 1.18 (t, 3H, J=7.1 Hz), 1.07 (t, 3H, J=7.1 Hz).

EXAMPLE 135

(3R)-1'-(Anthracene-9-sulfonyl)-[1,4']bipiperidinyl-
3-carboxylic acid diethylamide Anthracene-9-sulfonyl chloride was prepared according to the procedure described by B. E. Bauer in U.S. Pat. No. 5,030,631. (3R)-[1,4']Bipiperidinyl-3-carboxylic acid diethylamide (0.76 mmol) was reacted with this sulfonyl chloride under conditions analogous to those described above for the preparation of Example 1 to give the title compound (216.3 mg, 56%).

R$_F$ 0.46 (9:1 dichloromethane-methanol) MS: 508.2 [M+H]$^+$ $^1$H-NMR (CDCl$_3$) δ 8.44 (s, 1H), 8.09–7.90 (m, 3H), 7.85–7.75 (m, 1H), 7.60–7.40 (m, 4H), 5.17 (brd, 1H, J=13.2 Hz), 4.17–4.04 (m, 2H), 3.20 (dm, 1H, J=13.5 Hz), 3.06–2.92 (m, 2H), 2.87 (tm, 1H, J=13.0 Hz), 2.80–2.67 (m, 1H), 2.56–2.43 (m, 2H), 2.39–2.28 (m, 1H), 2.21–2.11 (m, 1H), 2.11–2.03 (m, 1H), 1.96–1.83 (m, 2H), 1.78–1.65 (m, 2H), 1.58–1.36 (m, 3H), 1.27–1.15 (m, 3H).

The following Examples were prepared from [1,4']bipiperidinyl-3-yl-morpholin-4-yl-methanone using an analogous procedure to that described above for the preparation of Example 1.

EXAMPLE 136

(3R)-[7-Chloro-2-(4-chloro-phenyl)-6-methyl-
quinolin-4-yl]-[3-(morpholine-4-carbonyl)-[1,4']
bipiperidinyl-1'-yl]-methanone R$_F$ 0.36 (19:1 dichloromethane-methanol) MS: 595.1 [M+H]$^+$

EXAMPLE 137

(3R)-[2-(4-Chloro-phenyl)-6-methyl-quinolin-4-yl]-[3-(morpholine-4-carbonyl)-[1,4']bipiperidinyl-1'-yl]-methanone

MS: 562.3 [M+H]$^+$

EXAMPLE 138

(3R)-[4,6-Bis-(4-chloro-phenyl)-[1,3,5]triazin-2-yl]-[3-(morpholine-4-carbonyl)-[1,4']bipiperidinyl-1'-yl]-methanone The title compound was prepared from 4,6-bis-(4-chloro-phenyl)-[1,3,5]triazine-2-carboxylic acid which was obtained by a procedure analogous to that described by J. S. Gillespie et al. *J. Heterocyclic Chem.*, 1971, 8, 723.

R$_F$ 0.24 (19:1 dichloromethane-methanol) MS: 609.0 [M+H]$^+$ $^1$H-NMR (CDCl$_3$) δ 8.57–8.50 (m, 4H), 7.51–7.41 (m, 4H), 4.80 (bd, 1H, J=13.0 Hz), 3.71–3.51 (m, 7H), 3.51–3.42 (m, 2H), 3.08 (tm, 1H, J=12.2 Hz), 2.93–2.76 (m, 3H), 2.73–2.63 (m, 1H), 2.63–2.52 (m, 1H), 2.50–2.37 (m, 1H), 2.25–2.12 (m, 1H), 2.00–1.91 (m, 1H), 1.84–1.72 (m, 3H), 1.72–1.38 (m, 4H) ppm. $^{13}$C-NMR (CDCl$_3$) δ 172.76, 171.28, 170.22, 163.58, 139.74, 133.35, 130.54, 129.11, 66.93, 66.82, 62.34, 52.47, 52.20, 49.46, 49.14, 46.49, 45.93, 41.90, 41.38, 39.66, 39.62, 28.44, 28.15, 28.04, 27.92, 27.64, 25.39.

EXAMPLE 139

(3R)-[2-(3,5-Bis-trifluoromethyl-phenyl)-6-fluoro-quinolin-4-yl]-[3-(morpholine-4-carbonyl)-[1,4']bipiperidinyl-1'-yl]-methanone

MS: 667.1 [M+H]$^+$

EXAMPLE 140

(3R)-[2-(2,6-Difluoro-phenyl)-6-fluoro-quinolin-4-yl]-[3-(morpholine-4-carbonyl)-[1,4']bipiperidinyl-1'-yl]-methanone

MS: 567.1 [M+H]$^+$

EXAMPLE 141

(3R)-[3-(Morpholine-4-carbonyl)-[1,4']bipiperidinyl-1'-yl]-(3-phenyl-naphthalen-1-yl)-methanone The title compound was prepared from 3-phenyl-naphthalene-1-carboxylic acid which was obtained according to a procedure described by G. Giardina et al. *J. Med Chem.*, 1997, 40,1794.

MS: 512.5 [M+H]$^+$

EXAMPLE 142

(3R)-(3-Methyl-2-phenyl-quinolin-4-yl)-[3-(morpholine-4-carbonyl)-[1,4']bipiperidinyl-1'-yl]-methanone The title compound was prepared from 3-methyl-2-phenyl-quinoline-4-carboxylic acid which was obtained according to a procedure described by K. Lackey and D. D. Sternbach *Synthesis*, 1993, 993.

MS: 527.3 [M+H]$^+$

EXAMPLE 143

(3R)-(5,7-Dimethyl-2-phenyl-quinolin-4-yl)-[3-(morpholine-4-carbonyl)-[1,4']bipiperidinyl-1'-yl]-methanone

MS: 541.3 [M+H]$^+$

EXAMPLE 144

1'-(Anthracene-9-carbonyl)-[1,4']bipiperidinyl-3-carboxylic acid benzyl ester

[1,4']Bipiperidinyl-3-carboxylic acid benzyl ester hydrochloride and anthracene-9-carbonyl chloride were reacted using a procedure analogous to that described above for Example 1 to give the title compound.

R$_F$ 0.42 (19:1 dichloromethane-methanol) MS: 507.5 [M+H]$^+$ $^1$H-NMR (CDCl$_3$) δ 8.45 (s, 1H), 8.04–7.78 (m, 4H), 7.52–7.41 (m, 4H), 7.35–7.25 (m, 5H), 5.18 (brd, 1H, J=13.1 Hz), 5.12–5.07 (m, 2H), 3.18 (dm, 1H, J=13.1 Hz), 3.06–2.92 (m, 2H), 2.86 (tm, 1H, J=13 Hz), 2.78–2.66 (m, 1H), 2.62–2.53 (m, 1H), 2.54–2.44 (m, 1H), 2.44–2.35 (m, 1H), 2.26–2.13 (m, 1H), 2.10–2.00 (m, 1H), 1.98–1.86 (m, 1 H), 1.80–1.63 (m, 2H), 1.58–1.39 (m, 3H), 1.35–1.21 (m, 1H).

EXAMPLES 145 AND 146

1'-(Anthracene-9-carbonyl)-[1,4']bipiperidinyl-3-carboxylic acid isopropyl ester and 1'-(anthracene-9-carbonyl)-[1,4']bipiperidinyl-3-carboxylic acid The mixture of [1,4']bipiperidinyl-3-carboxylic acid benzyl and isopropyl esters obtained as described (1 64.3 mg) was dissolved in methanol (20 mL) and 10% palladium on carbon was added. The suspension was stirred under hydrogen at atmospheric pressure for 48 hr. The catalyst was removed by filtration, the solvent was evaporated under vacuum and the mixture purified by chromatography on silica eluting with a gradient of 2.5% to 40% methanol in dichloromethane to give 1'-(anthracene-9-carbonyl)-[1,4']bipiperidinyl-3-carboxylic acid isopropyl ester (Example 145, 18.1 mg) eluting first followed by 1'-(anthracene-9-carbonyl)-[1,4']bipiperidinyl-3-carboxylic acid (Example 146, 87.3 mg).

R$_F$ 0.55 (9:1 dichloromethane-methanol) MS: 459.5 [M+H]$^+$ (Example 145) R$_F$ 0.50 (7:3 dichloromethane-methanol) MS: 417.3 [M+H]$^+$ (Example 146)

EXAMPLE 147

Anthracen-9-yl-[3-(morpholine-4-sulfonyl)-[1,4']bipiperidinyl-1'-yl]-methanone

Pyridine-3-sulfonyl chloride was prepared from phosphorus pentachloride (17.82 g, 0.112 mol) and pyridine-3-sulfonic acid (12.36 g, 77.7 mmol) according to the procedure described by P. Breant et al. *Synthesis*, 1983, 822. Anhydrous toluene (20 mL) was added to the product and this solution added slowly to a mixture of toluene (100 mL), triethylamine (4 eq, 43 mL) and morpholine (1.5 eq, 10.3 mL) with cooling in ice water. A thick precipitate was formed. The mixture was stirred for 16 hr and then shaken with a saturated K$_2$CO$_3$ solution, dried over anhydrous sodium sulfate and evaporated to give a yellowish brown solid. Trituration with methanol gave 4-(pyridine-3-sulfonyl)-morpholine as a pale yellow solid (14.29 g, 81%).

4-(Pyridine-3-sulfonyl)-morpholine (25 mmol, 5.7 g) was shaken with platinum (IV) oxide (500 mg) in ethanol (50 mL) at 60° C. under hydrogen at 50 psi for 16 h. Reduction was incomplete so the catalyst was removed by filtration, the solvent evaporated under vacuum and the residue dissolved in a mixture of water (50 mL) and acetic acid (10 mL) with warming. Platinum (IV) oxide (1 g) was added and hydrogenation at 50 psi was continued for a further 70 h at 60° C. The catalyst was removed by filtration and the solvent was evaporated under vacuum to give an orange gum which was redissolved in water and the solution (pH 4–5) was extracted with dichloromethane (×3). The aqueous layer was evaporated to a small volume under vacuum, made strongly basic by the addition of 4 M sodium hydroxide solution, xylenes were added and the solvents were removed under vacuum. The residue was agitated with dichloromethane and anhydrous sodium sulfate, the solids removed by flitration through Celite® and the filtrate evaporated under vacuum to give 4-(piperidine-3-sulfonyl)-morpholine as a waxy orange solid (1.3 g, 22%).

A mixture of the 4-(piperidine-3-sulfonyl)-morpholine (710 mg, 3.03 mmol), tert-butyl 4-oxo-1-piperidinecarboxylate (1 eq, 605 mg) and Ti(O$^i$Pr)$_4$ (1.25 eq, 1.12 mL) was stirred under nitrogen at ambient temperature for 1 hr. A solution of sodium cyanoborohydride (0.7 eq, 133 mg) in anhydrous ethanol (3 mL) was added and the clear solution was stirred overnight. Water (0.6 mL) was added followed by sufficient ethanol to permit stirring. The thick suspension was filtered through Celite® rising through with ethanol and the filtrate was evaporated to a cloudy oil which was redissolved in dichloromethane/ethanol, a few drops of water added and the mixture was filtered through Celite®. The filtrate was diluted with toluene, evaporated under vacuum and the residue purified by chromatography on silica gel eluting with 2.5% methanol-dichloromethane. The desired fractions were combined, evaporated under vacuum and the residue chromatographed on silica gel eluting with 2.5% methanol-dichloromethane to give 3-(morpholine-4-sulfonyl)-[1,4']bipiperidinyl-1'-carboxylic acid tert-butyl ester (520 mg, 41%).

R$_F$ 0.18 (19:1 dichloromethane-methanol) MS: 418.4.4 [M+H]$^+$ 3-(Morpholine-4-sulfonyl)-[1,4']bipiperidinyl-1'-carboxylic acid tert-butyl ester was converted by deprotection and acylation reactions analogous to those described above for the preparation of Example 1 to give the title compound (240 mg, 72%).

R$_F$ 0.30 (19:1 dichloromethane-methanol) MS: 522.4 [M+H]$^+$ $^1$H-NMR (CDCl$_3$) δ 8.46 (s, 1H), 8.04–8.00 (m, 2H), 8.00–7.95 (m, 1H), 7.85–7.75 (m, 1H), 7.6–7.4 (m, 4H), 5.21 (brd, 1H, J=12.9 Hz), 3.7–3.6 (m, 4H), 3.3–328 (m, 4H), 3.25–3.18 (m, 2H), 3.17–3.12 (m, 1H), 2.99 (brt, 1H, J=12.5 Hz), 2.9–2.8 (m, 2H), 2.6–2.5 (m, 1H), 2.4–2.3 (m, 1H), 2.2–2.0 (m, 2H), 1.88–1.8 (m, 1H), 1.7–1.6 (m, 1H), 1.5–1.4 (m, 2H).

EXAMPLE 148

1'-[6-chloro-2-(4-chloro-phenyl)-quinoline-4-carbonyl]-[1,4']bipiperidinyl-3-carboxylic acid diethylamide To a solution of [1,4']bipiperidinyl-3-carboxylic acid diethylamide (0.38 mmol, 115 mg) and 6-chloro-2-(4-chloro-phenyl)-quinoline-4-carboxylic acid (0.417 mmol, 133 mg) in anhydrous dichloromethane was added 1-hydroxybenzotriazole hydrate (0.42 mmol, 56 mg) followed by triethylamine (1.52 mmol, 0.8 mL) then 1-ethyl-3-(3'-dimethylaminopropyl)carbodiimide hydrochloride (0.46 mmol, 87 mg). The solution was stirred at ambient temperature for 16 hr then 2M sodium hydroxide (25 mL) was added. The aqueous layer was separated and extracted with ethyl acetate (3×25 mL). The combined organic layers were washed with brine, dried over anhydrous sodium sulfate and evaporated to dryness under vacuum. The residue was chromatographed on a silica gel rotor eluting with a 1 to 5% methanol in dichloromethane gradient to give the title compound (63 mg, 29%).

MS: 567.2 [M+H]$^+$

The following Examples were prepared by an analogous procedure using commercially available (unless otherwise noted) carboxylic acids:

EXAMPLE 149

1'-(2-Phenyl-quinoline-4-carbonyl)-[1,4']bipiperidinyl-3-carboxylic acid diethylamide

MS: 499.3 [M+H]$^+$

EXAMPLE 150

1'-(6,8-Dichloro-2-phenyl-quinoline-4-carbonyl)-[1,4']bipiperidinyl-3-carboxylic acid diethylamide

MS: 567.1 [M+H]$^+$

EXAMPLE 151

1'-(Anthracene-1-carbonyl)-[1,4']bipiperidinyl-3-carboxylic acid diethylamide

MS: 472.3 [M+H]$^+$

EXAMPLE 152

1'-(6-Bromo-2-pyridin-3-yl-quinoline-4-carbonyl)-[1,4']bipiperidinyl-3-carboxylic acid diethylamide

MS: 580.1 [M+H]$^+$

EXAMPLE 153

1'-(Benzo[f]quinoline-5-carbonyl)-[1,4']bipiperidinyl-3-carboxylic acid diethylamide

MS: 473.3 [M+H]$^+$

EXAMPLE 154

1'-[6-Trifluoromethyl-2-(4-trifluoromethyl-phenyl)-quinoline-4-carbonyl]-[1,4']bipiperidinyl-3-carboxylic acid diethylamide

MS: 635.2 [M+H]$^+$

EXAMPLE 155

(3R)-1'-(2-Pyridin-4-yl-7-trifluoromethyl-quinoline-4-carbonyl)-[1,4']bipiperidinyl-3-carboxylic acid diethylamide

MS: 568.0 [M+H]$^+$

EXAMPLE 156

(3R)-1'-(3,3''-Dimethyl-[1,1';3',1'']terphenyl-2'-carbonyl)-[1,4']bipiperidinyl-3-carboxylic acid diethylamide

MS: 552.2 [M+H]$^+$

The following Examples were prepared from [1,4']bipiperidinyl-3-yl-morpholin-4-yl-methanone by a procedure analogous to that used for Example 148 using commercially available carboxylic acids (unless otherwise noted) and 1-ethyl-3-(3'-dimethylaminopropyl) carbodiimide hydrochloride (EDCI) as the coupling reagent:

EXAMPLE 157

(3R)-[3-(Morpholine-4-carbonyl)-[1,4']bipiperidinyl-1-yl]-[1,1';3',1'']terphenyl-5'-yl-methanone

MS: 539.2 [M+H]$^+$

EXAMPLE 158

(3R)-[3-(Morpholine-4-carbonyl)-[1,4']bipiperidinyl-1'-yl]-(3-phenyl-isoquinolin-1-yl)-methanone The title compound was prepared from 3-phenyl-isoquinoline-1-carboxylic acid which was obtained according to a procedure described by G. Giardina et al. *J. Med Chem.*, 1997, 40, 1794.

MS: 513.1 [M+H]$^+$

EXAMPLE 159

(3R)-(5-Chloro-1,3-diphenyl-1H-pyrazol-4-yl)-[3-(morpholine-4-carbonyl)-[1,4']bipiperidinyl-1'-yl]-methanone

MS: 562.1 [M+H]$^+$

EXAMPLE 160

(3R)-[3-(Morpholine-4-carbonyl)-[1,4']bipiperidinyl-1'-yl]-[6-trifluoromethyl-2-(4-trifluoromethyl-phenyl)-quinolin-4-yl]-methanone To a solution of (3R)-[1,4']bipiperidinyl-3-yl-morpholin-4-yl-methanone (0.314 mmol, 100 mg) and 6-trifluoromethyl-2-(4-trifluoromethyl-phenyl)-quinoline-4-carboxylic acid (0.346 mmol, 133 mg) in anhydrous dichloromethane was added 1-hydroxybenzotriazole hydrate (0.157 mmol, 21 mg) followed by diisopropylethylamine (0.942 mmol, 0.163 mL) then benzotriazo-1-yloxytris(dimethylamino)phosphonium hexafluorophosphate (BOP, 0.942 mmol, 417 mg). The solution was stirred at ambient temperature for 16 hr, diluted with dichloromethane and washed with 1M potassium hydroxide solution. The aqueous layer was separated and extracted with dichloromethane (2×25 mL). The combined organic layers were dried over anhydrous sodium sulfate and evaporated to dryness under vacuum. The residue was redissolved in toluene, evaporated to dryness and purified by chromatography on a 1 mm silica gel rotor eluting with a 0 to 10% methanol in dichloromethane gradient. Final purification from residual hexamethylphosphoramide was achieved by precipitation of the hydrochloride salt (as described above in Example 6), trituration with 1M potassium hydroxide solution, filtration and rinsing with water to give the title compound (46 mg, 23%).

MS: 567.2 [M+H]$^+$

The following Examples were prepared from (3R)-[1,4'] bipiperidinyl-3-yl-morpholin-4-yl-methanone by an analogous procedure using commercially available carboxylic acids (unless otherwise noted):

EXAMPLE 161

(3R)-[3-(Morpholine-4-carbonyl)-[1,4']bipiperidinyl-1'-yl]-[7-trifluoromethyl-2-(4-trifluoromethyl-phenyl)-quinolin-4-yl]-methanone

MS: 649.2 [M+H]$^+$

EXAMPLE 162

(3R)-[2-(4-Chloro-phenyl)-6-fluoro-quinolin-4-yl]-[3-(morpholine-4-carbonyl)-[1,4']bipiperidinyl-1'-yl]-methanone

MS: 565.0 [M+H]$^+$

EXAMPLE 163

(3R)-[2-(4-Chloro-phenyl)-6-trifluoromethoxy-quinolin-4-yl]-[3-(morpholine-4-carbonyl)-[1,4'] bipiperidinyl-1'-yl]-methanone

MS: 631.1 [M+H]$^+$

EXAMPLE 164

(3R)-[7-Chloro-2-(4-chloro-phenyl)-6-fluoro-quinolin-4-yl]-[3-(morpholine-4-carbonyl)-[1,4'] bipiperidinyl-1'-yl]-methanone

MS: 599.1 [M+H]$^+$

EXAMPLE 165

(3R)-(2,6-Diphenyl-pyridin-4-yl)-[3-(morpholine-4-carbonyl)-[1,4']bipiperidinyl-1'-yl]-methanone MS: 539.2 [M+H]$^+$ $^1$H-NMR (CDCl$_3$) δ 8.15–8.09 (m, 4H), 7.62 (s, 2H), 7.52–7.40 (m, 6H), 4.81 (dm, 1H, J=12.7 Hz), 3.78 (dm, 1H, J=13.1 Hz) 3.68–3.44 (m, 8H), 3.03 (tm, 1H, J=12.4 Hz), 2.94–2.83 (m, 2H), 2.78 (tm, 1H, J=12.5 Hz), 2.42 (tm, 1H, J=10.8 Hz), 2.18 (tm, 2H, J=11.2 Hz), 2.02–1.91 (m, 1H), 1.84–1.70 (m, 3H), 1.68–1.36 (m, 4H) ppm.

EXAMPLE 166

(3R)-[2,6-Bis-(4-chloro-phenyl)-pyridin-4-yl]-[3-(morpholine-4-carbonyl)-[1,4']bipiperidinyl-1'-yl]-methanone The title compound was prepared from 2,6-bis-(4-chloro-phenyl)-isonicotinic acid which was obtained according to a procedure described by P. Blumbergs et al. *J. Med. Chem.* 1972, 15, 808.

MS: 607.0 [M+H]$^+$ $^1$H-NMR (CDCl$_3$) δ 8.06 (dm, 4H, J=8.5 Hz), 7.60 (s, 2H), 7.47 (dm, 4H, J=8.5 Hz), 4.87–4.75 (m, 1H), 3.81–3.71 (m, 1H), 3.70–3.42 (m, 8H), 3.06 (brt, 1H, J=14.3 Hz), 2.96–2.84 (m, 1H), 2.79 (brt, 1H, J=13.5 Hz), 2.73–2.51 (m, 2H), 2.50–2.35 (m, 1H), 2.28–2.09 (m, 1H), 2.06–1.88 (m, 1H), 1.88–1.73 (m, 3H), 1.49–1.18 (m, 4H).

EXAMPLE 167

(3R)-[6-Chloro-2-(4-chloro-phenyl)-quinazolin-4-yl]-[3-(morpholine-4-carbonyl)-[1,4']bipiperidinyl-1'-yl]-methanone The title compound was prepared from 6-chloro-2-(4-chloro-phenyl)-quinazoline-4-carboxylic acid which was obtained according to a procedure analogous to that described by G. Giardina et al. *J. Med Chem.*, 1997, 40, 1794.

R$_F$ 0.44 (9:1 dichloromethane-methanol) MS: 582.0 [M+H]$^+$

EXAMPLE 168

(3R)-[6,7-Dichloro-2-(4-chloro-phenyl)-quinazolin-4-yl]-[3-(morpholine-4-carbonyl)-[1,4']bipiperidinyl-1'-yl]-methanone The title compound was prepared from 6,7-dichloro-2-(4-chloro-phenyl)-quinazoline-4-carboxylic acid which was obtained according to a procedure analogous to that described by G. Giardina et al. *J. Med Chem.*, 1997, 40, 1794.

MS: 615.9 [M+H]$^+$

EXAMPLE 169

(3R)-[5,6-Dichloro-2-(4-chloro-phenyl)-quinazolin-4-yl]-[3-(morpholine-4-carbonyl)-[1,4']bipiperidinyl-1'-yl]-methanone The title compound was prepared from 5,6-dichloro-2-(4-chloro-phenyl)-quinazoline-4-carboxylic acid which was obtained according to a procedure analogous to that described by G. Giardina et al. *J. Med Chem.*, 1997, 40, 1794.

MS: 618.1 [M+H]+

The following Examples were prepared from [1,4'] bipiperidinyl-3-carboxylic acid diethylamide by a procedure analogous to that used for the preparation of Example 160 using commercially available carboxylic acids (unless otherwise noted):

EXAMPLE 170

1'-(2-Pyridin-3-yl-quinoline-4-carbonyl)-[1,4'] bipiperidinyl-3-carboxylic acid diethylamide

MS: 500.1 [M+H]+

EXAMPLE 171

1'-(2-Pyridin-2-yl-quinoline-4-carbonyl)-[1,4'] bipiperidinyl-3-carboxylic acid diethylamide

MS: 500.1 [M+H]+

EXAMPLE 172

1'-(6-Bromo-2-pyridin-4-yl-quinoline-4-carbonyl)-[1,4']bipiperidinyl-3-carboxylic acid diethylamide

MS: 578.1 [M+H]+

EXAMPLE 173

1'-(6-Methyl-2-pyridin-4-yl-quinoline-4-carbonyl)-[1,4']bipiperidinyl-3-carboxylic acid diethylamide

MS: 514.3 [M+H]+

EXAMPLE 174

(3R)-(2,6-Diphenyl-pyridin-4-yl)-[3-(piperazine-1-carbonyl)-[1,4']bipiperidinyl-1'-yl]-methanone (3R)-4-[1'-(2,6-Diphenyl-pyridine-4-carbonyl)-[1,4'] bipiperidinyl-3-carbonyl]-piperazine-1-carboxylic acid tert-butyl ester (1.78 g, 2.79 mmol) was dissolved in ethyl acetate (25 mL) and cooled to −78° C. under nitrogen. Hydrogen chloride was passed in for several minutes and formation of a white precipitate was observed which redissolved almost immediately. When the solution was saturated with hydrogen chloride it was allowed to warmed to ambient temperature and after 1 h the solvent was evaporated in a stream of dry nitrogen, passing the evolved gasses to a water scrubber. A loose yellowish powder remained (2.02 g, >100% calculated as trishydrochloride). This was dissolved in water, basified by the addition of 2M sodium hydroxide (to pH 13.5) and extracted with dichloromethane (×3). The organic layer was dried over anhydrous sodium sulfate and evaporated to dryness to give the title compound as a powdery foam (1.37 g, 91%).

$^1$H-NMR (CDCl$_3$) δ 8.17–8.11 (m, 4H), 7.63 (s, 2H), 7.53–7.40 (m, 6H), 4.82 (brd, 1H, J=12.5 Hz), 3.85–3.72 (m, 1H), 3.64–3.49 (m, 2H), 3.49–3.42 (m, 2H), 3.04 (brt, 1H, J=12.5 Hz), 2.90 (brt, 2H, J=8.3 Hz), 2.86–2.76 (m, 4H), 2.74–2.64 (m, 1H), 2.62–2.52 (brt, 1H), 2.41 (brt, 1H, J=10.6 Hz), 2.18 (brt, 1H, J=10.6 Hz), 2.02–1.92 (m, 1H), 1.89–1.71 (m, 6H), 1.69–1.35 (m, 4H).

EXAMPLE 175

(3R)-Anthracen-9-yl-[3-(piperazine-1-carbonyl)-[1, 4']bipiperidinyl-1'-yl]-methanone The title compound was prepared by an analogous procedure from (3R)-4-[1'-(anthracene-9-carbonyl)-[1,4'] bipiperidinyl-3-carbonyl]-piperazine-1-carboxylic acid tert-butyl ester.

MS: 485.4 [M+H]+

EXAMPLE 176

(3R)-(2,6-Diphenyl-pyridin-4-yl)-{3-[4-(morpholine-4-carbonyl)-piperazine-1-carbonyl]-[1, 4']bipiperidinyl-1'-yl}-methanone (3R)-(2,6-Diphenyl-pyridin-4-yl)-[3-(piperazine-1-carbonyl)-[1,4']bipiperidinyl-1'-yl]-methanone (0.507 mmol, 272 mg) was dissolved in anhydrous dichloromethane and N,N-diisopropylethylamine (2 eq. 180 μl) followed by N-morpholine carbonyl chloride (1 eq. 60 μl) were added. After 3 hr a further aliquot of N-morpholine carbonyl chloride (40 μl) was added and the mixture was stirred at room temperature for 66 hr. The solution was washed with 0.1M sodium hydroxide solution, dried over anhydrous sodium sulfate, diluted with toluene and evaporated to dryness. The product was purified by chromatography on silica gel eluting with a 2.5% to 10% methanol-dichloromethane gradient to give the title compound (270 mg, 82%).

$R_F$ 0.35 (9:1 dichloromethane-methanol) MS: 651.2 [M+H]+

These reaction conditions were equally appropriate for reaction of this piperazine with other classes of acylating and alkylating agents. The following compounds were prepared from (3R)-(2,6-diphenyl-pyridin-4-yl)-[3-(piperazine-1-carbonyl)-[1,4']bipiperidinyl-1'-yl]-methanone using this protocol:

EXAMPLE 177

(3R)-4-[1'-(2,6-Diphenyl-pyridine-4-carbonyl)-[1,4'] bipiperidinyl-3-carbonyl]-piperazine-1-sulfonic acid dimethylamide

MS: 645.2 [M+H]+

EXAMPLE 178

(3R)-4-[1'-(2,6-Diphenyl-pyridine-4-carbonyl)-[1,4'] bipiperidinyl-3-carbonyl]-piperazine-1-carboxylic acid dimethylamide

MS: 609.3 [M+H]+

EXAMPLE 179

(3R)-4-[1'-(2,6-Diphenyl-pyridine-4-carbonyl)-[1,4'] bipiperidinyl-3-carbonyl]-piperazine-1-carboxylic acid diethylamide

MS: 637.3 [M+H]+

EXAMPLE 180

(3R)-{3-[4-(4-Chloro-benzoyl)-piperazine-1-carbonyl]-[1,4']bipiperidinyl-1'-yl}-(2,6-diphenyl-pyridin-4-yl)-methanone

MS: 676.2 [M+H]+

EXAMPLE 181

(3R)-[3-(4-Cyclopropanecarbonyl-piperazine-1-carbonyl)-[1,4']bipiperidinyl-1'-yl]-(2,6-diphenyl-pyridin-4-yl)-methanone

MS: 606.3 [M+H]+

EXAMPLE 182

(3R)-(2,6-Diphenyl-pyridin-4-yl)-[3-(4-ethanesulfonyl-piperazine-1-carbonyl)-[1,4'] bipiperidinyl-1'-yl]-methanone

MS: 630.2 [M+H]+

EXAMPLE 183

(3R)-1-{4-[1'-(2,6-Diphenyl-pyridine-4-carbonyl)-[1,4']bipiperidinyl-3-carbonyl]-piperazin-1-yl}-2-methyl-propan-1-one

MS: 608.3 [M+H]+

EXAMPLE 184

(3R)-({4-[1'-(2,6-Diphenyl-pyridine-4-carbonyl)-[1,4']bipiperidinyl-3-carbonyl]-piperazine-1-carbonyl}-amino)-acetic acid ethyl ester

MS: 667.3 [M+H]+

EXAMPLE 185

(3R)-{4-[1'-(2,6-Diphenyl-pyridine-4-carbonyl)-[1,4']bipiperidinyl-3-carbonyl]-piperazin-1-yl}-acetic acid

MS: 596.3 [M+H]+

EXAMPLE 186

(3R)-(2,6-Diphenyl-pyridin-4-yl)-[3-(4-methanesulfonyl-piperazine-1-carbonyl)-[1,4']bipiperidinyl-1'-yl]-methanone

MS: 616.2 [M+H]+

EXAMPLE 187

(3R)-{4-[1'-(2,6-Diphenyl-pyridine-4-carbonyl)-[1,4']bipiperidinyl-3-carbonyl]-piperazin-1-yl}-oxo-acetic acid ethyl ester

MS: 638.3 [M+H]+

EXAMPLE 188

(3R)-1-{4-[1'-(2,6-Diphenyl-pyridine-4-carbonyl)-[1,4']bipiperidinyl-3-carbonyl]-piperazin-1-yl}-2,2-dimethyl-propan-1-one

MS: 622.3 [M+H]+

EXAMPLE 189

(3R)-1-{4-[1'-(2,6-Diphenyl-pyridine-4-carbonyl)-[1,4']bipiperidinyl-3-carbonyl]-piperazin-1-yl}-3-methyl-butan-1-one

MS: 622.3 [M+H]+

EXAMPLE 190

(3R)-(2,6-Diphenyl-pyridin-4-yl)-{3-[4-(furan-2-carbonyl)-piperazine-1-carbonyl]-[1,4']bipiperidinyl-1'-yl}-methanone

MS: 632.2 [M+H]+

EXAMPLE 191

(3R)-1-{4-[1'-(2,6-Diphenyl-pyridine-4-carbonyl)-[1,4']bipiperidinyl-3-carbonyl]-piperazin-1-yl}-propan-1-one

MS: 594.2 [M+H]+

EXAMPLE 192

(3R)-4-[1'-(2,6-Diphenyl-pyridine-4-carbonyl)-[1,4']bipiperidinyl-3-carbonyl]-piperazine-1-carboxylic acid (4-fluoro-phenyl)-amide

MS: 675.3 [M+H]+

EXAMPLE 193

(3R)-4-[1'-(2,6-Diphenyl-pyridine-4-carbonyl)-[1,4']bipiperidinyl-3-carbonyl]-piperazine-1-carboxylic acid isopropyl-amide

MS: 623.3 [M+H]+

EXAMPLE 194

(3R)-(2,6-Diphenyl-pyridin-4-yl)-{3-[4-(trifluoro-methanesulfonyl)-piperazine-1-carbonyl]-[1,4']bipiperidinyl-1'-yl}-methanone

MS: 670.2 [M+H]+

EXAMPLE 195

(3R)-[3-(4-Cyclobutanecarbonyl-piperazine-1-carbonyl)-[1,4']bipiperidinyl-1'-yl]-(2,6-diphenyl-pyridin-4-yl)-methanone

MS: 620.3 [M+H]+

EXAMPLE 196

(3R)-(2,6-Diphenyl-pyridin-4-yl)-{3-[4-(thiophene-2-carbonyl)-piperazine-1-carbonyl]-[1,4']bipiperidinyl-1'-yl}-methanone

MS: 648.2 [M+H]+

EXAMPLE 197

(3R)-(2,6-Diphenyl-pyridin-4-yl)-{3-[4-(Propane-2-sulfonyl)-piperazine-1-carbonyl]-[1,4']bipiperidinyl-1'-yl}-methanone

MS: 644.2 [M+H]+

EXAMPLE 198

(3R)-{4-[1'-(2,6-Diphenyl-pyridine-4-carbonyl)-[1,4']bipiperidinyl-3-carbonyl]-piperazin-1-yl}-acetic acid ethyl ester

MS: 624.2 [M+H]+

EXAMPLE 199

(3R)-[3-(4-Benzoyl-piperazine-1-carbonyl)-[1,4']bipiperidinyl-1'-yl]-(2,6-diphenyl-pyridin-4-yl)-methanone

MS: 642.3 [M+H]+

EXAMPLE 200

(3R)-4-[1'-(2,6-Diphenyl-pyridine-4-carbonyl]-[1,4']bipiperidinyl-3-carbonyl]-piperazine-1-carboxylic acid benzylamide

MS: 671.3 [M+H]+

EXAMPLE 201

(3R)-(2,6-Diphenyl-pyridin-4-yl)-{3-[4-(3-hydroxy-propyl)-piperazine-1-carbonyl]-[1,4']bipiperidinyl-1'-yl}-methanone

MS: 596.2 [M+H]+

EXAMPLE 202

(3R)-Acetic acid 2-{4-[1'-(2,6-diphenyl-pyridine-4-carbonyl)-[1,4']bipiperidinyl-3-carbonyl]-piperazin-1-yl}-2-oxo-ethyl ester

MS: 638.3 [M+H]+

EXAMPLE 203

(3R)-{4-[1'-(2,6-Diphenyl-pyridine-4-carbonyl)-[1,4']bipiperidinyl-3-carbonyl]-piperazine-1-carbonyl}-carbamic acid ethyl ester

MS: 653.2 [M+H]$^+$

EXAMPLE 204

(3R)-(2,6-Diphenyl-pyridin-4-yl)-{3-[4-(isoxazole-5-carbonyl)-piperazine-1-carbonyl]-[1,4']bipiperidinyl-1'-yl}-methanone

MS: 633.3 [M+H]$^+$

EXAMPLE 205

(3R)-4-[1'-(2,6-Diphenyl-pyridine-4-carbonyl)-[1,4']bipiperidinyl-3-carbonyl]-piperazine-1-carboxylic acid pyridin-3-ylamide

MS: 658.2 [M+H]$^+$

EXAMPLE 206

(3R)-1-{4-[1'-(2,6-Diphenyl-pyridine-4-carbonyl)-[1,4']bipiperidinyl-3-carbonyl]-piperazin-1-yl}-ethanone $R_F$ 0.25 (9:1 dichloromethane-methanol) MS: 580.0 [M+H]$^+$ The following compounds were prepared from (3R)-anthracen-9-yl-[3-(piperazine-1-carbonyl)-[1,4']bipiperidinyl-1'-yl]-methanone and commercially obtained reagents by a procedure similar to that described above for Example 176.

EXAMPLE 207

(3R)-Anthracen-9-yl-{3-[4-(morpholine-4-carbonyl)-piperazine-1-carbonyl]-[1,4']bipiperidinyl-1'-yl}-methanone $R_F$ 0.36 (9:1 dichloromethane-methanol) MS: 598.5 [M+H]$^+$ $^1$H-NMR (CDCl$_3$) δ 8.45 (s, 1H), 8.05–7.95 (m, 3H), 7.90–7.80 (m, 1H), 7.55–7.4 (m, 4H), 5.20 (brd, 1H, J=13.1 Hz), 3.71–3.63 (m, 4H), 3.62–3.54 (m, 2H), 3.53–3.50 (m, 2H), 3.40–3.15 (m, 7H), 3.04–2.96 (m, 1H), 2.95–2.82 (m, 3H), 2.70 (brt, 1H, J=10.8 Hz), 2.50 (brt, 1H, J=10.9 Hz), 2.37 (brt, 1H, J=10.9 Hz), 2.17–2.05 (m, 2H), 1.82–1.69 (m, 6H), 1.60–1.35 (m, 4H).

EXAMPLE 208

(3R)-Anthracen-9-y-{3-[4-(propane-2-sulfonyl)-piperazine-1-carbonyl]-[1,4']bipiperidinyl-1'-yl}-methanone $R_F$ 0.41 (9:1 dichloromethane-methanol) MS: 591.5 [M+H]$^+$

EXAMPLE 209

(3R)-4-[1'-(Anthracene-9-carbonyl)-[1,4']bipiperidinyl-3-carbonyl]-piperazine-1-sulfonic acid dimethylamide $R_F$ 0.40 (9:1 dichloromethane-methanol) MS: 592.5 [M+H]$^+$

EXAMPLE 210

(3R)-Anthracen-9-yl-{3-[4-(Pyrrolidine-1-carbonyl)-piperazine-1-carbonyl]-[1,4']bipiperidinyl-1'-yl}-methanone $R_F$ 0.32 (9:1 dichloromethane-methanol) MS: 582.5 [M+H]$^+$

EXAMPLE 211

(3R)-4-[1'-(Anthracene-9-carbonyl)-[1,4']bipiperidinyl-3-carbonyl]-piperazine-1-carboxylic acid dimethylamide $R_F$ 0.35 (9:1 dichloromethane-methanol) MS: 556.5 [M+H]$^+$

EXAMPLE 212

(3R)-4-[1'-(2,6-Diphenyl-pyridine-4-carbonyl)-[1,4']bipiperidinyl-3-carbonyl]-piperazine-1-carboxylic acid amide (3R)-(2,6-Diphenyl-pyridin-4-yl)-[3-(piperazine-1-carbonyl)-[1,4']bipiperidinyl-1'-yl]-methanone (21.4 mg, 0.040 mmol) and sodium cyanate (0.060 mmol, 3.9 mg) were heated at 100° C. in a water-dioxane-n-propanol solution. After 2 h an additional aliquot of sodium cyanate (4 mg) was added and heating was continued for another 1 hour then the solution was allowed to stir at ambient temperature for an additional 42 h. The solvent was removed under vacuum and the product was purified by silica gel chromatography eluting with a 5% to 10% methanol-dichloromethane gradient to give the title compound (9.3 mg, 40%).

$R_F$ 0.21 (9:1 dichloromethane-methanol) MS: 581.5 [M+H]$^+$

EXAMPLE 213

(3R)-1-[1-(Anthracene-9-carbonyl)-pyrrolidin-3-yl]-piperidine-3-carboxylic acid ethyl ester Reductive amination of 1-benzyl-pyrrolidin-3-one with (3R)-ethyl nipecotate was carried out according to the procedure described above for Intermediate 1 to give (3R)-1-(1-benzyl-pyrrolidin-3-yl)-piperidine-3-carboxylic acid ethyl ester (containing a small amount of the isopropyl ester) as a yellow oil (1.23 g, 39%).

The mixture of ethyl and isopropyl esters (1.23 g) was dissolved in anhydrous ethanol (~50 mL) and dilute hydrochloric acid (2N, 4 mL) and 10% palladium on carbon (120 mg) was added. The suspension was shaken under hydrogen (48 psi) in a Parr shaker for 16 hr. Only a very small amount reduction occurred so the catalyst was filtered off and the solvent removed under vacuum. The residue was dissolved in glacial acetic acid, platinum (IV) oxide (100 mg) was added and the suspension shaken under 50 psi hydrogen at 60° C. overnight. The solvent was evaporated under vacuum, the residue dissolved in dichloromethane/methanol and the catalyst was filtered off though Celite®. The solvent was again evaporated and the residue partitioned between dilute hydrochloric acid and ethyl acetate (×3). The aqueous layer was made basic with 14% w/v sodium hydroxide and re-extracted with ethyl acetate. The organic layer was dried over anhydrous sodium sulfate and the solvent was removed under vacuum. The product was purified by chromatography on silica gel eluting with 5%–10%–40%-methanol-dichloromethane to give (3R)-1-pyrrolidin-3-yl-piperidine-3-carboxylic acid ethyl ester (36.9 mg). This amine was reacted with anthracene-9-carbonyl chloride (Intermediate 3) by a procedure analogous to that described above for the preparation of Example 1 to give the title compound (70.1mg, 100%).

$R_F$ 0.70 (9:1 dichloromethane-methanol) MS: 431.3 [M+H]$^+$

EXAMPLE 214

(3R)-1-[1-(Anthracene-9-carbonyl)-pyrrolidin-3-yl]-piperidine-3-carboxylic acid diethylamide (3R)-1-[1-(Anthracene-9-carbonyl)-pyrrolidin-3-yl]-piperidine-3-carboxylic acid ethyl ester (53.2 mg) was heated under reflux with 2N hydrochloric acid (containing some dioxane to produce clear solution) for 30 minutes. The water was evaporated under vacuum, toluene was added to the residue and this was removed under vacuum (×2) to dry the product. The residue was heated under reflux in chloroform containing 0.3 mL of thionyl chloride until all the solid was dissolved (~15 min) then the solvent was evaporated to dryness. The residue was dissolved in anhydrous dichloromethane (5 mL) and diethylamine (100 pi) was added. After 1 h the solvent was evaporated under vacuum, the residue was dissolved in dichloromethane, washed with dilute sodium hydroxide, dried over anhydrous sodium sulfate and evaporated. The product was purified by chromatography on silica gel eluting with a 1%–2.5%–5% methanol-dichloromethane gradient to give the title compound as a mixture of diastereoisomers (46.2 mg, 82%).

$R_F$ 0.35 (9:1 dichloromethane-methanol) MS: 458.4 $[M+H]^+$

The sample is a mixture of diastereoisomers.

$^{13}$C-NMR (CDCl$_3$) δ 173.20, 172.95, 168.96, 168.86, 131.23, 128.70, 128.66, 128.62, 127.78, 127.37, 127.23, 127.14, 126.88, 126.79, 125.73, 125.56, 125.53, 125.43, 124.87, 124.73, 124.69, 124.53, 64.68, 64.61, 63.77, 63.64, 55.93, 55.30, 54.49, 54.33, 53.07, 52.44, 51.77, 51.48, 51.34, 50.09, 50.03, 46.60, 46.57, 44.54, 42.03, 41.82, 41.75, 41.58, 40.03, 40.12, 39.86, 39.69, 39.57, 39.40, 39.29, 30.36, 30.15, 28.88, 28.76, 28.00, 27.95, 27.69, 27.52, 25.05, 24.90, 24.67, 15.20, 15.07, 15.01, 14.75, 13.22, 13.13, 13.10, 12.98.

EXAMPLE 215

1'-(Anthracene-9-carbonyl)-5,6,1',2',3',4',5',6'-octahydro-4H-[1,4']bipyridinyl-3-carboxylic acid diethylamide Anthracen-9-yl-[1,4']bipiperidinyl-1'-yl-methanone was prepared as a pale yellow powder from 4-piperidinopiperidine and anthracene-9-carbonyl chloride (Intermediate 3) by a procedure analogous to that described above for the preparation of Example 127.

MS: 373.3 $[M+H]^{+R}{}_F$ 0.20 (9:1 dichloromethane-methanol)

To a solution of anthracen-9-yl-[1,4']bipiperidinyl-1'-yl-methanone(135–5 mg, 0.36 mmol) in dichloromethane (10 mL) under nitrogen at −78° C. was added a solution of metachlorperbenzoic acid (Aldrich, 57–83%, 106 mg) in dichloromethane (2.3 mL). The solution was allowed to warm to ambient temperature and the reaction was complete by thin layer chromatography (9:1 dichloromethane-methanol). The solution was diluted with dichloromethane, washed with dilute sodium hydroxide, dried over anhydrous sodium sulfate and evaporated to dryness. The residue was redissolved in a little dichloromethane, toluene added and the solvent was removed under vacuum to dryness to give anthracen-9-yl-(1-oxy-[1,4']bipiperidinyl-1'-yl)-methanone as a pale yellow powder.

MS: 389.3 $[M+H]^{+R}{}_F$ 0.55 (4:1 dichloromethane-methanol)

To a solution of anthracen-9-yl-(1-oxy-[1,4'] bipiperidinyl-1'-yl)-methanone (38 mg, 0.098 mmol) in anhydrous dichloromethane (0.5 mL) under nitrogen was added N,N-diisopropylethylamine (3 eq., 51 µl). After cooling to −78° C. phosgene (1.93 M solution in toluene, 5 eq., 0.49 mmol, 250 µl) was added. A brownish color developed. The solution was stirred at −78° C. for 2 hr then warmed to ambient temperature for 15 min before recooling to −78° C. Diethylamine (6.8 eq., 0.67 mmol, 70 µl) was added, the solution warmed to ambient temperature, diluted with dichloromethane and washed with 0.1 M sodium hydroxide solution. The solution was dried over anhydrous sodium sulfate and evaporated to a dark colored oil. This material was purified by chromatography on silica gel eluting with a 1% to 10% methanol-dichloromethane gradient to give the title compound as an oil (15.5mg).

$R_F$ 0.50 (9:1 dichloromethane-methanol) MS: 470.3 $[M+H]^+$

EXAMPLE 216

1'-(1,2,3,4-Tetrahydro-anthracene-9-carbonyl)-[1,4'] bipiperidinyl-3-carboxylic acid diethylamide 1'-(Anthracene-9-carbonyl)-5,6,1',2',3',4',5',6'-octahydro-4H-[1,4']bipyridinyl-3-carboxylic acid diethylamide (0.033 mmol, 15.5 mg) was dissolved in methanol (~20 mL), 10% palladium on carbon (10% w/w) (30 mg) was added and the suspension was shaken under a hydrogen atmosphere (45 psi) for 42 h at room temperature in a Parr shaker. The catalyst was filtered off, the solvent evaporated and the residue was purified by chromatography on silica gel eluting with a 1%–5% methanol-dichloromethane gradient to give the title compound (5.3 mg, 34%).

$R_F$ 0.53 (9:1 dichloromethane-methanol) MS: 389.3 $[M+H]^+$

EXAMPLE 217

1-[1-(Anthracene-9-carbonyl)-piperidin-4-yl]-azepane-3-carboxylic acid diethylamide A mixture of tert-butyl 4-oxo-1-piperidinecarboxylate (10 mmol, 1.99 mmol), azepane (10 mmol, 990 mg) and titanium isopropoxide (12.5 mmol, 3.7 mL) was stirred at room temperature for 50 mins. A solution of sodium cyanoborohydride (7 mmol, 440 mg) in anhydrous ethanol (10 mL) was added and the solution was stirred under nitrogen at ambient temperature for 24 hr. Water (2 mL) was added and the precipitate was removed by filtration through Celite®, rinsing through with ethanol. The solvent was removed under vacuum and the residue purified by chromatography on silica gel eluting with a 5%–10% methanol-dichloromethane gradient to give 4-azepan-1-yl-piperidine-1-carboxylic acid tert-butyl ester (726 mg, 26%).

MS: 389.3 $[M+H]^+$ $R_F$ 0.38 (9:1 dichloromethane-methanol)

To a solution of 4-azepan-1-yl-piperidine-1-carboxylic acid tert-butyl ester (545 mg, 1.93 mmol) in dichloromethane (10 mL) at −78° C. was added a solution of metachloroperbenzoic acid (2 mmol, 610 mg) in dichloromethane (10 mL, dried over a little anhydrous sodium sulfate). A white precipitate was formed which redissolved as the solution was allowed to warm to ambient temperature. The solution was then washed with saturated sodium hydrogen carbonate solution and a little 2N sodium hydroxide, dried over anhydrous sodium sulfate and evaporated under vacuum. The residue was purified by chromatography on silica gel eluting with a 10% to 20% methanol-dichloromethane gradient to give 4-(1-oxy-azepan-1-yl)-piperidine-1-carboxylic acid tert-butyl ester as an oil which on trituration with hexane gave a white friable powder (483 mg, 84%).

$R_F$ 0.25 (4:1 dichloromethane-methanol)

This N-oxide (263 mg, 0.88 mmol) was dissolved in anhydrous dichloromethane (5 mL) and N,N- diisopropylethylamine (4 eq, 615 µL) was added. The solution was cooled to −78° C. and phosgene (1.93M, 3 eq, 1.37 mL) was added. The yellow solution was allowed to warm, becoming red by 0° C. The mixture was immediately recooled to −78° C. and diethylamine (5 eq., 460 µL) was added. The mixture warmed to ambient temperature, washed with a mixture of sodium hydrogen carbonate/sodium hydroxide solutions, dried over anhydrous sodium sulfate, evaporated under vacuum and the residue was purified by chromatography on silica gel eluting with a 1%–2.5%–5%–10% methanol-dichloromethane gradient to give 4-(6-diethylcarbamoyl-2,3,4,5-tetrahydro-azepin-1-yl)-piperidine-1-carboxylic acid tert-butyl ester (30 mg, 9%)

MS: 380.3 [M+H]$^+$ R$_F$ 0.34 (acetone-hexane 1:1)

4-(6-diethylcarbamoyl-2,3,4,5-tetrahydro-azepin-1-yl)-piperidine-1-carboxylic acid tert-butyl ester (30 mg, 0.079 mmol) was dissolved in methanol (20 mL) and 10% palladium on carbon (10% w/w) (~30 mg) added. The mixture was shaken under a hydrogen atmosphere (50 psi) for 3 h. The catalyst was removed by filtration through Celite® and the solvent evaporated under vacuum. The residue was dissolved in ethyl acetate (10 mL) under nitrogen, cooled to −78° C. and hydrogen chloride was passed in for a few minutes. The solution was allowed to warmed at room temperature then evaporated to dryness overnight in a stream of dry nitrogen. The residue was dissolved in anhydrous dichloromethane (4 mL), N,N-diisopropylethylamine (5 eq, 70 mL) was added followed by a suspension of anthracene-9-carbonyl chloride (Intermediate 3, 0.088 mmol) in dichloromethane (0.175 mL). The thin layer chromatography (9:1 dichloromethane-methanol) showed a new UV spot at Rf 0.40. After 30 minutes, the solution was washed with a mixed sodium hydrogen carbonate/sodium hydroxide solution, dried over anhydrous sodium sulfate, evaporated and the residue purified by chromatography on silica gel eluting with a 1%–2.5%–5%–10% methanol-dichloromethane gradient to give the title compound (20.4 mg, 53%).

R$_F$ 0.40 (9:1 dichloromethane-methanol) MS: 486.3 [M+H]$^+$

EXAMPLE 218

1-[1-(Anthracene-9-carbonyl)-piperidin-4-yl]-pyrrolidine-3-carboxylic acid diethylamide To a solution of 1-benzyl-5-oxo-pyrrolidine-3-carboxylic acid methyl ester (30 mmol, 7 g) in anhydrous tetrahydrofuran (40 ml) was added borane-tetrahydrofuran solution (1M, 50 mmol, 50 mL) at ambient temperature. When gas evolution had subsided the solution was heated under reflux for 75 min then stirred for 16 hr at ambient temperature. Hydrochloric acid (6M) was added dropwise (ca. 5 mL) and the mixture was stirred at ambient temperature for 1 hr before removing the solvent under vacuum. The residue was dissolved in dichloromethane and the solution was washed with dilute sodium hydroxide solution. The dichloromethane solution was then extracted with dilute hydrochloric acid (×3), the extracts combined, made basic by addition of sodium hydroxide and extracted with dichloromethane (×3). The combined organic extract was dried over anhydrous sodium sulfate and the solvent was removed under vacuum. The product was purified by chromatography on silica gel eluting with 5% methanol-dichloromethane to give 1-benzyl-pyrrolidine-3-carboxylic acid methyl ester (200 mg, 3%).

MS: 220.2 [M+H]$^+$ R$_F$ 0.38 (19:1 dichloromethane-methanol)

A solution of 1-benzyl-pyrrolidine-3-carboxylic acid methyl ester (109.6 mg, 0.5 mmol) in 2N hydrochloric acid (3 mL) and dioxane (1 mL) was heated to 80–90° C. for 1 h. The solvent was evaporated under vacuum and the residue redissolved in dioxane/methanol/toluene and evaporated under vacuum. The residue was then heated under reflux in chloroform containing an excess of thionyl chloride for 1 h and then the solvent was evaporated under vacuum. The residue was dissolved in anhydrous dichloromethane (5 mL) and diethylamine (300 µL) was added. After 20 minutes the solvent was evaporated and the residue dissolved in dichloromethane, washed with dilute sodium hydroxide, dried over anhydrous sodium sulfate and evaporated under vacuum. This material was dissolved in anhydrous acetonitrile (2 mL) and 2,2,2-trichloroethyl chloroformate (1.1 eq, 76 µL) was added at room temperature. After 1.5 h a further aliquot of the chloroformate (0.52 eq., 36 µL) was added. After 30 minutes thin layer chromatography (5% methanol-dichloromethane) indicated that the reaction was still incomplete so a further aliquot of the chloroformate (0.52 eq., 36 µL) and N,N-diisopropylethylamine (0.2 eq., 20 µL) was added. After 1 h the reaction was diluted with dichloromethane, washed with dilute sodium hydroxide, dried over anhydrous sodium sulfate and evaporated under vacuum. The residue was purified by chromatography on silica gel eluting with 40:1 dichloromethane-methanol to give 3-diethylcarbamoyl-pyrrolidine-1-carboxylic acid 2,2,2-trichloro-ethyl ester (102.2 mg, 60%)

MS: 345.2 [M+H]$^+$ R$_F$ 0.50 (40:1 dichloromethane-methanol).

This material was dissolved in anhydrous ethanol (5 mL) and zinc dust (freshly washed with dilute hydrochloric acid and dried under nitrogen, 20 eq, 390 mg) was added. The suspension was heated under reflux for 1 hr, the solid was removed by filtration through Celite® and the solvent evaporated under vacuum to give impure pyrrolidine-3-carboxylic acid diethylamide (75.1 mg, >100%). This compound was taken forward to give the title compound using a series of reactions analogous to those use in the preparation of the preparation of Example 1.

MS: 458.2 [M+H]$^+$ R$_F$ 0.33 (9:1 dichloromethane-methanol) $^1$H-NMR (CDCl$_3$) δ 8.44 (s, 1H), 8.09–7.90 (m, 3H), 7.85–7.75 (m, 1H), 7.60–7.40 (m, 4H), 5.17 (brd, 1H, J=13.2 Hz), 4.17–4.04 (m, 2H), 3.20 (dm, 1H, J=13.5 Hz), 3.06–2.92 (m, 2H), 2.87 (tm, 1H, J=13.0 Hz), 2.80–2.67 (m, 1H), 2.56–2.43 (m, 2H), 2.39–2.28 (m, 1H), 2.21–2.11 (m, 1H), 2.11–2.03 (m, 1H), 1.96–1.83 (m, 2H), 1.78–1.65 (m, 2H), 1.58–1.36 (m, 3H), 1.27–1.15 (m, 3H).

EXAMPLES 219 AND 220

(trans-)(1'R,3'R)-Anthracen-9-yl-{4-[3-(morpholine-4-carbonyl)-cyclohexyl]-piperazin-1-yl}-methanone and (cis-)(1'S,3'R)-anthracen-9-yl-{4-[3-(morpholine-4-carbonyl)-cyclohexyl]-piperazin-1-yl}-methanone (1R)-3-Oxo-cyclohexanecarboxylic acid was prepared according to the procedure described by R. D. Allan et al. in *Aust. J. Chem.*, 1981, 34, 2231. A solution of (1R)-3-oxo-cyclohexanecarboxylic acid (1 eq, 2.52 g, 18.1 mmol), 3-(diethoxyphosphoryloxy)-1,2,3-benzotriazin-4(3H)-one (DEPBT, H. Li et al. *Organic Letters*, 1999, 1, 91) (1.05 eq, 19.0 mmol, 5.68 g) and N,N-diisopropylethylamine (15 eq, 27.1 mmol, 4.7 mL) in anhydrous dichloromethane (70 mL) was allowed to stir at room temperature for 75 minutes. Morpholine (1.2 eq, 21.72 mmol, 1.9 mL) was added and the solution was stirred at ambient temperature for 16 h. The mixture was concentrated under vacuum to an oil which was purified by flash chromatography eluting with a 2.5% methanol-dichloromethane gradient on silica gel to give (3R)-3-(morpholine-4-carbonyl)-cyclohexanone (2.05 g, 54%).

MS: 212.4 [M+H]$^+$

To a solution of piperazine-1-carboxylic acid tert-butyl ester (1.05 eq, 0.99 mmol, 185 mg) and (3R)-3-(morpholine-4-carbonyl)-cyclohexanone (1 eq, 0.95 mmol, 200 mg) dissolved in anhydrous acetonitrile (2 mL) was added a solution of sodium cyanoborohydride (0.54 eq, 0.51 mmol, 32 mg) in acetonitrile (2 mL). Glacial acetic acid was added to the mixture until the solution indicated a pH of 4 by wet pH paper. The mixture was stirred at ambient temperature for 4 hr then concentrated under vacuum to a white foam. This material was purified by flash chromatography on silica gel eluting with a 1%–2.5%–5%–10% methanol-dichloromethane gradient to give a mixture of cis- and trans-(3R)-4-[3-(morpholine-4-carbonyl)-cyclohexyl]-piperazine-1-carboxylic acid tert-butyl ester (200 mg, 55%). The isomers were separated by chromatography on silica gel eluting with 60% ethyl acetate/30% hexane/10% triethylamine to give (trans)-(1'R,3'R)-4-[3-(morpholine-4-carbonyl)-cyclohexyl]-piperazine-1-carboxylic acid tert-butyl ester (100 mg, R$_F$ 0.5) and (cis-)(1'S,3'R)-4-[3-(morpholine-4-carbonyl)-cyclohexyl]-piperazine-1-carboxylic acid tert-butyl ester (50 mg, R$_F$ 0.4).

MS: 382.6 [M+H]$^+$ (both compounds)

Both isomers of (3R)-4-[3-(morpholine-4-carbonyl)-cyclohexyl]-piperazine-1-carboxylic acid tert-butyl ester were independently converted by deprotection and acylation reactions analogous to those described above for the preparation of Intermediate 2 and Example 1 to give the title compounds

EXAMPLE 219

R$_F$ 0.42 (9:1 dichloromethane-methanol) MS: 486.4 [M+H]$^+$

EXAMPLE 220

R$_F$ 0.39 (9:1 dichloromethane-methanol) MS: 486.4 [M+H]$^+$

EXAMPLE 221

Anthracen-9-yl-[3-(1-ethyl-1-hydroxy-propyl)-[1,4'] bipiperidinyl-1'-yl]-methanone To a solution of (3R)-1'-(anthracene-9-carbonyl)-[1,4'] bipiperidinyl-3-carboxylic acid diethylamide (Intermediate 22, 22.2 mg, 47 μmol) in anhydrous tetrahydrofuran (0.5 mL) under nitrogen at −25° C. was added a solution of ethylmagnesium bromide (1M in tetrahydrofuran, 2.1 eq., 0.1 mL). The solution was allowed to warm to ambient temperature and after 30 min a further addition of ethylmagnesium bromide (1M in tetrahydrofuran, 4.2 eq., 0.2 mL) was made. The mixture was stirred for 16 hr at ambient temperature before quenching with methanol. The mixture was diluted with dichloromethane, washed with a mixture of sodium hydroxide and sodium hydrogen carbonate solutions, dried over anhydrous sodium sulfate and the solvent was removed by evaporation under vacuum. The crude product was purified by chromatography on silica gel eluting with a 1%–10% methanol-dichloromethane gradient to give the title compound (3.2 mg, 15%).

R$_F$ 0.31 (9:1 dichloromethane-methanol) MS: 459.3 [M+H]$^+$

What is claimed is:

1. A compound of the Formula I

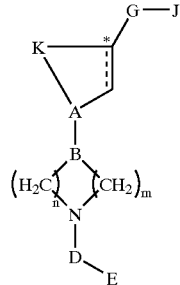

Formula 1 prodrugs thereof, or pharmaceutically acceptable salts of said compounds or of said prodrugs;

wherein A-B is CH—N;

K is (CH$_2$)r wherein r is 3;

m and n are each independently 2;

D is carbonyl or sulfonyl;

E is either a.) a bicyclic ring consisting of two fused fully unsaturated five or six membered rings, taken independently, or b.) a tricyclic ring consisting of two fused fully unsaturated five or six membered rings, taken independently, said two fused rings fused to a third fully unsaturated five or six membered ring; or c.) a tetracyclic ring comprising a bicyclic ring consisting of two fused fully unsaturated five or six membered rings, taken independently, said bicyclic ring fused to two fully unsaturated five or six membered monocyclic rings taken independently, or said bicyclic ring fused to a second bicyclic ring consisting of two fused fully unsaturated five or six membered rings, taken independently;

wherein said E bi-, tri- or tetra cyclic ring is optionally mono-, di- or tri-substituted independently on each ring used to form the bi-, tri- or tetra cyclic ring with halo, hydroxy, amino, cyano, nitro, oxo, carboxy, (C$_1$–C$_8$) alkyl, (C$_2$–C$_6$)alkenyl, (C$_2$–C$_6$)alkynyl, (C$_1$–C$_8$) alkoxy, (C$_1$–C$_4$)alkylthio, (C$_1$–C$_6$)alkoxycarbonyl, C$_1$–C$_6$) alkylcarbonyl, (C$_1$–C$_8$)alkylcarbonylamino, or mono-N- or di-N,N-C$_1$–C$_6$)alkylamino, mono-N- or di-N,N-(C$_1$–C$_6$)alkylaminocarbonyl wherein said (C$_1$–C$_6$)alkyl, (C$_1$–C$_6$)alkoxy and (C$_1$–C$_4$)alkylthio substituents are also optionally mono-, di- or tri-substituted independently with chloro, bromo, hydroxy, (C$_1$–C$_6$)alkoxy, amino, mono-N- or di-N,N-(C$_1$–C$_8$) alkylamino or from one to nine fluorines; and wherein said E bi-, tri- or tetra-cyclic ring is optionally mono-substituted with a partially saturated, fully saturated or fully unsaturated three to eight membered ring R$^{10}$ or a bicyclic ring R$^{11}$ consisting of two fused partially saturated, fully saturated or fully unsaturated three to eight membered rings, taken independently, said R$^{10}$ and R$^{11}$ rings optionally additionally bridged and said R$^{10}$ and R$^{11}$ rings optionally linked through a fully saturated, partially unsaturated or fully unsaturated one to four membered straight or branched carbon chain wherein the carbon(s) may optionally be replaced with one or two heteroatoms selected independently from oxygen, nitrogen and sulfur, provided said E bicyclic ring has at least one substituent and the E bicyclic ring atom bonded to D is carbon;

wherein said $R^{10}$ or $R^{11}$ ring is optionally mono-, di- or tri-substituted independently with halo, hydroxy, amino, cyano, nitro, oxo, carboxy, $(C_1-C_6)$alkyl, $(C_2-C_6)$alkenyl, $(C_2-C_6)$alkynyl, $(C_1-C_6)$alkoxy, $(C_1-C_4)$alkylthio, $(C_1-C_6)$alkoxycarbonyl, $(C_1-C_6)$alkylcarbonyl, $(C_1-C_6)$alkylcarbonylamino, or mono-N- or di-N,N-$(C_1-C_6)$alkylamino or mono-N- or di-N, N-$(C_1-C_6)$alkylaminocarbonyl wherein said $(C_1-C_6)$alkyl and $(C_1-C_6)$alkoxy substituents are also optionally mono-, di- or tri-substituted independently with halo, hydroxy, $(C_1-C_6)$alkoxy, amino, mono-N- or di-N,N-$(C_1-C_6)$alkylamino or from one to nine fluorines;

G is carbonyl, or sulfonyl;

J is $NR^2R^3$;

wherein $R^2$ and $R^3$ are taken together with the nitrogen atom to which they are attached to form a partially saturated, fully saturated or fully unsaturated six membered ring optionally having one additional heteroatoms selected independently from oxygen and sulfur;

wherein said $NR^2R^3$ ring is optionally mono-, di-, tri- or tetra-substituted independently with $R^{15}$, halo, hydroxy, amino, nitro, cyano, oxo, carboxy, $(C_1-C_6)$ alkyl, $(C_2-C_6)$alkenyl, $(C_2-C_6)$alkynyl, $(C_1-C_6)$ alkoxy, $(C_1-C_4)$alkylthio, $(C_1-C_6)$alkylcarbonylamino or mono-N- or di-N,N-(C1–C6)alkylamino, wherein said $(C_1-C_6)$alkyl substituent is optionally mono-, di- or tri-substituted independently with halo, hydroxy, amino, nitro, cyano, oxo, carboxy, $(C_1-C_6)$alkoxy, $(C_1-C_4)$alkylthio, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines;

wherein $R^{15}$ is carbonyl, carbamoyl, sulfonyl or sulfamoyl substituted with H, $(C_1-C_6)$alkyl, $(C_1-C_6)$ alkyloxy, $(C_1-C_6)$alkyloxycarbonyl, $(C_1-C_6)$ alkyloxycarbonyl$(C_1-C_6)$alkyl, mono-N- or di-N, N-$(C_1-C_6)$alkylamino, wherein said $(C_1-C_6)$alkyl substituent is optionally mono-, di- or tri-substituted independently with halo, hydroxy, amino, nitro, cyano, oxo, carboxy, $(C_1-C_6)$alkoxy, $(C_1-C_4)$alkylthio, $(C_1-C_6)$ alkyloxycarbonyl, $(C_1-C_6)$alkylcarbonyloxy, mono-N- or di-N,N-$(C_1-C_6)$alkylamino or the $R^{15}$ carbonyl, carbamoyl, sulfonyl or sulfamoyl linked substituent is a partially saturated, fully saturated or fully unsaturated three to eight membered ring optionally linked through $(C_1-C_6)$alkyl wherein said ring is optionally mono-, di- or tri-substituted with halo, hydroxy, amino, nitro, cyano, oxo, carboxy, $(C_1-C_6)$ alkyl, $(C_2-C_6)$alkenyl, $(C_2-C_6)$alkynyl, $(C_1-C_4)$alkylthio, $(C_1-C_6)$alkoxy, $(C_1-C_6)$alkylcarbonylamino, mono-N- or di-N,N-$(C_1-C_6)$alkylamino;

wherein said $NR^2R^3$ ring is optionally substituted with a partially saturated, fully saturated or fully unsaturated three to eight membered ring or a bicyclic ring consisting of two fused partially saturated, fully saturated or fully unsaturated three to six membered rings, taken independently, said bicyclic ring, said mono or bicyclic ring optionally additionally bridged said ring optionally having one to three heteroatoms selected independently from oxygen, sulfur and nitrogen, wherein said $(C_1-C_6)$ alkyl and said ring are optionally mono-, di- or tri-substituted with halo, hydroxy, amino, nitro, cyano, oxo, carboxy, $(C_2-C_6)$alkenyl, $(C_3-C_6)$alkynyl, $(C_1-C_6)$alkylcarbonylamino, hydroxy, $(C_1-C_6)$alkoxy, $(C_1-C_4)$alkylthio, $(C_1-C_6)$alkoxy, mono-N- or di-N,N-$(C_1-C_6)$alkylamino.

\* \* \* \* \*